(12) United States Patent
Weatherspoon et al.

(10) Patent No.: US 11,883,472 B2
(45) Date of Patent: Jan. 30, 2024

(54) RUSALATIDE ACETATE COMPOSITIONS

(71) Applicant: AFFIRMED PHARMA, LLC, Conroe, TX (US)

(72) Inventors: John K. Weatherspoon, Houston, TX (US); Jane Lea Hicks, Conroe, TX (US)

(73) Assignee: AFFIRMED PHARMA, LLC, Conroe, TX (US)

( * ) Notice: Subject to any disclaimer, the term of this patent is extended or adjusted under 35 U.S.C. 154(b) by 735 days.

(21) Appl. No.: 17/005,118

(22) Filed: Aug. 27, 2020

(65) Prior Publication Data

US 2020/0390869 A1    Dec. 17, 2020

Related U.S. Application Data

(63) Continuation of application No. PCT/US2020/025973, filed on Mar. 31, 2020.

(60) Provisional application No. 62/832,997, filed on Apr. 12, 2019.

(51) Int. Cl.
| | |
|---|---|
| *A61K 38/48* | (2006.01) |
| *G16B 20/00* | (2019.01) |
| *A61K 9/00* | (2006.01) |
| *A61K 9/19* | (2006.01) |

(52) U.S. Cl.
CPC ........ *A61K 38/4833* (2013.01); *A61K 9/0014* (2013.01); *A61K 9/0019* (2013.01); *A61K 9/19* (2013.01); *G16B 20/00* (2019.02)

(58) Field of Classification Search
CPC .............. A61K 38/4833; A61K 9/0014; A61K 9/0019; A61K 9/19; G16B 20/00
See application file for complete search history.

(56) References Cited

U.S. PATENT DOCUMENTS

| | | | |
|---|---|---|---|
| 7,291,596 B2* | 11/2007 | Hobson | A61P 43/00 514/357 |
| 2003/0199440 A1* | 10/2003 | Dack | B41J 2/17503 514/8.1 |

FOREIGN PATENT DOCUMENTS

WO    WO-03043576 A2 *    5/2003    ............. A61K 31/00

OTHER PUBLICATIONS

Werlander and Rode. Control Strategies for Synthetic Therapeutic Peptide APIs—Part I: Analytical Consideration. BioPharm International (2014), 27(3), 40-45 (Year: 2014).*

Oyamada et al. Effect of Dimerized Thrombin Fragment TP508 on Acute Myocardial Ischemia Reperfusion Injury in Hypercholesterolemic Swine. JPET (2010), 334(2), 449-459. (Year: 2010).*

(Continued)

*Primary Examiner* — Sean C. Barron
(74) *Attorney, Agent, or Firm* — John Weatherspoon

(57) ABSTRACT

The present invention relates to rusalatide acetate compositions, formulations and dosage forms that include 23 amino acid monomer ("Monomer"), dimer ("Dimer") of two 23 amino acid Monomers, or any combination of Monomer and Dimer, wherein any ratio, proportion or percentage of Monomer and Dimer may be present in the compositions, formulations and dosage forms. The invention also broadly covers stable compositions, formulations or dosage forms that include rusalatide acetate and any pharmaceutically acceptable salts thereof.

2 Claims, 9 Drawing Sheets
Specification includes a Sequence Listing.

(56) References Cited

OTHER PUBLICATIONS

G. Hu. Understanding the Basics of Peptide and Protein Production. Bioprocess Intl. (2010), 6 page reprint. (Year: 2010).*
Hedberg et al. C ontrolled release of an osteogenic peptide from injectable biodegradable polymeric composites. Journal of Controlled Release 84 (2002) 137-150. (Year: 2002).*

* cited by examiner

System 600

610

620

630

640

650

SEQUENCE LISTING

<160> NUMBER OF SEQ ID NOS: 1

<210> SEQ ID NO 1
<211> LENGTH: 23
<212> TYPE: PRT
<213> ORGANISM: Homo sapiens

<400> SEQUENCE: 1

Ala Gly Tyr Lys Pro Asp Glu Gly Lys Arg Gly Asp Ala Cys Glu Gly
1               5                   10                  15

Asp Ser Gly Gly Pro Phe Val
            20

RUSALATIDE ACETATE COMPOSITIONS

CROSS-REFERENCE TO RELATED APPLICATIONS

This U.S. Non-Provisional Applications claims priority to PCT International Patent Application Number PCT/US2020/025973, filed Mar. 31, 2020 which claims priority to U.S. Provisional Patent Application No. 62/832,997, filed Apr. 12, 2019.

STATEMENT REGARDING SEQUENCE LISTING

The Sequence Listing associated with this U.S. patent application is provided in text format and is hereby incorporated by reference into the specification. The name of the text file containing the Sequence Listing is APharma2020RevSequenceListing.txt. The text file is 390 bytes and is being submitted electronically via EFS-Web. The Applicant confirms that this Sequence Listing does not go beyond the disclosure in this U.S. Patent Applications. The Sequence Listing submitted herewith is identical to the Sequence Listing that was filed in International PCT Patent Application Number PCT/US2020/025973.

FIELD OF THE INVENTION

The present invention relates to rusalatide acetate compositions, formulations and dosage forms that include 23 amino acid monomer ("Monomer"), dimer ("Dimer") of two 23 amino acid Monomers, or any combination of Monomer and Dimer, wherein any ratio, proportion or percentage of Monomer and Dimer may be present in the compositions, formulations and dosage forms. The invention also broadly covers stable compositions, formulations or dosage forms that include rusalatide acetate and any pharmaceutically acceptable salts thereof.

BACKGROUND

Thrombin, a multi-functional enzyme known for its blood-clotting activity, has also been reported to be an important cell-growth factor. Thrombin has been shown to promote angiogenesis, and to stimulate endothelial cell proliferation. Thrombin peptide derivatives are molecules having an amino acid sequence derived at least in part from that of thrombin, and which are active at certain thrombin receptors. Thrombin peptide derivatives are believed to activate cells by binding to a high-affinity cell-surface thrombin receptor known as the non-proteolytically-activated thrombin receptor (hereinafter "N PAR"). Compounds which stimulate NPAR are said to be thrombin receptor agonists. NPAR activation can be assayed, for example, based on the ability of molecules to stimulate cell proliferation when added to fibroblasts in the presence of submitogenic concentrations of thrombin or molecules that activate protein kinase C or compete with $^{125}$I-thrombin for high affinity binding to thrombin receptors.

Agonists of a non-proteolytically activated thrombin receptor, or NPAR agonists, which can include certain polypeptides or thrombin peptide derivatives, may also be useful in treating degenerative diseases. NPAR agonists may also be useful for stimulation of cartilage growth. In addition, certain thrombin-derived peptides may be useful in treating dermal ulcers, and may also be useful in stimulation of bone growth. In addition, certain polypeptides or thrombin peptide derivatives may also be useful in treating endothelial dysfunction. Certain polypeptides or thrombin peptide derivatives have also been shown to stimulate proliferation of endothelial cells, fibroblasts, and keratinocytes.

Thrombin peptide derivatives from amino acids 508-530 of human pro-thrombin have also been described for promoting thrombin receptor mediated cell stimulation and for their use in the treatment of wounds, and stimulation of angiogenesis. Because of their biological activity, these polypeptides show great potential as pharmaceuticals. Rusalatide acetate is one such example.

However, there has been a long-felt and unmet need for significantly improved rusalatide acetate compositions, formulations and dosage forms. The challenge in delivering therapeutic peptides in general lies in the structure of peptide molecules, which are chemically and physically unstable; prone to hydrolysis and oxidation; have a tendency to aggregate; experience a short half-life and rapid elimination; and are usually not orally available. For rusalatide acetate, these challenges have kept a potentially highly therapeutic drug from reaching practical use in the clinic since its discovery more than 30 years ago. Since the discovery of rusalatide acetate, others have completely failed to recognize the importance and significance of stabilized formulations of rusalatide acetate, and others have therefore failed to develop stabilized formulations of rusalatide acetate. The present invention meets this very significant, long-felt and unmet need for a stable rusalatide acetate dosage form for topical, injectable and oral delivery, and for any and all other rusalatide acetate dosage forms and routes of delivery or administration, thus enabling the use of rusalatide acetate for so many patients in need.

SUMMARY OF PREFERRED EMBODIMENTS

Certain embodiments of the present invention provide methods of enhancing the stability of a rusalatide acetate composition, including 23 amino acid monomer ("Monomer"), dimer ("Dimer") of two 23 amino acid Monomers, or any combination of Monomer and Dimer which may be present at any time in any ratio, proportion or percentage in the composition.

According to a preferred embodiment, the present invention contemplates a method of enhancing the stability of (i) rusalatide acetate or (ii) a rusalatide acetate composition, formulation or dosage form that includes Monomer, Dimer or any combination of Monomer and Dimer, or (iii) both (i) and (ii), the method comprising: gathering physical, non-abstract information about at least one parameter, to determine if the at least one parameter affects stability; performing a physical, non-abstract analysis of the information; and performing at least one physical, non-abstract stability optimization procedure based on the analysis such that the stability of the (i) rusalatide acetate or (ii) the rusalatide acetate composition, or (iii) both (i) and (ii) is enhanced.

According to a preferred embodiment, the present invention contemplates a method of enhancing the stability of a Monomer, comprising: gathering physical, non-abstract information about at least one parameter, to determine if the at least one parameter affects stability of the Monomer; performing a physical, non-abstract analysis of the information; and performing at least one physical, non-abstract stability optimization procedure based on the analysis such that the stability of the Monomer is enhanced.

According to a preferred embodiment, the present invention contemplates a method of enhancing the stability of a Monomer, comprising: gathering physical, non-abstract information about at least two parameters, to determine if the at least two parameters affect stability of the Monomer; performing a physical, non-abstract analysis of the information; and performing at least one physical, non-abstract stability optimization procedure based on the analysis such that the stability of the Monomer is enhanced.

According to a preferred embodiment, the present invention contemplates a method of enhancing the stability of a Monomer, comprising: gathering physical, non-abstract information about at least three parameters, to determine if the at least three parameters affect stability of the Monomer; performing a physical, non-abstract analysis of the information; and performing at least one physical, non-abstract stability optimization procedure based on the analysis such that the stability of the Monomer is enhanced.

According to a preferred embodiment, the present invention contemplates a method of enhancing the stability of a Dimer, comprising: gathering physical, non-abstract information about at least one parameter, to determine if the at least one parameter affects stability of the Dimer; performing a physical, non-abstract analysis of the information; and performing at least one physical, non-abstract stability optimization procedure based on the analysis such that the stability of the Dimer is enhanced.

According to a preferred embodiment, the present invention contemplates a method of enhancing the stability of a Dimer, comprising: gathering physical, non-abstract information about at least two parameters, to determine if the at least two parameters affect stability of the Dimer; performing a physical, non-abstract analysis of the information; and performing at least one physical, non-abstract stability optimization procedure based on the analysis such that the stability of the Dimer is enhanced.

According to a preferred embodiment, the present invention contemplates a method of enhancing the stability of a Dimer, comprising: gathering physical, non-abstract information about at least three parameters, to determine if the at least three parameters affect stability of the Dimer; performing a physical, non-abstract analysis of the information; and performing at least one physical, non-abstract stability optimization procedure based on the analysis such that the stability of the Dimer is enhanced.

According to a preferred embodiment, the present invention also contemplates a system for enhancing the stability of a Monomer, comprising: at least one physical, non-abstract computer-based instrumentation system, wherein the at least one physical, non-abstract computer-based instrumentation system is operable for collecting and processing physical, non-abstract information that is gathered with regard to at least one parameter, wherein the parameter affects stability of the Monomer; further wherein the at least one physical, non-abstract computer-based instrumentation system is operable for performing a physical, non-abstract analysis of the information about the at least one parameter; and further wherein the at least one physical, non-abstract computer-based instrumentation system is operable for performing at least one physical, non-abstract stability optimization procedure based on the analysis such that the stability of the Monomer is enhanced.

According to a preferred embodiment, the present invention also contemplates a system for enhancing the stability of a Monomer, comprising: at least one physical, non-abstract computer-based instrumentation system, wherein the at least one physical, non-abstract computer-based instrumentation system is operable for collecting and processing physical, non-abstract information that is gathered with regard to at least two parameters, wherein the parameters affect stability of the Monomer; further wherein the at least one physical, non-abstract computer-based instrumentation system is operable for performing a physical, non-abstract analysis of the information about the at least two parameters; and further wherein the at least one physical, non-abstract computer-based instrumentation system is operable for performing at least one physical, non-abstract stability optimization procedure based on the analysis such that the stability of the Monomer is enhanced.

According to a preferred embodiment, the present invention also contemplates a system for enhancing the stability of a 23 amino acid monomer ("Monomer"), comprising: at least one physical, non-abstract computer-based instrumentation system, wherein the at least one physical, non-abstract computer-based instrumentation system is operable for collecting and processing physical, non-abstract information that is gathered with regard to at least three parameters, wherein the parameters affect stability of the Monomer; further wherein the at least one physical, non-abstract computer-based instrumentation system is operable for performing a physical, non-abstract analysis of the information about the at least three parameters; and further wherein the at least one physical, non-abstract computer-based instrumentation system is operable for performing at least one physical, non-abstract stability optimization procedure based on the analysis such that the stability of the Monomer is enhanced.

According to a preferred embodiment, the present invention also contemplates a system for enhancing the stability of a dimer ("Dimer") of two 23 amino acid Monomers, comprising: at least one physical, non-abstract computer-based instrumentation system, wherein the at least one physical, non-abstract computer-based instrumentation system is operable for collecting and processing physical, non-abstract information that is gathered with regard to at least one parameter, wherein the parameter affects stability of the Dimer; further wherein the at least one physical, non-abstract computer-based instrumentation system is operable for performing a physical, non-abstract analysis of the information about the at least one parameter; and further wherein the at least one physical, non-abstract computer-based instrumentation system is operable for performing at least one physical, non-abstract stability optimization procedure based on the analysis such that the stability of the Dimer is enhanced.

According to a preferred embodiment, the present invention also contemplates a system for enhancing the stability of a Dimer, comprising: at least one physical, non-abstract computer-based instrumentation system, wherein the at least one physical, non-abstract computer-based instrumentation system is operable for collecting and processing physical, non-abstract information that is gathered with regard to at least two parameters, wherein the parameters affect stability of the Dimer; further wherein the at least one physical, non-abstract computer-based instrumentation system is operable for performing a physical, non-abstract analysis of the information about the at least two parameters; and further wherein the at least one physical, non-abstract computer-based instrumentation system is operable for performing at least one physical, non-abstract stability optimization procedure based on the analysis such that the stability of the Dimer is enhanced.

According to a preferred embodiment, the present invention also contemplates a system for enhancing the stability of a Dimer, comprising: at least one physical, non-abstract computer-based instrumentation system, wherein the at least one physical, non-abstract computer-based instrumentation system is operable for collecting and processing physical, non-abstract information that is gathered with regard to at least three parameters, wherein the parameters affect stability of the Dimer; further wherein the at least one physical, non-abstract computer-based instrumentation system is operable for performing a physical, non-abstract analysis of the information about the at least three parameters; and further wherein the at least one physical, non-abstract computer-based instrumentation system is operable for performing at least one physical, non-abstract stability optimization procedure based on the analysis such that the stability of the Dimer is enhanced.

According to a preferred embodiment, the present invention also contemplates a system for enhancing the stability of a rusalatide acetate composition that includes 23 amino acid monomer ("Monomer"), dimer ("Dimer") of two 23 amino acid Monomers, or any combination of Monomer and Dimer, wherein any ratio, proportion or percentage of Monomer and Dimer may be present in the composition, the system comprising at least one physical, non-abstract computer-based instrumentation system, wherein the operations of the at least one physical, non-abstract computer-based instrumentation system includes operation of any suitable artificial intelligence (A.I.) or machine-learning technology, and further wherein the at least one physical, non-abstract computer-based instrumentation system comprises at least one physical component of computer hardware architecture or microarchitecture which is essential and required to specifically perform the methods and operations of the present invention as described herein. The operations of the at least one physical, non-abstract computer-based instrumentation system include, but are not limited to:

(i) collecting and processing physical, non-abstract information that is gathered with regard to at least one parameter, wherein the parameter affects stability of the Monomer, the Dimer, the composition, or any combination thereof;

(ii) performing a physical, non-abstract analysis of the information about the at least one parameter; and (iii) performing at least one physical, non-abstract stability optimization procedure based on the analysis such that the stability of the Monomer, the Dimer, the composition, or any combination thereof, is enhanced.

According to yet another preferred embodiment, the present invention also contemplates a system for enhancing the stability of a Monomer, comprising at least one physical, non-abstract computer-based instrumentation system, wherein the operations of the at least one physical, non-abstract computer-based instrumentation system includes operation of any suitable artificial intelligence (A.I.) or machine-learning technology, and further wherein the at least one physical, non-abstract computer-based instrumentation system comprises at least one physical component of computer hardware architecture or microarchitecture which is essential and required to specifically perform the methods and operations of the present invention as described herein. The operations of the at least one physical, non-abstract computer-based instrumentation system include, but are not limited to:

(i) collecting and processing physical, non-abstract information that is gathered with regard to at least one parameter, wherein the parameter affects stability of the Monomer;

(ii) performing a physical, non-abstract analysis of the information about the at least one parameter; and (iii) performing at least one physical, non-abstract stability optimization procedure based on the analysis such that the stability of the Monomer is enhanced.

As described herein, according to preferred embodiments, the at least one physical, non-abstract computer-based instrumentation system comprises at least one physical component of computer hardware, architecture or microarchitecture which is essential and required to specifically perform the methods and operations of the present invention. The methods and operations of the present invention that require at least one physical, non-abstract computer-based instrumentation system can preferably be implemented using any type of suitable software system or high-level programming languages and any type of computer hardware system, network system, or other platform. By way of non-limiting example, examples of high-level programming languages include, but are not limited to, C, C++, Pascal, Perl, Cobol, Java, and Python.

As used herein, the term "computer hardware" is preferably intended to include all the necessary components of a computer system that are required to "run" or execute a source program, and that allow someone to use the computer. By way of non-limiting example, the hardware components include, but are not limited to, a power supply, motherboard, hard disk, graphics card, random access memory (RAM), and other hardware components. Additional hardware components can include, for instance, a keyboard, mouse, speakers, etc. It is also contemplated that the methods of the present invention can be implemented by operation of any type of computer system that includes computer components including but not limited to a processor, memory storage devices for the processor, connected display devices and input devices. Furthermore, the methods of the present invention can also be implemented by operation of computer components in a heterogeneous distributed computing environment, including for example one or more remote file servers, computer servers, and/or memory storage devices. Each of these distributed computing components is accessible by the processor via a communication network, which may include, but is not limited to, the Internet.

It should be appreciated that the present invention can be implemented in numerous ways, including as a process, an apparatus, a system, a device, a method, a computer readable medium, or any combination thereof. Several inventive embodiments of the present invention are described herein.

According to another preferred embodiment, the present invention also contemplates a system for enhancing the stability of a Monomer, as herein described, wherein the operations of the at least one physical, non-abstract computer-based instrumentation system include, but are not limited to:

(i) collecting and processing physical, non-abstract information that is gathered with regard to at least three parameters, wherein each of the three parameters affects stability of the Monomer;

(ii) performing a physical, non-abstract analysis of the information about the at least three parameters; and (iii) performing at least one physical, non-abstract stability optimization procedure based on the analysis such that the stability of the Monomer is enhanced.

According to another preferred embodiment, the present invention also contemplates a system for enhancing the stability of a Dimer, comprising at least one physical, non-abstract computer-based instrumentation system, wherein the operations of the at least one physical, non-abstract computer-based instrumentation system includes operation of any suitable artificial intelligence (A.I.) or machine-learning technology, and further wherein the at least one physical, non-abstract computer-based instrumentation system comprises at least one physical component of computer hardware, architecture or microarchitecture which is essential and required to specifically perform the methods and operations of the present invention as described herein. The operations of the at least one physical, non-abstract computer-based instrumentation system include, but are not limited to:
  (i) collecting and processing physical, non-abstract information that is gathered with regard to at least one parameter, wherein the parameter affects stability of the Dimer;
  (ii) performing a physical, non-abstract analysis of the information about the at least one parameter; and
  (iii) performing at least one physical, non-abstract stability optimization procedure based on the analysis such that the stability of the Dimer is enhanced.

According to another preferred embodiment, the present invention also contemplates a system for enhancing the stability of a Dimer, as herein described, wherein the operations of the at least one physical, non-abstract computer-based instrumentation system include, but are not limited to:
  (i) collecting and processing physical, non-abstract information that is gathered with regard to at least five parameters, wherein each of the five parameters affects stability of the Dimer;
  (ii) performing a physical, non-abstract analysis of the information about the at least five parameters; and
  (iii) performing at least one physical, non-abstract stability optimization procedure based on the analysis such that the stability of the Dimer is enhanced.

According to another embodiment, the present invention provides a method of enhancing the stability of a rusalatide acetate composition that includes Monomer, Dimer, or any combination of Monomer and Dimer, wherein any ratio, proportion or percentage of Monomer and Dimer may be present in the composition, wherein the method comprises:
  (i) optimizing a first parameter during a process of preparing the composition;
  (ii) optimizing a second parameter during the process of preparing the composition; and
  (iii) optimizing a third parameter during the process of preparing the composition, wherein optimizing the first, second and third parameters results in enhanced stability of the composition.

According to another preferred embodiment, the present invention also contemplates rusalatide acetate compositions, formulations and dosage forms that include Monomer, Dimer, or any combination thereof, wherein any ratio, proportion or percentage of Monomer and Dimer may be present in the compositions, formulations and dosage forms, and further wherein the stability of the rusalatide acetate formulation, pharmaceutical composition or dosage form is enhanced according to the methods and systems of the present invention.

According to another preferred embodiment, the present invention also contemplates methods of treating a subject in need of treatment with a rusalatide acetate composition, formulation or dosage form that includes Monomer, Dimer, or any combination of Monomer and Dimer, wherein any ratio, proportion or percentage of Monomer and Dimer may be present in the composition, formulation or dosage form, and further wherein the stability of the composition, formulation or dosage form is enhanced according to the methods and systems of the present invention.

According to another preferred embodiment, the present invention also contemplates pharmaceutical compositions comprising Monomer, wherein the stability of the Monomer is enhanced according to the methods and systems of the present invention.

According to another preferred embodiment, the present invention also contemplates methods of treating a subject in need of treatment with Monomer, wherein the stability of the Monomer is enhanced according to the methods and systems of the present invention.

According to another preferred embodiment, the present invention also contemplates pharmaceutical compositions comprising Dimer, wherein the stability of the Dimer is enhanced according to the methods and systems of the present invention.

According to another preferred embodiment, the present invention also contemplates methods of treating a subject in need of treatment with Dimer, wherein the stability of the Dimer is enhanced according to the methods and systems of the present invention.

According to a preferred embodiment, the present invention also contemplates a stabilized form of rusalatide acetate 23 amino acid monomer ("Monomer"), wherein the stability is enhanced using peptidomimetic insertions in the polypeptide chain thereof.

According to a preferred embodiment, the present invention also contemplates a stable, drugable form of rusalatide acetate 23 amino acid monomer ("Monomer"), wherein the stable drugable form is a crystalline form.

According to a preferred embodiment, the present invention also contemplates polymorphic crystalline forms of rusalatide acetate 23 amino acid monomer ("Monomer"), the Monomer being capable of existing in several different crystalline forms.

According to a preferred embodiment, the present invention also contemplates a stabilized form of Dimer, wherein the stability is enhanced using peptidomimetic insertions in the polypeptide chain thereof.

According to a preferred embodiment, the present invention also contemplates a stable, drugable form of Dimer, wherein the stable drugable form is a crystalline form.

According to a preferred embodiment, the present invention also contemplates polymorphic crystalline forms of Dimer, the Dimer being capable of existing in several different crystalline forms.

In one preferred embodiment, the present invention contemplates a stable polypeptide composition ("composition W") comprising:
  (a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), the polypeptide having been synthesized and purified according to Good Manufacturing Practice (GMP) requirements, wherein the composition is essentially free of reactive oxygen species, endotoxins, organic solvents, degradation impurities, and redox-active transition metal impurities,
  and
  (b) at least one pharmaceutically acceptable excipient,
  wherein the composition is prepared under aseptic conditions, stored with a hygroscopic agent, further wherein the composition is stable, protected from light, and further wherein the composition is packaged and sealed after exposure to a non-reactive, anhydrous purging agent,
  further wherein stability of the composition is determined based at least on a combination of forced degradation analysis, analysis of water content in the composition, counterion quantification analysis, and bioburden testing of the composition.

In yet another embodiment, the present invention contemplates a rusalatide acetate composition as described herein, wherein the polypeptide is lyophilized.

In yet another embodiment, the present invention contemplates a rusalatide acetate composition, as described herein, wherein the purging agent is nitrogen.

In yet another embodiment, the present invention contemplates a rusalatide acetate composition, as described herein, further wherein the composition is formulated for sterile administration.

In yet another embodiment, the present invention contemplates a rusalatide acetate composition, as described herein, wherein the purging agent is argon.

In yet another embodiment, the present invention contemplates a rusalatide acetate composition, as described herein, comprising an antioxidant.

In yet another preferred embodiment, the present invention contemplates a rusalatide acetate composition ("composition X") comprising:
(a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), wherein the polypeptide is synthesized and purified according to Good Manufacturing Practice (GMP) requirements, further wherein the composition is essentially free of reactive oxygen species, endotoxins, organic solvents, degradation impurities, and redox-active transition metal impurities,
(b) a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond, and
(c) an aqueous carrier,
further wherein the composition is prepared under aseptic conditions.
further wherein stability of the composition is determined based at least on a combination of forced degradation analysis, counterion quantification analysis, and bioburden testing of the composition.

In yet another embodiment, the present invention contemplates "composition X" as described above, wherein the composition is at least 90 percent free of reactive oxygen species, endotoxins, organic solvents, degradation impurities, and redox-active transition metal impurities.

In yet another embodiment, the present invention contemplates "composition X" as described above, wherein the composition is formulated for sterile administration.

In yet another embodiment, the present invention contemplates "composition X" as described above, wherein the composition is formulated as a single use liquid dosage form.

In yet another embodiment, the present invention contemplates "composition X" as described above, comprising an antioxidant.

In yet another preferred embodiment, the present invention contemplates a stable polypeptide composition ("composition Y") comprising:
(a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), the polypeptide having been synthesized and purified according to Good Manufacturing Practice (GMP) requirements, wherein the composition is essentially free of reactive oxygen species, endotoxins, organic solvents, degradation impurities, and redox-active transition metal impurities,
(b) a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond, and
(c) at least one pharmaceutically acceptable excipient,
wherein the composition is stable, protected from light, and prepared under aseptic conditions,
further wherein stability of the composition is determined based at least on a combination of forced degradation analysis, analysis of water content in the composition, counterion quantification analysis, and bioburden testing of the composition.

In yet another embodiment, the present invention contemplates "composition Y" as described above, wherein the composition is at least 90 percent free of reactive oxygen species, endotoxins, organic solvents, degradation impurities, and redox-active transition metal impurities.

In yet another embodiment, the present invention contemplates "composition Y" as described above, wherein the composition is formulated for topical administration.

In yet another embodiment, the present invention contemplates "composition Y" as described above, wherein the composition is formulated for sterile administration.

In yet another embodiment, the present invention contemplates "composition Y" as described above, wherein the composition is formulated for sterile, injectable delivery.

In yet another embodiment, the present invention contemplates "composition Y" as described above, comprising an antioxidant.

In yet another embodiment, the present invention contemplates "composition Y" as described above, wherein the composition is formulated as a single use liquid dosage form.

The present invention also contemplates rusalatide acetate compositions, formulations and dosage forms, including a 23 amino acid monomer ("Monomer), a dimer ("Dimer") of two 23 amino acid monomers, or any combination of Monomer and Dimer which may be present at any time in any ratio, proportion or percentage of the rusalatide acetate compositions, formulations and dosage forms, further wherein the compositions, formulations and dosage forms are at least 70 percent free of reactive oxygen species, endotoxins, organic solvents, degradation impurities, and redox-active transition metal impurities.

The present invention also contemplates rusalatide acetate compositions, formulations and dosage forms, including Monomer, Dimer, or any combination of Monomer and Dimer which may be present at any time in any ratio, proportion or percentage of the rusalatide acetate compositions, formulations and dosage forms, wherein the compositions, formulations and dosage forms are at least 75 percent free of reactive oxygen species, endotoxins, organic solvents, degradation impurities, and redox-active transition metal impurities.

The present invention also contemplates rusalatide acetate compositions, formulations and dosage forms, including Monomer, Dimer, or any combination of Monomer and Dimer which may be present at any time in any ratio, proportion or percentage of the rusalatide acetate compositions, formulations and dosage forms, wherein the compositions, formulations and dosage forms are at least 80 percent free of reactive oxygen species, endotoxins, organic solvents, degradation impurities, and redox-active transition metal impurities.

The present invention also contemplates rusalatide acetate compositions, formulations and dosage forms, including Monomer, Dimer, or any combination of Monomer and Dimer which may be present at any time in any ratio, proportion or percentage of the rusalatide acetate compositions, formulations and dosage forms, wherein the compositions, formulations and dosage forms are at least 85 percent free of reactive oxygen species, endotoxins, organic solvents, degradation impurities, and redox-active transition metal impurities.

The present invention also contemplates rusalatide acetate compositions, formulations and dosage forms, including Monomer, Dimer, or any combination of Monomer and Dimer which may be present at any time in any ratio, proportion or percentage of the rusalatide acetate compositions, formulations and dosage forms, wherein the compositions, formulations and dosage forms are at least 90 percent free of reactive oxygen species, endotoxins, organic solvents, degradation impurities, and redox-active transition metal impurities.

The present invention also contemplates rusalatide acetate compositions, formulations and dosage forms, including Monomer, Dimer, or any combination of Monomer and Dimer which may be present at any time in any ratio, proportion or percentage of the rusalatide acetate compositions, formulations and dosage forms, wherein the compositions, formulations and dosage forms are at least 95 percent free of reactive oxygen species, endotoxins, organic solvents, degradation impurities, and redox-active transition metal impurities.

The present invention also contemplates rusalatide acetate compositions, formulations and dosage forms, including Monomer, Dimer, or any combination of Monomer and Dimer which may be present at any time in any ratio, proportion or percentage of the rusalatide acetate compositions, formulations and dosage forms, wherein the compositions, formulations and dosage forms are at least 98 percent free of reactive oxygen species, endotoxins, organic solvents, degradation impurities, and redox-active transition metal impurities.

The present invention also contemplates rusalatide acetate compositions, formulations and dosage forms, including Monomer, Dimer, or any combination of Monomer and Dimer which may be present at any time in any ratio, proportion or percentage of the rusalatide acetate compositions, formulations and dosage forms, wherein the compositions, formulations and dosage forms are at least 99 percent free of reactive oxygen species, endotoxins, organic solvents, degradation impurities, and redox-active transition metal impurities.

The present invention also contemplates a rusalatide acetate composition comprising:
- (a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), wherein the polypeptide is synthesized and purified according to Good Manufacturing Practice (GMP) requirements, further wherein the composition is at least 90 percent free of reactive oxygen species, endotoxins, organic solvents, degradation impurities, and redox-active transition metal impurities, and
- (b) at least one pharmaceutically acceptable excipient, wherein the composition is prepared under aseptic conditions, stored with a hygroscopic agent, further wherein the composition is stable, protected from light, and further wherein the composition is packaged and sealed after exposure to a non-reactive, anhydrous purging agent,
- further wherein stability of the composition is determined based at least on a combination of forced degradation analysis, analysis of water content in the composition, counterion quantification analysis, and bioburden testing of the composition.

The present invention also contemplates a rusalatide acetate composition comprising:
- (a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), wherein the polypeptide is synthesized and purified according to Good Manufacturing Practice (GMP) requirements, further wherein the composition is at least 90 percent free of reactive oxygen species, endotoxins, organic solvents, degradation impurities, and redox-active transition metal impurities,
- (b) a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond, and
- (c) an aqueous carrier,
- further wherein the composition is prepared under aseptic conditions.
- further wherein stability of the composition is determined based at least on a combination of forced degradation analysis, counterion quantification analysis, and bioburden testing of the composition.

The present invention also contemplates a rusalatide acetate composition comprising:
- (a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), wherein the polypeptide is synthesized and purified according to Good Manufacturing Practice (GMP) requirements, further wherein the composition is at least 90 percent free of reactive oxygen species, endotoxins, organic solvents, degradation impurities, and redox-active transition metal impurities,
- (b) a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond, and
- (c) at least one pharmaceutically acceptable excipient,
- wherein the composition is stable, protected from light, and prepared under aseptic conditions,
- further wherein stability of the composition is determined based at least on a combination of forced degradation analysis, analysis of water content in the composition, counterion quantification analysis, and bioburden testing of the composition.

In yet another embodiment, the present invention contemplates a method of enhancing the stability of a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), the method comprising:
- simultaneously gathering information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide, performing an analysis of the information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide; and performing at least one stability optimization procedure based on the analysis such that the stability of the polypeptide is enhanced.

In yet another embodiment, the present invention contemplates a method of enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond, the method comprising:

simultaneously gathering information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer, performing an analysis of the information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer; and performing at least one stability optimization procedure based on the analysis such that the stability of the peptide dimer is enhanced.

According to another preferred embodiment, the present invention provides a system for enhancing the stability of a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), the system comprising components for:

simultaneously gathering information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide, performing an analysis of the information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide; and performing at least one stability optimization procedure based on the analysis such that the stability of the polypeptide is enhanced, the system further comprising at least one processor and at least one memory storage device for storing the information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide.

According to another preferred embodiment, the present invention provides a system for enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond, the system comprising components for:

simultaneously gathering information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer, performing an analysis of the information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer; and performing at least one stability optimization procedure based on the analysis such that the stability of the peptide dimer is enhanced, the system further comprising at least one processor and at least one memory storage device for storing the information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer.

Additional representative embodiments of the present invention are discussed in more detail herein. It is to be understood that these representative embodiments do not limit the scope of the present invention in any way. The representative embodiments described herein are provided as examples to illustrate the broad scope of the present invention.

BRIEF DESCRIPTION OF THE FIGURES

These and other aspects and advantages of the invention will become apparent and more readily appreciated from the following description, taken in conjunction with the accompanying figures.

FIG. 6 is a schematic diagram depicting a representative system for enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond.

Figure 1A:
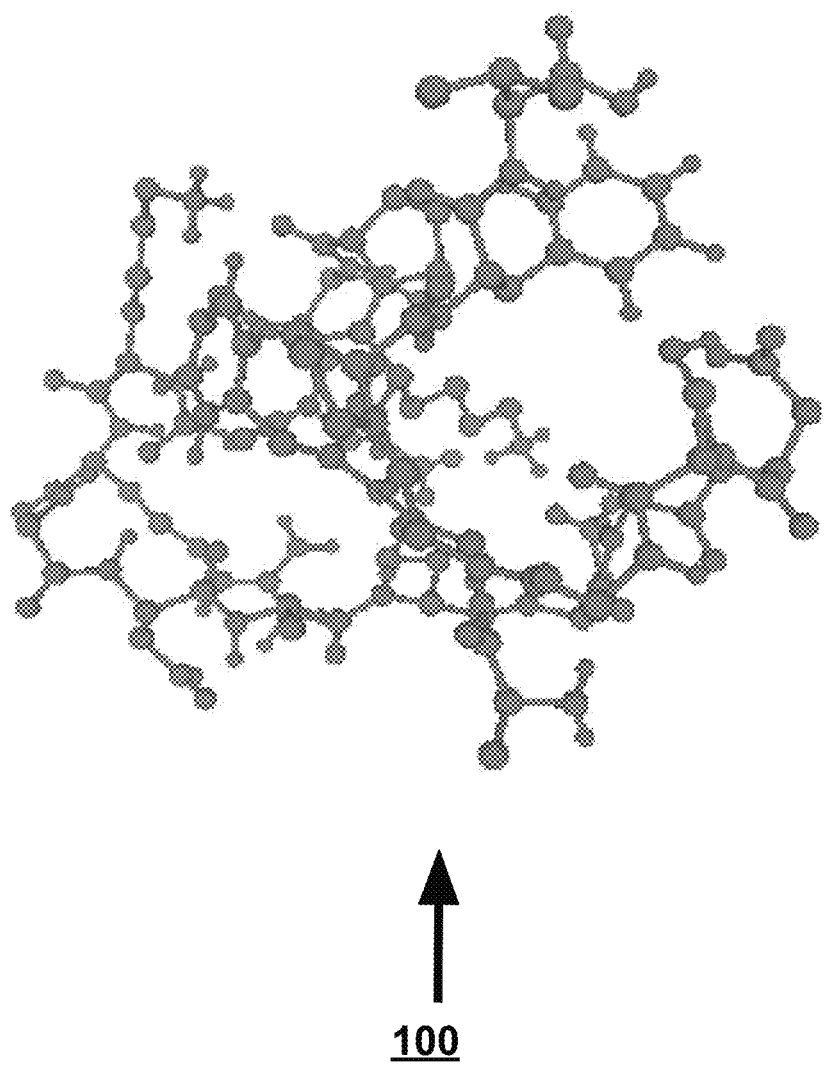
FIG. 1A depicts the Monomer in one 3D orientation.

These figures illustrate certain non-limiting embodiments of the present invention. These non-limiting embodiments do not limit the scope of the present invention in any way.

DESCRIPTION OF PREFERRED EMBODIMENTS

Although the detailed description herein contains many details for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the broad scope of the present invention. While certain embodiments are described herein, it is to be understood that there is no intent to limit the scope to the embodiments disclosed herein. On the contrary, the intent is to cover all alternatives, modifications, and equivalents within the broad scope of the present invention.

As used herein, the phrases "in one embodiment," "in various embodiments," "in some embodiments," and the like are used repeatedly. Such phrases do not necessarily refer to the same embodiment.

Unless defined otherwise, all technical and scientific terms used herein have the same meaning as commonly understood by one of ordinary skill in the art.

A "subject" is preferably a human, but can also be a non-human animal in need of treatment with a thrombin receptor agonist or an NPAR agonist. Such animals can include, but are not limited to, companion animals (e.g., dogs, cats, and the like), farm animals (e.g., cows, pigs, horses and the like) and laboratory animals (e.g., rats, mice, guinea pigs and the like). It is contemplated that the rusalatide acetate formulations, pharmaceutical compositions and dosage forms of the present invention can be used for human clinical uses and also non-human, veterinary uses.

Subjects "in need of treatment" with a rusalatide acetate formulation, pharmaceutical composition or dosage form, in accordance with the present invention, include subjects with diseases or conditions that can be treated with a rusalatide acetate formulation, pharmaceutical composition or dosage form to achieve a beneficial therapeutic or prophylactic result. A beneficial outcome can include, for example, a decrease in the severity of symptoms or a delay in the onset of symptoms, increased longevity, more rapid or more complete resolution of the disease or condition, or any combination thereof. For example, a subject in need of treatment may require bone growth, angiogenesis, or wound healing to achieve a beneficial outcome.

The terms "stable", "stable pharmaceutical composition", "stability" and "stabilized", as used herein, and including any other variations of the term "stable", are all intended to broadly refer to a state or condition in which there are no material changes or significant changes in chemical or physical characteristics and potency of a rusalatide acetate composition, formulation or dosage form that includes 23 amino acid monomer ("Monomer"), dimer ("Dimer") of two 23 amino acid Monomers, or any combination of Monomer and Dimer. Stability can be measured, for example, over a certain period of time. A "stable" or "stabilized" rusalatide acetate composition, formulation or dosage form can thus include, for example, a composition, formulation or dosage form in which there are no material changes or significant changes in chemical or physical characteristics and potency over time, based on accurate and reliable analytical measurements.

Also, whenever there is a reference or discussion to "stable", "stability" or "stabilized" it is also contemplated that any change in stability of (i) rusalatide acetate or (ii) a rusalatide acetate composition, formulation or dosage form that includes Monomer, Dimer or any combination of Monomer and Dimer, or (iii) both (i) and (ii), may also produce corresponding changes in the biologic or pharmaceutical activity of said (i) rusalatide acetate or (ii) rusalatide acetate composition, formulation or dosage form that includes Monomer, Dimer or any combination of Monomer and Dimer, or (iii) both (i) and (ii). For example, a reduction or loss in the stability of Monomer may also produce a corresponding reduction or loss in the biologic or pharmaceutical activity of said Monomer.

In one non-limiting example of the invention, the stable pharmaceutical compositions of the present invention meet all regulatory requirements including the requirements of the U.S. FDA, including for example requirements in which a stable pharmaceutical product deteriorates no more than about ten percent (10%) over a span of two years.

Throughout the detailed description herein, with reference to enhancing the stability of rusalatide acetate, it is also contemplated that steps can be taken to optimize and enhance the thermodynamic and kinetic stability of rusalatide acetate in rusalatide acetate pharmaceutical compositions, dosage forms and formulations.

As used herein, the term "potency" is intended to refer to a measure of the activity of rusalatide acetate expressed in terms of the amount of rusalatide acetate required to produce an effect of a given intensity (i.e., a pharmacologic effect or biologic effect, after rusalatide acetate is administered to a subject).

As described herein, rusalatide acetate is one example of a thrombin peptide derivative or polypeptide. Rusalatide acetate is a synthetic 23-amino acid peptide corresponding to amino acids 508 through 530 of human prothrombin. rusalatide acetate has multiple potential clinical uses including, for example, treatment of diabetic foot ulcers, wound healing, promotion of bone and cartilage formation, promoting fracture repair; promoting angiogenesis; and many other potential clinical uses.

Rusalatide Acetate

Rusalatide acetate is identified by the 23 amino acid Monomer sequence ("Monomer"; herein identified as SEQ ID NO: 1) described and shown below. Rusalatide acetate functions as an NPAR agonist (wherein NPAR refers to "non-proteolytically-activated thrombin receptor"). It is to be understood that rusalatide acetate can also be referred to as TP508. Therefore, in accordance with the present invention, it is to be clearly understood that the term "TP508" can be used interchangeably with the term "rusalatide acetate". Thus, for example, it is to be understood that "a pharmaceutical composition comprising TP508" can be used interchangeably with "a pharmaceutical composition comprising rusalatide acetate".

As used throughout this description, it is to be understood that the term "rusalatide acetate composition, formulation or dosage form" as used herein is intended to broadly include any safe and effective rusalatide acetate composition, formulation or dosage form that includes 23 amino acid monomer ("Monomer"; herein identified as SEQ ID NO: 1), dimer ("Dimer") of two 23 amino acid Monomers, or any combination of Monomer and Dimer, wherein any ratio, proportion or percentage of Monomer and Dimer may be present in the composition, formulation or dosage form. The invention also broadly covers stable compositions, formulations or dosage forms that include rusalatide acetate and any pharmaceutically acceptable salts thereof.

The detailed description of the (I) 23 amino acid monomer ("Monomer"; herein identified as SEQ ID NO: 1) and (II) dimer ("Dimer") of two 23 amino acid Monomers is set forth below.

23 Amino Acid Monomer

The 23-amino acid monomer peptide ("Monomer") has the following amino acid sequence and primary structure:
Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val The above sequence for the 23 amino acid monomer peptide is Sequence ID Number 1 (SEQ ID NO: 1), which is shown below and in the Sequence Listing in this disclosure.

(SEQ ID NO: 1)
AGYKPDEGKRGDACEGDSGGPFV

The 23 amino acid sequence for the monomer can also be depicted based on the one-letter amino acid code, shown above.

For the sake of clarity, the one-letter amino acid code designations and the three-letter amino acid code designations are provided below:

A represents Alanine (ALA)
R represents Arginine (ARG)
N represents Asparagine (ASN)
D represents Aspartic Acid (ASP)
C represents Cysteine (CYS)
E represents Glutamic Acid (GLU)
Q represents Glutamine (GLN)
G represents Glycine (GLY)
H represents Histidine (HIS)
I represents Isoleucine (ILE)
L represents Leucine (LEU)
K represents Lysine (LYS)
M represents Methionine (MET)
F represents Phenylalanine (PHE)
P represents Proline (PRO)
S represents Serine (SER)
T represents Threonine (THR)
W represents Tryptophan (TRP)
Y represents Tyrosine (TYR)
V represents Valine (VAL)

Also, for simplicity and clarity, the 23 amino acid monomer described herein (SEQ ID NO: 1) may also be referred to herein as "Monomer" (i.e., the capitalized word "Monomer" is used throughout this description). In other words, "Monomer" in this disclosure is intended to refer only to the 23 amino acid monomer described herein (SEQ ID NO: 1).

Figure 7:
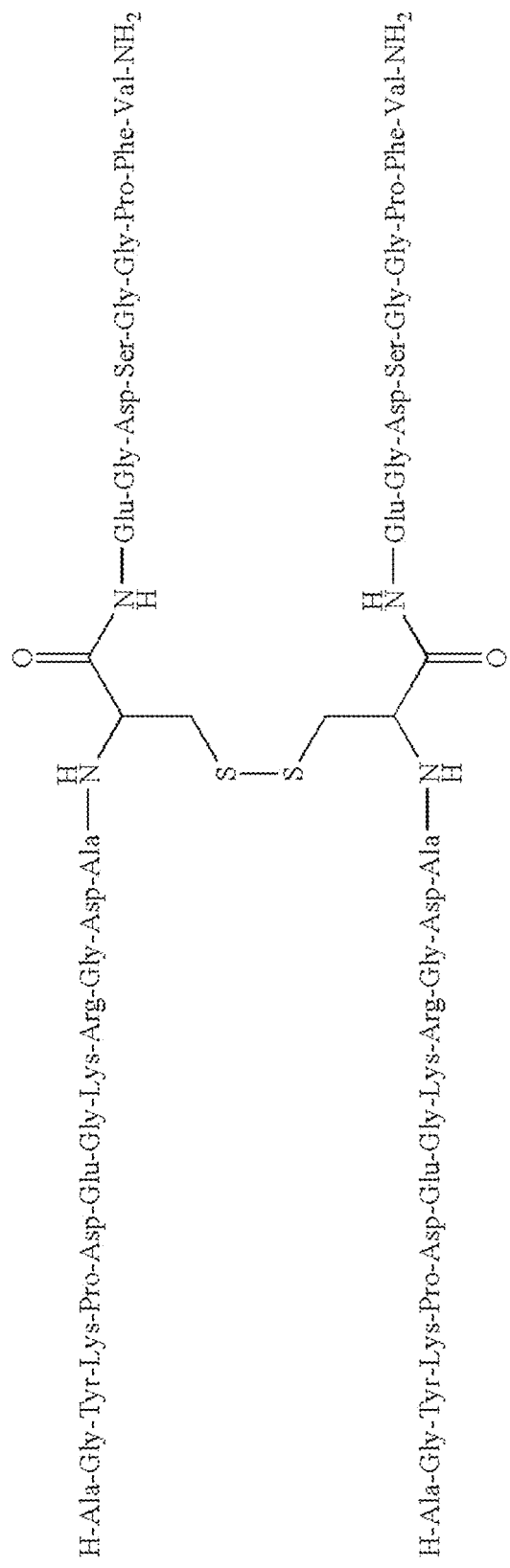
FIG. 7 shows a structural formula for the Dimer.

In a preferred embodiment, a synthetic form of rusalatide acetate can be represented as follows:
H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$
Dimer It has been found that 23 amino acid monomer peptides (or "Monomers") can dimerize spontaneously in a saline solution, which is just one example of dimerization. Because each 23 amino acid Monomer contains a cysteine residue, two 23 amino acid Monomers are capable of forming a dimer (the capitalized term "Dimer" is used throughout this description) via formation of a disulfide bond. The structural formula for the dimer ("Dimer") of two 23 amino acid Monomers is shown in FIG. 7.

Again, for simplicity and clarity, a dimer of two 23 amino acid Monomers may also be referred to throughout this description as a "Dimer" (i.e., the capitalized word "Dimer").

Other representative embodiments of the invention are described herein.

Rusalatide acetate, or its pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)- for amino acids. In preferred embodiments of the present invention, the monomeric or dimeric form of rusalatide acetate are present in the natural (L) form. The present invention is intended to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by other methods, for example by formation of diastereoisomeric salts which may then be separated by crystallization, gas-liquid or liquid chromatography, selective reaction of one enantiomer with an enantiomer specific reagent. It will also be appreciated that where the desired enantiomer is converted into another chemical entity by a separation technique, an additional step is then required to form the desired enantiomeric form. Alternatively, specific enantiomers may be synthesized by asymmetric synthesis using optically active reagents, substrates, catalysts, or solvents or by converting one enantiomer to another by asymmetric transformation.

Certain rusalatide acetate isomers may exist as a mix of epimers. Epimers means diastereoisomers that have the opposite configuration at only one of two or more stereogenic centres present in the respective compound.

Certain rusalatide acetate isomers may exist in Zwitterionic form and the present invention includes Zwitterionic forms of these isomers and mixtures thereof.

Broadly, the present invention contemplates rusalatide acetate compositions, formulations and dosage forms that include 23 amino acid monomer ("Monomer"), dimer ("Dimer") of two 23 amino acid Monomers, or any combination of Monomer and Dimer wherein any ratio, proportion or percentage of Monomer and Dimer may be present in the compositions, formulations and dosage forms.

Throughout this description, it is contemplated that rusalatide acetate compositions, formulations and dosage forms can include for example any possible ratio, proportion or percentage of 23 amino acid monomer ("Monomer"), dimer ("Dimer") of two 23 amino acid Monomers, or any combination of Monomer and Dimer, including but not limited to 100% Monomer, 100% Dimer, or any other possible ratio, proportion or percentage of the Monomer and Dimer.

According to still other preferred embodiments, wherein a pharmaceutical composition comprises a certain percentage of Monomer and a certain percentage of Dimer, and wherein the stability of both the Monomer and the Dimer is enhanced according to the methods and systems of the present invention, it is to be understood that the Monomer and the Dimer can be present in any proportion or ratio.

According to a non-limiting example, the total rusalatide acetate present in a pharmaceutical composition or formulation can include about 100% Monomer.

According to another non-limiting example, the total rusalatide acetate present in a pharmaceutical composition or formulation can include about 100% Dimer.

According to yet another non-limiting example, the total rusalatide acetate present in a pharmaceutical composition or formulation includes about 1% Monomer and about 99% Dimer (i.e., proportions of about 1% monomer and about 99% dimer), wherein the stability of both the Monomer and the Dimer is enhanced according to the methods and systems of the present invention.

According to another non-limiting example, the total rusalatide acetate present in a pharmaceutical composition or formulation includes about 2% Monomer and about 98% Dimer (i.e., proportions of about 2% monomer and about 98% dimer), wherein the stability of both the Monomer and the Dimer is enhanced according to the methods and systems of the present invention.

According to another non-limiting example, the total rusalatide acetate present in a pharmaceutical composition or formulation includes about 3% Monomer and about 97% Dimer (i.e., proportions of about 3% monomer and about 97% dimer), wherein the stability of both the Monomer and the Dimer is enhanced according to the methods and systems of the present invention.

According to other non-limiting examples, it is to be understood that the present invention also contemplates that the total rusalatide acetate present in a pharmaceutical composition or formulation can include Monomer and Dimer in the following representative, non-limiting proportions, which are provided by way of illustration and which do not limit the scope of the invention in any way, and wherein the stability of both the Monomer and the Dimer is enhanced according to the methods and systems of the present invention:

proportions of about 4% Monomer and about 96% Dimer;
proportions of about 5% Monomer and about 95% Dimer;
proportions of about 6% Monomer and about 94% Dimer;
proportions of about 7% Monomer and about 93% Dimer;
proportions of about 8% Monomer and about 92% Dimer;
proportions of about 9% Monomer and about 91% Dimer;
proportions of about 10% Monomer and about 90% Dimer;
proportions of about 11% Monomer and about 89% Dimer;
proportions of about 12% Monomer and about 88% Dimer;
proportions of about 13% Monomer and about 87% Dimer;
proportions of about 14% Monomer and about 86% Dimer;
proportions of about 15% Monomer and about 85% Dimer;
proportions of about 16% Monomer and about 84% Dimer;
proportions of about 17% Monomer and about 83% Dimer;
proportions of about 18% Monomer and about 82% Dimer;
proportions of about 19% Monomer and about 81% Dimer;
proportions of about 20% Monomer and about 80% Dimer;
proportions of about 21% Monomer and about 79% Dimer;
proportions of about 22% Monomer and about 78% Dimer;
proportions of about 23% Monomer and about 77% Dimer;
proportions of about 24% Monomer and about 76% Dimer;
proportions of about 25% Monomer and about 75% Dimer;
proportions of about 26% Monomer and about 74% Dimer;
proportions of about 27% Monomer and about 73% Dimer;
proportions of about 28% Monomer and about 72% Dimer;
proportions of about 29% Monomer and about 71% Dimer;
proportions of about 30% Monomer and about 70% Dimer;
proportions of about 31% Monomer and about 69% Dimer;
proportions of about 32% Monomer and about 68% Dimer;
proportions of about 33% Monomer and about 67% Dimer;
proportions of about 34% Monomer and about 66% Dimer;
proportions of about 35% Monomer and about 65% Dimer;
proportions of about 36% Monomer and about 64% Dimer;
proportions of about 37% Monomer and about 63% Dimer;
proportions of about 38% Monomer and about 62% Dimer;
proportions of about 39% Monomer and about 61% Dimer;
proportions of about 40% Monomer and about 60% Dimer;
proportions of about 41% Monomer and about 59% Dimer;
proportions of about 42% Monomer and about 58% Dimer;
proportions of about 43% Monomer and about 57% Dimer;

proportions of about 44% Monomer and about 56% Dimer;
proportions of about 45% Monomer and about 55% Dimer;
proportions of about 46% Monomer and about 54% Dimer;
proportions of about 47% Monomer and about 53% Dimer;
proportions of about 48% Monomer and about 52% Dimer;
proportions of about 49% Monomer and about 51% Dimer;
proportions of about 50% Monomer and about 50% Dimer;
proportions of about 51% Monomer and about 49% Dimer;
proportions of about 52% Monomer and about 48% Dimer;
proportions of about 53% Monomer and about 47% Dimer;
proportions of about 54% Monomer and about 46% Dimer;
proportions of about 55% Monomer and about 45% Dimer;
proportions of about 56% Monomer and about 44% Dimer;
proportions of about 57% Monomer and about 43% Dimer;
proportions of about 58% Monomer and about 42% Dimer;
proportions of about 59% Monomer and about 41% Dimer;
proportions of about 60% Monomer and about 40% Dimer;
proportions of about 61% Monomer and about 39% Dimer;
proportions of about 62% Monomer and about 38% Dimer;
proportions of about 63% Monomer and about 37% Dimer;
proportions of about 64% Monomer and about 36% Dimer;
proportions of about 65% Monomer and about 35% Dimer;
proportions of about 66% Monomer and about 34% Dimer;
proportions of about 67% Monomer and about 33% Dimer;
proportions of about 68% Monomer and about 32% Dimer;
proportions of about 69% Monomer and about 31% Dimer;
proportions of about 70% Monomer and about 30% Dimer;
proportions of about 71% Monomer and about 29% Dimer;
proportions of about 72% Monomer and about 28% Dimer;
proportions of about 73% Monomer and about 27% Dimer;
proportions of about 74% Monomer and about 26% Dimer;
proportions of about 75% Monomer and about 25% Dimer;
proportions of about 76% Monomer and about 24% Dimer;
proportions of about 77% Monomer and about 23% Dimer;
proportions of about 78% Monomer and about 22% Dimer;
proportions of about 79% Monomer and about 21% Dimer;
proportions of about 80% Monomer and about 20% Dimer;
proportions of about 81% Monomer and about 19% Dimer;
proportions of about 82% Monomer and about 18% Dimer;
proportions of about 83% Monomer and about 17% Dimer;
proportions of about 84% Monomer and about 16% Dimer;
proportions of about 85% Monomer and about 15% Dimer;
proportions of about 86% Monomer and about 14% Dimer;
proportions of about 87% Monomer and about 13% Dimer;
proportions of about 88% Monomer and about 12% Dimer;
proportions of about 89% Monomer and about 11% Dimer;
proportions of about 90% Monomer and about 10% Dimer;
proportions of about 91% Monomer and about 9% Dimer;
proportions of about 92% Monomer and about 8% Dimer;
proportions of about 93% Monomer and about 7% Dimer;
proportions of about 94% Monomer and about 6% Dimer;
proportions of about 95% Monomer and about 5% Dimer;
proportions of about 96% Monomer and about 4% Dimer;
proportions of about 97% Monomer and about 3% Dimer;
proportions of about 98% Monomer and about 2% Dimer; or
proportions of about 99% Monomer and about 1% Dimer.

It is also contemplated that rusalatide acetate can be manufactured or prepared by any suitable technique, including but not limited to any suitable, reliable and effective method for peptide synthesis. In certain embodiments, rusalatide acetate can be synthesized by a solid phase peptide synthesis method (for example, but not limited to, BOC or FMOC), or in other embodiments by solution phase synthesis. The present invention also contemplates that rusalatide acetate can be synthesized by other suitable techniques including, e.g., combinations of other methods of peptide synthesis described herein, or using recombinant peptide synthesis. rusalatide acetate can also be synthesized and purified according to Good Manufacturing Practice (GMP) requirements.

It is also to be understood that rusalatide acetate, as used throughout this description, can function as an NPAR agonist (wherein NPAR refers to "non-proteolytically-activated thrombin receptor").

It is also contemplated that rusalatide acetate can exist in different salt forms, i.e. as one or more peptide salts, and desired rusalatide acetate peptide salts can be screened, selected and used in the preparation of pharmaceutical compositions, formulations or dosage forms.

The present invention contemplates that chemical or physical instability of Monomer and Dimer can involve, for example, one or more changes in the conformational structure of Monomer and Dimer. Conventional approaches and studies of Monomer and Dimer have failed to account for the critical importance of the conformational structure of the Monomer and Dimer, with regard to stability of the Monomer and Dimer, rusalatide acetate pharmaceutical product development, development of rusalatide acetate formulations, etc. The present invention addresses this significant and long-felt, unmet need.

Preformulation Characterization: Optimizing Parameters to Enhance Stability

The present invention contemplates various methods, processes and systems that can be used at a "preformulation characterization" stage to collect and analyze information about a wide range of parameters that can affect stability of (i) rusalatide acetate or (ii) a rusalatide acetate composition, formulation or dosage form that includes Monomer, Dimer or any combination of Monomer and Dimer, or (iii) both (i) and (ii).

As used herein, the phrase "preformulation characterization" is to be understood to include any steps, procedures, methods, processes and systems, or a combination thereof, that can be used for the purpose of collecting and analyzing information about one or more parameters that can affect stability of (i) rusalatide acetate or (ii) a rusalatide acetate composition, formulation or dosage form that includes Monomer, Dimer or any combination of Monomer and Dimer, or (iii) both (i) and (ii). Such preformulation characterization provides valuable data for the subsequent development of safe and effective rusalatide acetate compositions, dosage forms and formulations comprising stable or stabilized rusalatide acetate.

The present invention therefore contemplates collecting (or gathering) and analyzing information based on one or more parameters which provides very valuable "preformulation characterization data". Representative parameters are described herein in detail. Such "preformulation characterization data" includes data which can be reliably and effectively used at a preformulation stage to develop specific steps and conditions (including but not limited to manufacturing conditions) for enhancing the stability, and therefore optimizing the stability of (i) rusalatide acetate or (ii) a rusalatide acetate composition, formulation or dosage form that includes Monomer, Dimer or any combination of Monomer and Dimer, or (iii) both (i) and (ii). According to the present invention, this very valuable "preformulation characterization data" can be used during subsequent formulation stages for the development of safe and effective rusalatide acetate compositions, formulations and dosage forms comprising stable or stabilized rusalatide acetate.

Representative Examples of Parameters to be Analyzed

In accordance with the present invention, Applicants have discovered novel approaches, methods, processes and systems for stabilizing the Monomer, stabilizing the Dimer, or both, and in preferred embodiments optimizing the stability of (i) rusalatide acetate or (ii) a rusalatide acetate composition, formulation or dosage form that includes Monomer, Dimer or any combination of Monomer and Dimer, or (iii) both (i) and (ii).

There are a wide range of parameters that can affect stability of (i) rusalatide acetate or (ii) a rusalatide acetate composition, formulation or dosage form that includes Monomer, Dimer or any combination of Monomer and Dimer, or (iii) both (i) and (ii), and analysis of these parameters can provide very valuable data (for example, characterization data) and other types of information about the impact of these parameters on stability of rusalatide acetate. Such data and information can be reliably and effectively used at any stage, including for example a preformulation stage, a formulation stage, and any and all other stages in the process of developing a stable rusalatide acetate pharmaceutical composition, dosage form or formulation. Based on an analysis of such parameters, the data and information that is gathered can be used, for example, to develop specific steps and conditions for enhancing the stability, and therefore optimizing the stability of (i) rusalatide acetate or (ii) a rusalatide acetate composition, formulation or dosage form that includes Monomer, Dimer or any combination of Monomer and Dimer, or (iii) both (i) and (ii). The terms "attribute" and "parameter" may be used interchangeably herein.

Representative examples of attributes or parameters that can affect the stability of (i) rusalatide acetate or (ii) a rusalatide acetate composition, formulation or dosage form that includes Monomer, Dimer or any combination of Monomer and Dimer, or (iii) both (i) and (ii), include, but are not limited to, the following:

1) Atmospheric oxygen
2) Any factors, including but not limited to different reactive oxygen species, that affect redox chemistry of the total Monomer or Dimer present (including any factors that cause, produce or result in one or more oxidation or reduction events that affect the stability of (i) rusalatide acetate or (ii) a rusalatide acetate composition, formulation or dosage form that includes Monomer, Dimer or any combination of Monomer and Dimer, or (iii) both (i) and (ii))
3) Moisture content
4) Relative Humidity
5) Type of Carrier
6) pH
7) Temperature
8) Freeze-thaw cycles, and effects of physical state of a rusalatide acetate formulation on stability
9) Any conformational changes in the structure of Monomer or Dimer
10) Crystalline form versus amorphous state of rusalatide acetate
11) Buffer composition
12) Presence of one or more excipients (this list of excipients is not intended to be limiting in any way, and the examples of types of excipients listed below are for illustration purposes only)
   a) Stabilizing agents
   b) Binding agents
   c) Buffering agents (e.g., to adjust pH)
   d) Tonicity adjusting agents (for example, for rusalatide acetate solutions)
   e) Antiadherents
   f) Diluents
   g) Glidants
   h) Disintegrants
   i) Fillers
   j) Desiccants or hygroscopic substances or agents
   k) Sorbents
   l) Hydrophilic Lubricants
   m) Hydrophobic Lubricants
   n) Emulsifying agents
   o) Flavoring agents
   p) Coatings or coating excipients
   q) Coloring agents
   r) Preservatives
   s) Sweetening agents
13) Sterility (in particular, the degree to which rusalatide acetate, or a rusalatide acetate pharmaceutical composition, dosage form or formulation is sterile or free from microorganisms or germs)

14) Impact of viscosity of a particular formulation on stability
15) Hydrophilic interactions, hydrophobic interactions and any other interactions with any components in a formulation or pharmaceutical composition; and effects of any materials used in containers, kits, packaging and/or storage, on stability
16) Impact of exposure to light on stability (e.g., effects of photolysis and photo-oxidation)
17) Effects of ions, salts, and ionic strength on stability of (i) rusalatide acetate or (ii) a rusalatide acetate composition, formulation or dosage form that includes Monomer, Dimer, or any combination of Monomer and Dimer, or (iii) both (i) and (ii)
18) Binding to transition metals; oxidation catalyzed by the presence of transition metal ions
19) Impact of temperature, time and concentration (e.g., concentration of rusalatide acetate peptide), the order of mixing on stability, or any combination thereof
20) Effects of any contaminants or impurities on stability, e.g., presence of any contaminants or impurities in a batch of rusalatide acetate, or in a formulation or pharmaceutical composition
21) Potential effects on stability produced by agitation, lyophilization, or other process steps and procedures, e.g., during the process of preparing a rusalatide acetate formulation In addition to these attributes or parameters, the present invention also contemplates the analysis of other physicochemical properties of rusalatide acetate. Several of these representative attributes or parameters and physicochemical properties of rusalatide acetate are described herein, and in the Examples section of this disclosure.

Some of the additional, representative attributes or parameters and physicochemical properties that can be analyzed and evaluated, in order to enhance and optimize the stability of rusalatide acetate, include, but are not limited to, predicted half-life of Monomer and Dimer (including predicted half-life in an intestine-like environment), and hydrophobicity value (or hydrophobicity index) in kilojoules per mole (KJ/mol) based on the rusalatide acetate amino acid sequence. Additional physicochemical properties that can be analyzed, based on the rusalatide acetate amino acid sequence (for both Monomer and Dimer), include but are not limited to the following:

residue volume (this is determined based on the sum of the residue volume values, measured in cubic angstroms, wherein the residue volume value for each amino acid residue in the rusalatide acetate sequence is determined based on the volume of space enclosed by the van der Waals surface for that given residue);

surface accessibility value (the surface accessibility is calculated based on the sum of the average accessibility surface area values for the individual amino acids in the rusalatide acetate sequence);

flexibility value (this is a measure of amino acid side chain flexibility, determined based on the sum of amino acid scale values);

charge (based on the overall charge, calculated based on the rusalatide acetate sequence);

polarity (based on the sum of polarity values for the individual amino acids in the sequence);

relative mutability (based on the sum of the relative mutability values for the individual amino acids in the sequence);

free energy of solution (in water, kcal/mole);

optical rotation (based on the average of the optical rotation values for the individual amino acids in the sequence);

pKa;

pKb;

isoelectric point (pI, pH(I), IEP);

entropy of formation (based on the sum of entropy of formation values, given the rusalatide acetate amino acid sequence);

charge-pH map;

molecular weight;

"GRAVY" value (as used herein, this refers to the "grand average of hydropathy" and is a score or measurement that is used to help analyze and evaluate the hydrophobicity of the rusalatide acetate peptide);

heat capacity (based on the sum of heat capacity values, given the rusalatide acetate amino acid sequence); and relative stability (based on the average of relative stability scale values for individual amino acids, and given the rusalatide acetate amino acid sequence).

Some of the representative examples described herein illustrate an analysis of these attributes or parameters and physicochemical properties, and use of this analysis to enhance and optimize the stability of rusalatide acetate in a pharmaceutical composition, formulation or dosage form.

As further described herein, the present invention also contemplates other methods for enhancing stability including, for example, but not limited to, enhancing stability by protection against cleavage of the Asp-Pro bond in Monomer or Dimer; and enhancing stability of (i) rusalatide acetate or (ii) a rusalatide acetate composition, formulation or dosage form that includes Monomer, Dimer or any combination of Monomer and Dimer, or (iii) both (i) and (ii), by minimizing the effects of hydrolysis.

Atmospheric Oxygen (e.g., Exposure to Air)

One of the parameters that can affect stability of (i) rusalatide acetate or (ii) a rusalatide acetate composition, formulation or dosage form that includes Monomer, Dimer, or any combination of Monomer and Dimer, or (iii) both (i) and (ii), is atmospheric oxygen (for example, exposure to air).

As described herein, because rusalatide acetate contains a single cysteine residue, it is capable of forming a dimer via formation of a disulfide bond. Often times a characteristic of cysteine-containing peptides is the tendency of the cysteine residue to undergo reversible oxidation.

Susceptibility to oxidation can be sequence-dependent and the present invention contemplates that even minimal exposure to air of cysteine-containing peptides can lead to oxidation. Conventional studies using rusalatide acetate have not accounted for the effects of exposure to air as one parameter that affects stability.

In preferred embodiments, the present invention contemplates the use of degassed or deoxygenated solvents and solutions to enhance stability of rusalatide acetate, and to minimize or avoid any undesired oxidation of rusalatide acetate.

In other preferred embodiments, the present invention contemplates the use of a non-reactive, anhydrous purging agent, such as for example anhydrous nitrogen gas or anhydrous argon gas. The term "non-reactive, anhydrous purging agent" is intended to refer to an agent that displaces oxygen or purges oxygen from a space after introduction of the purging agent into the space. For example, introduction of anhydrous nitrogen gas or anhydrous argon gas into the headspace of a vial will effectively displace or purge all or substantially all of the oxygen from the headspace of the vial. Moreover, the term "anhydrous" as used herein indicates that the purging agent contains no water, essentially no water, or substantially no water. In addition, the purging agent is "non-reactive" meaning that the purging agent does not react with rusalatide acetate via any redox mechanism (i.e., does not react via any oxidation or reduction of rusalatide acetate), and also does not react with any other component of the composition (e.g., including any excipients) via any redox mechanism (i.e., oxidation or reduction mechanism). Therefore, the purging agent will not react, e.g. through any redox mechanism, with rusalatide acetate or any excipient or other component of a rusalatide acetate formulation, composition or dosage form.

Other non-reactive, anhydrous purging agents may also be used, and these may include for example one or more noble gases. As described herein, the present invention also contemplates the use of a non-reactive, substantially anhydrous purging agent. The use of such an anhydrous purging agent, or substantially anhydrous purging agent, helps to displace oxygen and thus minimize any potential undesired oxidation of rusalatide acetate. By displacing the ambient air, and thus minimizing exposure of the rusalatide acetate to the ambient air (including ambient oxygen), the purging agent also helps minimize exposure of the rusalatide acetate to any moisture in the air, which thus enhances the stability of the rusalatide acetate.

In one embodiment of the invention, nitrogen gas can be used to displace any ambient oxygen in the air that might lead to undesired oxidation of residues in rusalatide acetate.

The present invention also contemplates that when a rusalatide acetate composition, formulation or dosage form is developed, comprising Monomer, Dimer or any combination of Monomer and Dimer in the rusalatide acetate composition, formulation or dosage form, certain procedures and steps can be taken to minimize the impact of exposure to air as one parameter that affects stability. For example, after removing a particular amount or volume of a rusalatide acetate formulation or pharmaceutical composition from a container, the container should be re-sealed, preferably under an atmosphere of dry nitrogen. This can be achieved, for example, by using appropriate instrumentation, e.g. sterile tubing connected to a nitrogen tank, and releasing a gentle stream of an appropriate amount of dry nitrogen (e.g. from the outlet end of the sterile tubing), and taking great care not to displace any rusalatide acetate peptide powder out of the container. After the air is displaced, and the container is re-sealed under an atmosphere of dry nitrogen, and under sterile conditions, the container can be returned to cold storage and maintained at an appropriate temperature and maintained at other appropriate conditions, as described herein to enhance and optimize the stability. The present invention contemplates that this procedure will minimize the undesired oxidation due to exposure to air.

Other Factors, Including but not Limited to Different Reactive Oxygen Species, that Affect Redox Chemistry of the Monomer, Dimer, or any Combination of Monomer and Dimer The present invention contemplates that other parameters that can affect stability of (i) rusalatide acetate or (ii) a rusalatide acetate composition, formulation or dosage form that includes Monomer, Dimer or any combination of Monomer and Dimer, or (iii) both (i) and (ii), include, for example, the presence of one or more reactive oxygen species, contaminating oxidants, impurities, or other factors that can affect redox chemistry of the Monomer, Dimer or any combination of Monomer and Dimer. This includes any factors that cause, produce or result in one or more oxidation or reduction events that affect the stability of (i) rusalatide acetate or (ii) a rusalatide acetate composition, formulation or dosage form that includes Monomer, Dimer or any combination of Monomer and Dimer, or (iii) both (i) and (ii). Representative examples of different reactive oxygen species include, but are not limited to, superoxide radical, singlet oxygen, hydroxyl radical, and hydrogen peroxide.

Exposure to ionizing radiation can also produce one or more different reactive oxygen species which can affect the stability of (i) rusalatide acetate or (ii) a rusalatide acetate composition, formulation or dosage form that includes Monomer, Dimer or any combination of Monomer and Dimer, or (iii) both (i) and (ii). In one non-limiting example, a series of controlled experiments are performed (i.e., with all proper control groups, for statistical analysis) under sterile conditions to test and evaluate the extent to which ionizing radiation and different reactive oxygen species, including but not limited to superoxide radical, singlet oxygen, hydroxyl radical, and hydrogen peroxide, are parameters that affect the stability of (i) rusalatide acetate or (ii) a rusalatide acetate composition, formulation or dosage form that includes Monomer, Dimer or any combination of Monomer and Dimer, or (iii) both (i) and (ii). Here is a more detailed summary of the example:

In a control group, an aqueous formulation of rusalatide acetate is prepared (by combining a pure aqueous solvent with one milligram of solid lyophilized rusalatide acetate), and the formulation is stored at about four degrees Celsius (about 4° C.), in a cool, dark place, away from bright light, in an opaque vial. The control group (in the opaque vial) is not exposed to any ionizing radiation.

Several different opaque "test vials" are prepared, and each separate opaque test vial contains its own separate aqueous formulation of rusalatide acetate (for each separate test vial, an aqueous formulation is prepared by combining a pure aqueous solvent with one milligram of solid lyophilized rusalatide acetate). Each test vial is an opaque vial, to protect the rusalatide acetate from exposure to light, and each test vial is stored at about four degrees Celsius (about 4° C.), in a cool, dark place, away from bright light.

The first opaque test vial is exposed to six gray (6 Gy) of ionizing radiation at a rate of 500 cGy/minute (centigray/minute).

The second opaque test vial is exposed to six and one-half gray (6.5 Gy) of ionizing radiation at a rate of 500 cGy/minute.

The third opaque test vial is exposed to seven gray (7 Gy) of ionizing radiation at a rate of 500 cGy/minute.

The fourth opaque test vial is exposed to seven and one-half gray (7.5 Gy) of ionizing radiation at a rate of 500 cGy/minute.

The fifth opaque test vial is exposed to eight gray (8 Gy) of ionizing radiation at a rate of 500 cGy/minute.

The sixth opaque test vial is exposed to eight and one-half gray (8.5 Gy) of ionizing radiation at a rate of 500 cGy/minute.

The seventh opaque test vial is exposed to nine gray (9 Gy) of ionizing radiation at a rate of 500 cGy/minute.

The eighth opaque test vial is exposed to nine and one-half gray (9.5 Gy) of ionizing radiation at a rate of 500 cGy/minute.

All of the data is analyzed, and a physical, tangible computer system is used for performing computational analysis that utilizes predictive analytics, machine learning and predictive modeling. The predictive analytics, machine learning and predictive modeling provide very valuable information about the effects of ionizing radiation on the stability of (i) rusalatide acetate or (ii) a rusalatide acetate composition, formulation or dosage form that includes Monomer, Dimer, or any combination of Monomer and Dimer, or (iii) both (i) and (ii).

Also, based on other controlled experiments, the effects of different reactive oxygen species, including but not limited to the effects of superoxide radical, singlet oxygen, hydroxyl radical, and hydrogen peroxide, are analyzed in terms of effects on the stability of (i) rusalatide acetate or (ii) a rusalatide acetate composition, formulation or dosage form that includes Monomer, Dimer, or any combination of Monomer and Dimer, or (iii) both (i) and (ii).

Unwanted or undesired oxidation of Monomer, Dimer or any combination of Monomer and Dimer, may result in reduction or loss of biological activity and other undesirable pharmaceutical consequences. In preferred embodiments, the present invention contemplates that conditions can be adjusted to reduce or prevent the impact of unwanted or undesired oxidation on the stability of (i) rusalatide acetate or (ii) a rusalatide acetate composition, formulation or dosage form that includes Monomer, Dimer or any combination of Monomer and Dimer, or (iii) both (i) and (ii). For instance, the presence of reactive oxygen species, contaminating oxidants or impurities can be minimized or removed. The present invention also contemplates that unwanted or undesired oxidation can be effectively inhibited by the appropriate addition of one or more antioxidants or free radical scavengers to a pharmaceutical composition, dosage form or formulation comprising rusalatide acetate.

An "antioxidant," as used herein, is a compound which can be used to prevent or reduce an oxidation reaction caused by an oxidizing agent. Examples of antioxidants include, but are not limited to, tocopherol, methionine, glutathione, tocotrienol, dimethylglycine, betaine, butylated hydroxyanisole, butylated hydroxytoluene, vitamin E, ascorbic acid, ascorbyl palmitate, thioglycolic acid and antioxidant peptides such as, for example, turmerin. It is understood that certain chelating agents or thiol-containing compounds may also function as an antioxidant, for example, tris(2-carboxyethyl) phosphine, cysteine or dithiothreitol. Other types of commonly used antioxidants, however, do not contain a thiol group. If an antioxidant is included, it is preferred that between about 0.001% and about 10.0% by weight, preferably between about 0.01% and about 5.0%, and more preferably between about 0.05% and about 2.0% by weight of an antioxidant is present in the rusalatide acetate pharmaceutical compositions, formulations and dosage forms of the present invention.

Moisture Content

Moisture content is another parameter that can affect stability of (i) rusalatide acetate or (ii) a rusalatide acetate composition, formulation or dosage form that includes Monomer, Dimer or any combination of Monomer and Dimer, or (iii) both (i) and (ii). Contamination with moisture can greatly decrease the long-term stability of solid peptides. The present invention contemplates steps that can be taken to minimize the effects of moisture on the stability of (i) rusalatide acetate or (ii) a rusalatide acetate composition, formulation or dosage form that includes Monomer, Dimer or any combination of Monomer and Dimer, or (iii) both (i) and (ii). For example, throughout the preformulation and formulation stages, and when a batch of rusalatide acetate is prepared, the rusalatide acetate can be kept in a cool, dark place and steps can be taken to minimize and control the moisture content. In preferred embodiments, the present invention contemplates that rusalatide acetate should be stored under refrigeration at 4° C. or colder, and away from bright light. In certain situations, it may be necessary to maintain dry peptides at room temperature for a period of time. However, for long term storage and to enhance stability, the present invention also contemplates that rusalatide acetate (for instance, dry or lyophilized rusalatide acetate) should preferably be stored at −20° C. or about −20° C., with a dessicant (e.g., a dessicant placed within a vial containing the rusalatide acetate) to further enhance stability, and preferably under conditions in which the rusalatide acetate is protected from exposure to light.

In certain preferred embodiments, one or more desiccants, hygroscopic agents or drying agents can be used to minimize moisture content for enhancing the stability and shelf life of (i) rusalatide acetate or (ii) a rusalatide acetate composition, formulation or dosage form that includes Monomer, Dimer, or any combination of Monomer and Dimer, or (iii) both (i) and (ii), for instance when the rusalatide acetate is in a lyophilized form. With regard to the present invention, as described herein, the terms desiccant, hygroscopic agent or drying agent are used interchangeably, and each is used for reducing moisture content and thus inducing or sustaining a state of dryness. The present invention also contemplates that selection and use of suitable and appropriate desiccants can help ensure the integrity and performance of the finished pharmaceutical product. Silica gel (silicone dioxide) and molecular sieve (synthetic zeolite) are preferred, non-limiting examples of desiccants that can be used to minimize moisture content and for enhancing the stability and shelf life of rusalatide acetate. A preferred form of using the desiccant, for instance, for use of either silica gel (silicone dioxide) or molecular sieve (synthetic zeolite), is a desiccant bag which is complies with all regulatory requirements, including EU regulations and U.S. FDA regulations for use in pharmaceutical applications.

The present invention also contemplates other approaches to minimize the impact of moisture content on stability and shelf life of (i) rusalatide acetate or (ii) a rusalatide acetate composition, formulation or dosage form that includes Monomer, Dimer or any combination of Monomer and Dimer, or (iii) both (i) and (ii). Each time an amount of rusalatide acetate is going to be used from a container, one should preferably remove the container from cold storage and allow it to equilibrate to room temperature or slightly warmer before opening it. This will reduce the uptake of moisture from the air onto the cold surface of the solid peptide or the inside of the container.

Relative Humidity

Relative humidity (RH) is another parameter that can affect stability of (i) rusalatide acetate or (ii) a rusalatide acetate composition, formulation or dosage form that includes Monomer, Dimer or any combination of Monomer and Dimer, or (iii) both (i) and (ii). The present invention contemplates that the effects of RH can be analyzed on the stability of (i) rusalatide acetate or (ii) a rusalatide acetate composition, formulation or dosage form that includes Monomer, Dimer or any combination of Monomer and Dimer, or (iii) both (i) and (ii). Effects of RH that can be analyzed include, but are not limited to, degradation of Monomer, Dimer, or any combination of Monomer and Dimer. For example, (i) rusalatide acetate or (ii) a rusalatide acetate composition, formulation or dosage form that includes Monomer, Dimer or any combination of Monomer and Dimer, or (iii) both (i) and (ii), can be exposed to varying temperature and relative humidity conditions for any length of time. By way of example, which does not limit the scope of the invention in any way, rusalatide acetate samples can be exposed to a temperature range from about 40° C. to about 80° C. and a RH from about 0% to about 75%, and for a period of time lasting for several weeks. Other suitable temperature and RH conditions (for instance, any RH value within the range of from about 0% RH to about 100% RH) can be tested as well. As described herein, effects of RH that can be analyzed include, but are not limited to, degradation of Monomer, Dimer, or any combination of Monomer and Dimer.

Type of Carrier

Another one of the parameters that can affect stability of (i) rusalatide acetate or (ii) a rusalatide acetate composition, formulation or dosage form that includes Monomer, Dimer or any combination of Monomer and Dimer, or (iii) both (i) and (ii), is the type of carrier used in the composition, dosage form or formulation. For example, the carrier may comprise one or more different types of solvents. The present invention contemplates that specific solvents can be analyzed and screened during a preformulation stage to gather preformulation characterization data in order to identify specific solvents that may affect the stability of rusalatide acetate.

In other embodiments of the invention, as described herein, the carrier may comprise a saline solution or other aqueous solution, i.e., an "aqueous carrier", and the methods, processes and systems of the present invention (for example, for optimizing stability) can be safely, reliably and accurately used to enhance the stability of (i) rusalatide acetate or (ii) a rusalatide acetate composition, formulation or dosage form that includes Monomer, Dimer, or any combination of Monomer and Dimer, or (iii) both (i) and (ii), in a saline solution or other aqueous solution. The term "aqueous carrier" as used herein broadly refers to any pharmaceutically safe and effective carrier or delivery vehicle that contains water. The present invention contemplates that the total amount of water present in an aqueous carrier can include any percentage of water in the total amount of the carrier (for instance, as calculated on a volume-by-volume basis), depending on the specific needs or requirements for a particular composition, formulation or dosage form. For example, an aqueous carrier or delivery vehicle used in the formulation or preparation of an ointment, cream, or gel can comprise about five percent water, while the other components of the aqueous carrier or delivery vehicle used in the formulation (e.g., including excipients) account for the remaining total percentage. Other examples of carriers include, for example, aqueous solutions such as physiologically buffered saline or other solvents or vehicles such as glycerol, glycols, oils such as olive oil or injectable organic esters. These are just a few non-limiting examples and do not limit the scope of the present invention in any way.

pH

Another one of the parameters is pH which can affect stability of (i) rusalatide acetate or (ii) a rusalatide acetate composition, formulation or dosage form that includes Monomer, Dimer or any combination of Monomer and Dimer, or (iii) both (i) and (ii). The present invention contemplates that adjustment in pH can be utilized to help control the rate of formation of Dimer. It has been found that Monomer peptides dimerize spontaneously in a saline solution, which is one example of Dimerization. Because each Monomer contains a single cysteine residue, two Monomers are capable of forming a Dimer via formation of a disulfide bond. Monomers can therefore undergo dimerization resulting from disulfide bond formation, to form a Dimer. The actual amount of Monomer can therefore diminish over time because of dimerization. For example, under certain conditions, Monomer has been found to have a half-life of about 2 to about 4 hours in buffered solutions at neutral pH.

Oxidation of cysteine residues can be accelerated at higher pH, where the thiol is more easily deprotonated and readily forms intra-chain or inter-chain disulfide bonds. Rate of oxidation increases with pH, so even if the rusalatide acetate peptide is in the fully reduced form initially, some oxidation will occur if the rusalatide acetate peptide is maintained under neutral or basic conditions. The present invention contemplates that formation of Dimer is accelerated at higher pH since oxidation of cysteine residues (in each Monomer) is accelerated at higher pH. Therefore, where it is desired to accelerate the formation of Dimer, the present invention contemplates that the pH can be increased accordingly to a higher pH.

In other embodiments, when it is desired to reduce the rate of oxidation of the cysteine residue, the rusalatide acetate peptide is maintained at more acidic conditions (pH<7).

Temperature

Temperature is another one of the parameters which can affect stability of (i) rusalatide acetate or (ii) a rusalatide acetate composition, formulation or dosage form that includes Monomer, Dimer or any combination of Monomer and Dimer, or (iii) both (i) and (ii). It is contemplated that temperature has an important role in the stability of (i) rusalatide acetate or (ii) a rusalatide acetate composition, formulation or dosage form that includes Monomer, Dimer or any combination of Monomer and Dimer, or (iii) both (i) and (ii), and temperature is described in several contexts throughout the description of the present invention. The present invention contemplates that temperature is one parameter that can be controlled to enhance the stability of rusalatide acetate in a wide range of pharmaceutical compositions, formulations and dosage forms.

For example, the present invention contemplates that temperature is one parameter that can be controlled to enhance the stability of (i) rusalatide acetate or (ii) a rusalatide acetate composition, formulation or dosage form that includes Monomer, Dimer or any combination of Monomer and Dimer, or (iii) both (i) and (ii), for example, when using a lyophilized form. In a preferred embodiment, rusalatide acetate is maintained in a lyophilized or freeze-dried form. Freeze drying is a low temperature dehydration process which involves freezing the product, lowering pressure, then removing the ice by sublimation. During the lyophilization or freeze-drying process, water is removed from the rusalatide acetate pharmaceutical product after it is frozen and placed under a vacuum. Freeze-dried rusalatide acetate pharmaceutical products can be produced as lyophilized powders for reconstitution in vials before administration to a patient. In a preferred embodiment, to prevent or minimize peptide degradation, and to enhance the stability of rusalatide acetate, rusalatide acetate is stored in lyophilized form at a cold temperature, for example (but not limited to) −20° Celsius or preferably at −80° Celsius. Rusalatide acetate may also be stored in lyophilized form at other cold temperatures.

Freeze-Thaw Cycles and Effects of Physical State of a Rusalatide Acetate Formulation on Stability Freeze-thaw cycles are another parameter that can affect stability of (i) rusalatide acetate or (ii) a rusalatide acetate composition, formulation or dosage form that includes Monomer, Dimer or any combination of Monomer and Dimer, or (iii) both (i) and (ii). In a preferred embodiment, the present invention contemplates that stability of rusalatide acetate is enhanced by avoiding freeze-thaw cycles. If rusalatide acetate is in solution, freeze-thaw cycles are preferably avoided by freezing individual aliquots and then using those individual aliquots only once (e.g., as "single use" aliquots).

Another example of a parameter that can affect stability of (i) rusalatide acetate or (ii) a rusalatide acetate composition, formulation or dosage form that includes Monomer, Dimer or any combination of Monomer and Dimer, or (iii) both (i) and (ii) is the physical state of a particular rusalatide acetate composition, formulation or dosage form, and the impact of that physical state on stability of the rusalatide acetate or the rusalatide acetate composition, formulation or dosage form. The present invention contemplates that the viscosity and other conditions of a pharmaceutical composition, formulation or dosage form comprising rusalatide acetate can be optimized in order to enhance the stability of the rusalatide acetate.

Conformational Changes in the Structure of Monomer, Dimer, or Both; and Crystalline Form Versus Amorphous State of Monomer, Dimer, or Both Another one of the parameters that can affect stability is the conformational structure of the Monomer and the Dimer, including conformational changes in the structure of the Monomer, the Dimer, or both. Physical instability of a peptide can involve transformations in the conformational structure of the peptide. Conventional approaches and studies of rusalatide acetate have failed to account for the critical importance of this parameter, with regard to stability of the Monomer and Dimer, rusalatide acetate pharmaceutical product development, development of rusalatide acetate formulations, etc. The present invention addresses this significant and long-felt, unmet need.

The present invention contemplates methods and processes for stabilizing rusalatide acetate formulations, compositions and dosage forms in order to maintain optimum pharmaceutical activity.

The present invention also contemplates methods and systems for enhancing stability based on analysis of Monomer structure and Dimer structure.

As further described herein, the present invention contemplates that one or more changes or transformations in the conformational structure of Monomer, Dimer or both can affect stability of Monomer, Dimer or both.

It is also contemplated that all methods, systems, processes, etc as described herein, for enhancing and optimizing stability, can also effectively be used for enhancing the stability of (i) rusalatide acetate, or any pharmaceutically effective salt thereof; and (ii) any rusalatide acetate composition, formulation or dosage form that includes Monomer, Dimer or any combination of Monomer and Dimer.

Applicants have discovered approaches that can be taken to enhance the stability of (i) rusalatide acetate, or any pharmaceutically effective salt thereof; and (ii) any rusalatide acetate composition, formulation or dosage form that includes Monomer, Dimer or any combination of Monomer and Dimer, based on predictions and analysis of conformational changes in peptide structure.

To further characterize and analyze this parameter, one or more reliable tools can be used for predicting the conformational structure, and any changes in the conformational structure of Monomer, Dimer or both. These tools provide very useful characterization data and information for predicting and enhancing peptide stability during the preformulation and formulation stages. Such tools generate physical, non-abstract information and characterization data about the conformational structure of Monomer, Dimer or both. The physical, non-abstract information and characterization data that is gathered based on an analysis of the conformational structure can be used, for example, for performing at least one physical, non-abstract stability optimization procedure based on the analysis such that the stability of rusalatide acetate formulations, compositions and dosage forms is enhanced.

The present invention also contemplates the use of such reliable tools for predicting, gathering physical non-abstract information, and analyzing any changes or transformations in the conformational structure of Monomer, Dimer or both under all types of conditions and during any and all preformulation and formulation stages of pharmaceutical product development. Such conditions and stages may include, for example, when a pharmaceutical composition, formulation or dosage form comprising Monomer, Dimer, or any combination of Monomer and Dimer is prepared according to certain conditions including, for example, a specific pH, temperature, moisture content, relative humidity, exposure to light, in the presence of one or more excipients, in the presence of one or more specific solvents or other carriers, when formulated in a specific dosage form, or based on one or more other parameters (as described herein) that can affect the stability of Monomer, Dimer, or any combination of Monomer and Dimer. Under a certain set of very specific conditions, such reliable tools can then be used to predict, gather physical non-abstract information and analyze any changes or transformations in the conformational structure of Monomer, Dimer or both. This data can then be used for performing at least one physical, non-abstract stability optimization procedure based on the analysis such that the stability of (i) rusalatide acetate or (ii) a rusalatide acetate composition, formulation or dosage form that includes Monomer, Dimer or any combination of Monomer and Dimer, or (iii) both (i) and (ii), is enhanced.

Some representative examples of such reliable tools, e.g., reliable tools for predicting, gathering physical non-abstract information, and analyzing any changes or transformations in conformational structure, include but are not limited to the following proprietary tools: GenScript's Peptide Property Tool; Peptide Synthesis and Proteotypic Peptide Analyzing Tool; and tools available via the "PEP-FOLD" server.

For example, a predicted structure of a Monomer can be generated based on the primary structure of the synthetic 23-amino acid Monomer peptide, using the "PEP-FOLD" server.

In one non-limiting example, the PEP-FOLD server can be used to generate a "ball and stick" model which schematically depicts a predicted 3D conformation of the Monomer. The predicted 3D conformation of the Monomer can be rotated or viewed in different orientations. Examples of these different orientations are schematically depicted in FIG. 1A, FIG. 1B, and FIG. 1C.

FIG. 1A depicts the Monomer in one 3D orientation (see reference numeral 100 with the arrow that points to the Monomer in this 3D orientation).

Figure 1B:
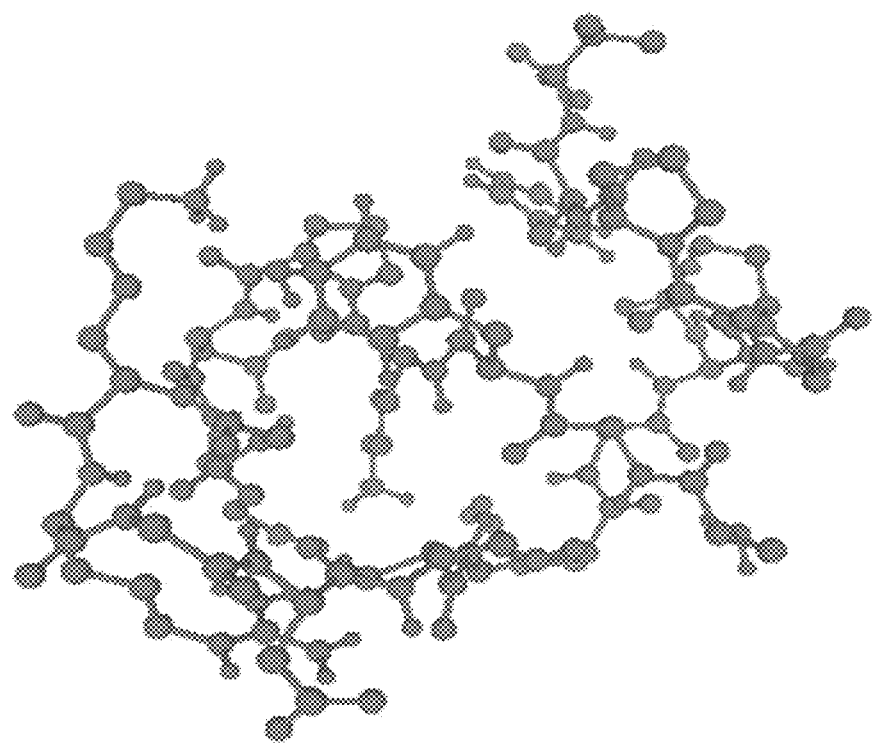
FIG. 1B depicts the Monomer in another 3D orientation.
Figure 1B:

FIG. 1B depicts the Monomer in another 3D orientation (see reference numeral 110 with the arrow that points to the Monomer in this 3D orientation).

Figure 1C:
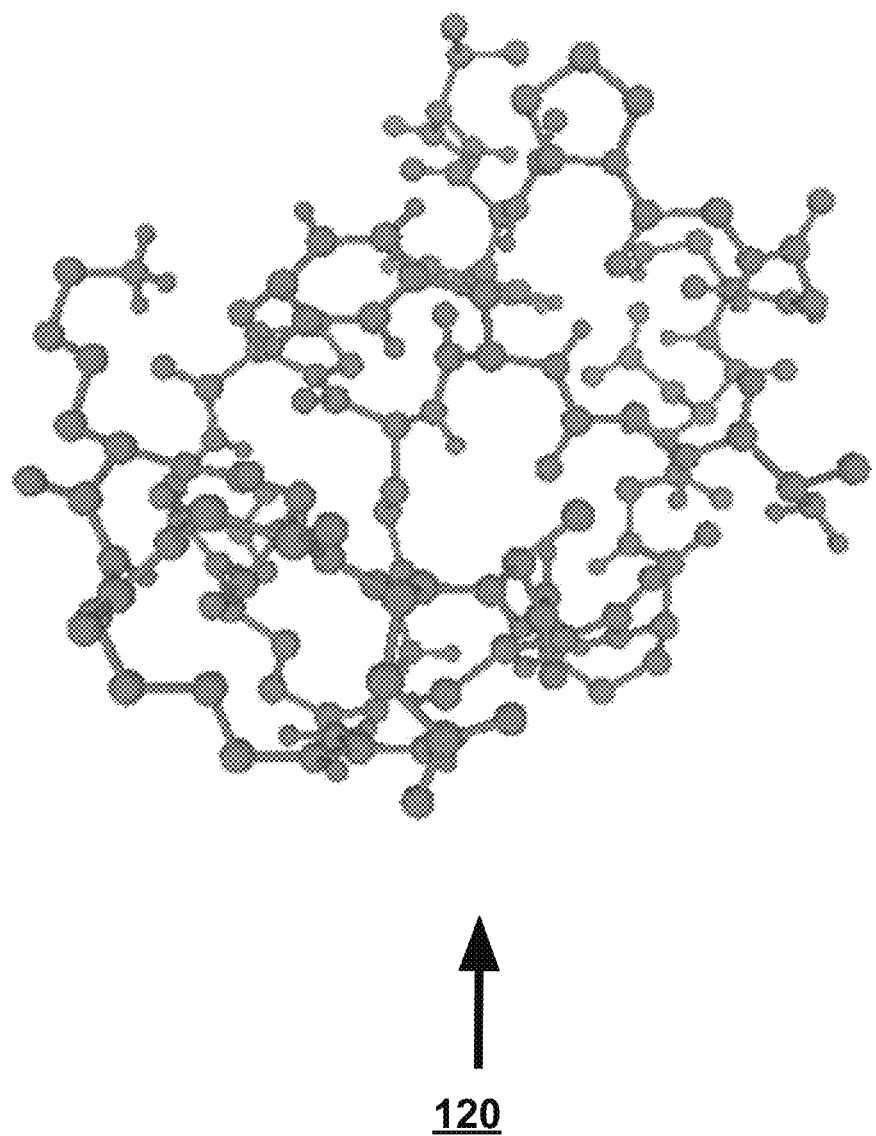
FIG. 1C depicts the Monomer in yet another 3D orientation.

FIG. 1C depicts the Monomer in yet another 3D orientation (see reference numeral 120 with the arrow that points to the Monomer in this 3D orientation).

Similar analysis of predicted 3D conformations can be done for the Dimer.

The PEP-FOLD server provides very valuable information about the rusalatide acetate peptide, including predicted 3D conformations, and analysis of this information is very useful during preformulation and formulation stages. The information gathered in this manner can also be used by machine learning systems, artificial intelligence tools, or other analytical techniques, computer systems and other tools for enhancing and optimizing the stability of rusalatide acetate in rusalatide acetate pharmaceutical compositions, formulations and dosage forms.

According to the present invention, such prediction models of rusalatide acetate structure provide unexpected advantages and benefits for gathering information that is very valuable and useful for enhancing the stability of Monomer, Dimer, or any combination of Monomer and Dimer. These types of approaches can be utilized for gathering information that is very valuable and useful for enhancing the stability of (i) rusalatide acetate or (ii) a rusalatide acetate composition, formulation or dosage form that includes Monomer, Dimer or any combination of Monomer and Dimer, or (iii) both (i) and (ii).

The present invention also contemplates that rusalatide acetate can also exist in either amorphous or crystalline form. In a crystalline formulation, for example, rusalatide acetate may be present in a more concentrated form, and the chemical and physical stability of rusalatide acetate in a crystalline formulation may be greater in comparison to rusalatide acetate in an amorphous state due to the more compact molecular arrangement of the peptide in the crystalline form, restricted molecular motion in the crystalline form, and higher purity.

The present invention also contemplates that one or more different crystallization techniques can be used to obtain various forms of the Monomer and Dimer, with suitable and effective crystallization screening to screen for the crystalline form. To analyze and characterize the properties of the various forms of the Monomer and Dimer, any number of suitable techniques can be used. For example, these techniques include, but are not limited to, a) X-Ray Powder Diffraction; b) thermal analyses; c) infrared spectroscopy; d) NMR Spectroscopy; and e) Moisture Sorption/Desorption Analyses.

Initial screening can be conducted, for example, using one or more various vapor diffusion techniques (for instance, sitting drop, sandwich drop, hanging drop, and capillary) and the present invention also contemplates that one or more batch crystallization techniques (for instance, anti-solvent precipitation, slow evaporation, and fast evaporation techniques) can also be used.

In addition, the present invention also contemplates that experiments can be performed in which mechanical and optical measuring techniques are used to help predict crystallization of rusalatide acetate. In order to determine when and how rusalatide acetate will crystallize, terahertz spectroscopy and dynamic mechanical analysis can be used.

Buffer Composition

Another one of the parameters that can affect stability of rusalatide acetate formulations, compositions and dosage forms is the buffer composition. The present invention contemplates that the composition, pH, temperature, and other conditions of the buffer can be adjusted and optimized such that the stability of the rusalatide acetate formulations, compositions and dosage forms is enhanced.

Presence of One or More Excipients

As further described herein, additional representative examples of parameters that can affect stability of rusalatide acetate formulations, compositions and dosage forms include, but are not limited to, the presence of one or more excipients in the formulations, compositions and dosage forms. It is to be understood that the list of excipients described herein is not intended to be limiting in any way, and the examples of types of excipients described herein are for illustration purposes only. Examples of such excipients are described in more detail herein.

It is to be understood that the present invention contemplates the use of any suitable and pharmaceutically acceptable excipient in the manufacture and production of formulations, compositions and dosage forms comprising rusalatide acetate, including Monomer, Dimer, or any combination of Monomer and Dimer which may be present at any time in any ratio, proportion or percentage of the formulations, compositions and dosage forms. For example, the present invention contemplates the use of any suitable and pharmaceutically acceptable excipient, for example, as disclosed in the "Handbook of Pharmaceutical Excipients" (Sixth Edition, Pharmaceutical Press and American Pharmacists Association 2009), which is incorporated by reference herein in its entirety.

The present invention contemplates that one or more stabilizing agents may be utilized to enhance the stability of (i) rusalatide acetate or (ii) a rusalatide acetate composition, formulation or dosage form that includes Monomer, Dimer or any combination of Monomer and Dimer; or (iii) both (i) and (ii).

In a preferred embodiment, the present invention provides a method of stabilizing a rusalatide acetate composition, formulation or dosage form comprising an oxidatively unstable peptide, wherein the method comprises adding an effective amount of a stabilizing agent to the composition, formulation or dosage form. As used herein "oxidatively unstable peptide" refers to Monomer, Dimer or any combination of Monomer and Dimer, that can be susceptible to degradation, for example, in the presence of oxygen and certain transition metals.

Some representative examples of stabilizing agents include, but are not limited to, chelant agents or other types of agents that enhance the stability of rusalatide acetate. Certain stabilizing agents may inhibit oxidative degradation of an oxidatively unstable rusalatide acetate peptide. Other examples of stabilizing agents include, but are not limited to, silica, chitin derivative such as chitosan, polyamides such as poly(aspartic acid-co-.omega.-amino acid and polymeric amides such as poly[iminocarbonyl(2,5-dihydroxy-1,4-phenylene) carbonylimino-1,4-phenylen-emethylene-1,4-phenylene], CAS #87912-00-3, polymeric lactams such as polyvinylpyrrolidone, polyamino carboxylic acids such as diethylenetriaminepentaacetic acid and triethylenetriaminepentaacetic acid, polymeric amines such as polyallylamine, crown ethers such as 18-crown-6, 21-crown-7, and 24-crown-8, cellulose and its derivatives, and N,N,N',N',N",N"-hexa(2-pyridyl)-1,3,5-tris(aminomethyl)benzene, and certain macrocyclic ligands such as crown ethers, ligand containing knots and catenands. Some examples of preferred stabilizing agents are polyamino carboxylic acids such as diethylenetriaminepentaacetic acid and triethylenetriaminepentaacetic acid. Particularly preferred examples of stabilizing agents are diethylenetriaminepentaacetic acid ("DTPA"), or salts of DTPA such as $CaNa_3DTPA$, $ZnNa_3DTPA$, and $Ca_2DTPA$. In the context of the description of using a stabilizing agent, the term "effective amount" refers to the amount or concentration of a stabilizing agent that is effective in inhibiting the oxidative degradation of (i) rusalatide acetate or (ii) a rusalatide acetate composition, formulation or dosage form that includes Monomer, Dimer or any combination of Monomer and Dimer, or (iii) both (i) and (ii).

The present invention also contemplates that one or more other types of excipients may also be utilized in a rusalatide acetate composition, formulation or dosage form to enhance the stability of (i) rusalatide acetate or (ii) a rusalatide acetate composition, formulation or dosage form that includes Monomer, Dimer or any combination of Monomer and Dimer, or (iii) both (i) and (ii).

As noted above, the present invention contemplates the use of any suitable and pharmaceutically acceptable excipient, for example, as disclosed in the "Handbook of Pharmaceutical Excipients" (Sixth Edition, Pharmaceutical Press and American Pharmacists Association 2009), which is incorporated by reference herein in its entirety.

Some representative examples of other types of excipients include, but are not limited to, binders or binding agents; buffering agents (e.g., to adjust pH); tonicity adjusting agents (e.g., for rusalatide acetate solutions); antiadherents; diluents; glidants; disintegrants; fillers; desiccants; sorbents; hydrophilic lubricants; hydrophobic lubricants; emulsifying agents; flavoring agents; coatings or coating excipients; coloring agents; preservatives; and sweetening agents. Other types of excipients include, but are not limited to, astringents, emollients, hypertonicity agents, oleaginous agents, demulcents, and mucomimetic agents.

Examples of binders include, but are not limited to, celluloses such as microcrystalline cellulose, modified celluloses such as low substituted hydroxypropyl cellulose, hydroxypropyl cellulose, hydroxypropyl methylcellulose, polyethylene oxide, xanthan gum, sugars (such as sucrose, maltodextrin, dextrose), starches such as potato starch or corn starch, polyvinyl alcohol-polyethylene glycol graft copolymer, copovidone, povidone, polyethylene glycol or a combination of suitable binders.

Examples of diluents/fillers include, but not limited to, celluloses, cellulose acetate, microcrystalline cellulose, trehalose, erythritol, silicified microcrystalline cellulose, dextrose, fructose, glyceryl palmitostearate, kaolin, lactitol, lactose, maltitol, mannitol, maltose, pregelatinized starch, sodium chloride, sorbitol, starches, sucrose, glucose, calcium sulphate, dibasic calcium phosphate, talc and xylitol or a combination of one or more diluents.

Examples of glidants include, but are not limited to, calcium phosphate, magnesium trisilicate, silicon dioxide, talc, colloidal silica, calcium silicate, maize starch, powdered cellulose, and colloidal silica anhydrous.

Examples of disintegrants include, but are not limited to, starches, docusate sodium, guar gum, hydroxypropyl cellulose, partially pregelatinized starches, sodium starch glycolate, pregelatinized starch, alginic acid, methylcellulose, sodium alginate, powdered cellulose, croscarmellose sodium, crospovidone, low substituted hydroxypropyl cellulose, magnesium aluminum silicate, or a combination of one or more disintegrants.

Other examples of representative excipients include, but are not limited to, propolis, beeswax, nectar, honey, and royal jelly, any other products or derivatives from bees, including any and all other products or derivatives from honeybees or other bees, or any combination thereof.

It is to be understood that this list of excipients is only a representative list, and it is for illustration purposes only, and it does not limit the scope of the present invention in any way. It is to be understood that any other type of suitable and pharmaceutically acceptable excipient may also be utilized to enhance the stability of (i) rusalatide acetate or (ii) a rusalatide acetate composition, formulation or dosage form that includes Monomer, Dimer or any combination of Monomer and Dimer, or (iii) both (i) and (ii), and in accordance with the methods and systems of the present invention.

Sterility

Sterility is another example of a parameter that can affect stability of (i) rusalatide acetate or (ii) a rusalatide acetate composition, formulation or dosage form that includes Monomer, Dimer or any combination of Monomer and Dimer, or (iii) both (i) and (ii). The present invention contemplates that the sterility and other conditions of a rusalatide acetate composition, formulation or dosage form can be optimized in order to enhance stability.

Impact of Viscosity of a Particular Formulation on Stability

Another example of a parameter that can affect stability of a rusalatide acetate composition, formulation or dosage form is the impact of viscosity of the composition, formulation or dosage form on stability. The present invention contemplates that the viscosity and other conditions of a rusalatide acetate composition, formulation or dosage form can be optimized in order to enhance the stability of (i) rusalatide acetate or (ii) a rusalatide acetate composition, formulation or dosage form that includes Monomer, Dimer or any combination of Monomer and Dimer, or (iii) both (i) and (ii).

Hydrophilic Interactions, Hydrophobic Interactions and Other Interactions with any Components in a Formulation or Pharmaceutical Composition; and Effects of any Materials Used in Containers, Kits, Packaging and/or Storage, on Stability The present invention also contemplates that additional representative parameters that can affect stability of (i) rusalatide acetate or (ii) a rusalatide acetate composition, formulation or dosage form that includes Monomer, Dimer or any combination of Monomer and Dimer, or (iii) both (i) and (ii), include, but are not limited to, hydrophilic interactions, hydrophobic interactions, any other type of chemical, physical or physio-chemical interactions (for instance between the Monomer or Dimer and any components of the formulation, composition or dosage form), or any combination of these interactions.

The present invention also contemplates that the physical and chemical properties of solid substrates or surfaces influence the stability and activity of the Monomer, Dimer, and any combination of Monomer and Dimer. The present invention contemplates, for example, that different hydrophilic or hydrophobic solid substrates or surfaces can be analyzed with regard to their effects on the stability and activity of (i) rusalatide acetate, (ii) a rusalatide acetate composition, formulation or dosage form that includes Monomer, Dimer or any combination of Monomer and Dimer, and (iii) both (i) and (ii). For example, the present invention contemplates analysis of substrates and surfaces comprising moderate hydrophilic mesoporous silica pores versus more hydrophilic surfaces, to analyze and determine their effects on the stability and activity of Monomer, Dimer, and any combination of Monomer and Dimer. Depending on their physical and chemical properties, different materials may have hydrophilic interactions, hydrophobic interactions, or other type of interactions with Monomer, Dimer, or any combination of Monomer and Dimer, which may therefore affect the stability of the Monomer, Dimer, or any combination of Monomer and Dimer. The present invention also contemplates that physical, non-abstract data can be gathered and analyzed for any type of material, including but not limited to any material that is being considered and evaluated for use in containers, kits, packaging or storage of a rusalatide acetate composition, formulation or dosage form. This data can be gathered during any and all preformulation and formulation stages of rusalatide acetate pharmaceutical product development.

The present invention also contemplates that models and simulations can be utilized to analyze and determine the effects of different materials on the stability and activity of (i) rusalatide acetate and (ii) any rusalatide acetate composition, formulation or dosage form that includes Monomer, Dimer or any combination of Monomer and Dimer.

For example, a hydrophobic-polar (H-P) lattice model can be used to gather physical, non-abstract data and analyze the thermal stability of (i) rusalatide acetate and (ii) any rusalatide acetate composition, formulation or dosage form that includes Monomer, Dimer or any combination of Monomer and Dimer, in the presence of different hydrophilic or hydrophobic materials, substrates and surfaces.

The effects of different thicknesses and curvature surfaces (e.g., the surface hydrophilic character inside very small cavities or pores of porous materials), as well as the permeability of different materials to light, can also be analyzed to further evaluate the effects of different materials on the stability and activity of Monomer, Dimer, or any combination of Monomer and Dimer in different formulations, pharmaceutical compositions or dosage forms.

The present invention also contemplates physical, non-abstract gathering of data and analysis with regard to the effects of pore size of different materials, as compared to the hydrodynamic radius of the Monomer or Dimer. In accordance with the present invention, this type of analysis is also very valuable and is useful for taking appropriate steps to enhance the stability of (i) rusalatide acetate or (ii) a rusalatide acetate composition, formulation or dosage form that includes Monomer, Dimer or any combination of Monomer and Dimer, or (iii) both (i) and (ii).

Impact of Exposure to Light on Stability (e.g., Effects of Photolysis and Photo-Oxidation)

As described elsewhere herein, the present invention contemplates that oxidation of rusalatide acetate may occur, including oxidation of Monomer, Dimer, or any combination of Monomer and Dimer. Such oxidation can be induced, for example, by contaminating oxidants, catalyzed by the presence of transition metal ions and also induced by light. Exposure to light is therefore one of the parameters which can be analyzed to determine if there are any effects (for example, caused by photolysis or photo-oxidation) on the stability of rusalatide acetate, and if there is any oxidation of Monomer, Dimer, or any combination of Monomer and Dimer.

As described herein, photostability testing can involve exposure of samples of rusalatide acetate (including Monomer and Dimer), and also exposing both solid and liquid rusalatide acetate dosage forms, to different types of light and intensities of light. By way of example, it is preferred that samples are exposed to a minimum of about 1.2 million lux hours and about 200 watt hours per square meter light. It is also preferred that samples are exposed to white light, and other samples exposed to UV light. Controlled studies are performed in which control samples are not exposed to any light. Also, it is preferred to maintain control of the temperature (i.e., in order to maintain a constant temperature) during exposure to the light, in order to minimize the effect of any temperature changes during exposure.

Any suitable instrument, system or combination of instruments or systems can be used to detect and analyze for any effects of exposure to light on the stability of Monomer, Dimer, or any combination of Monomer and Dimer. One non-limiting example is the use of spectroscopy for analyzing and determining the photostability of Monomer, Dimer, or any combination of Monomer and Dimer. For example, with spectrophotometric characterization, samples containing Monomer, Dimer, or any combination of Monomer and Dimer are exposed to suitable and appropriate levels of UV radiation or UV-Vis radiation, as determined by suitable analytical chemistry methods, and the presence or occurrence of any photodegradation is monitored by using a spectrophotometric method. The present invention contemplates novel approaches, methods, processes and systems for physical, non-abstract analysis of these parameters, and further wherein at least one physical, non-abstract computer-based instrumentation system is operable for performing at least one physical, non-abstract stability optimization procedure based on the analysis such that the stability of (i) rusalatide acetate or (ii) a rusalatide acetate composition, formulation or dosage form that includes Monomer, Dimer or any combination of Monomer and Dimer, or (iii) both (i) and (ii), is enhanced.

Effects of Ions, Salts, and Ionic Strength on Rusalatide Acetate Conformation and Stability The present invention also contemplates additional representative parameters that can affect stability of (i) rusalatide acetate or (ii) a rusalatide acetate composition, formulation or dosage form that includes Monomer, Dimer or any combination of Monomer and Dimer, or (iii) both (i) and (ii). Such additional representative parameters include, but are not limited to, the effects of different ions (for example, one or more cations or anions), one or more salts, the effects of changes in ionic strength, for instance during one or more preformulation or formulation processes or stages during preparation of a rusalatide acetate composition, formulation or dosage form. For example, monovalent salts, such as sodium chloride, may affect peptide stability by modifying the ionic strength of a solution containing the peptide. The present invention also contemplates novel approaches, methods, processes and systems for physical, non-abstract analysis of these parameters, and further wherein at least one physical, non-abstract computer-based instrumentation system is operable for performing at least one physical, non-abstract stability optimization procedure based on the analysis such that the stability of (i) rusalatide acetate or (ii) a rusalatide acetate composition, formulation or dosage form that includes Monomer, Dimer or any combination of Monomer and Dimer, or (iii) both (i) and (ii) is enhanced.

Binding to Transition Metals; Oxidation Catalyzed by the Presence of Transition Metal Ions The present invention also contemplates that oxidation of Monomer, Dimer, or any combination of Monomer and Dimer can be induced by contaminating oxidants, catalyzed by the presence of transition metal ions or also induced by light. These are all additional representative parameters that can affect the stability of (i) rusalatide acetate or (ii) a rusalatide acetate composition, formulation or dosage form that includes Monomer, Dimer or any combination of Monomer and Dimer, or (iii) both (i) and (ii).

The present invention contemplates that purity and stability of rusalatide acetate can be enhanced by detection and removal of any transition metal impurities, including any redox-active transition metal impurities. The term "redox-active transition metal impurities" is intended to include any transition metals that are contaminants or impurities, and which are capable of interacting with rusalatide acetate through a redox mechanism, i.e., through a reduction or oxidation process in which rusalatide acetate is reduced or oxidized by one or more of the transition metal contaminants or impurities. To maintain and enhance the stability of rusalatide acetate, it is therefore desired to remove any and all redox-active transition metal impurities. Specific examples of redox-active transition metal impurities include, but are not limited to, iron (Fe), cobalt (Co), copper (Cu), aluminum (Al), and manganese (Mn). During preparation and manufacturing of a rusalatide acetate formulation, pharmaceutical composition or dosage form, steps can be taken to detect and remove any such transition metal impurities, thus enhancing purity and stability of rusalatide acetate.

The present invention also contemplates careful screening of chelating agents to select safe and effective chelating agents for reducing or preventing metal-catalyzed oxidation of rusalatide acetate. One or more safe and effective chelating agents can be used as needed or appropriate in pharmaceutical compositions, formulations and dosage forms comprising rusalatide acetate. The present invention also contemplates other suitable approaches, methods, processes and systems for physical, non-abstract analysis of these parameters, and further wherein at least one physical, non-abstract computer-based instrumentation system is operable for performing at least one physical, non-abstract stability optimization procedure based on the analysis such that the stability of a rusalatide acetate composition, formulation or dosage form is enhanced, wherein the composition, formulation or dosage form includes Monomer, Dimer or any combination of Monomer and Dimer.

Impact of Temperature, Time, Concentration (e.g., Concentration of Rusalatide Acetate Peptide), and the Order of Mixing on Stability The present invention also contemplates that additional representative parameters can affect stability of (i) rusalatide acetate or (ii) a rusalatide acetate composition, formulation or dosage form that includes Monomer, Dimer or any combination of Monomer and Dimer, or (iii) both (i) and (ii). These include, but are not limited to, the impact of temperature; time (for example, the duration of time when mixing excipients during product development; storage time when storing a batch of a rusalatide acetate composition; concentration of rusalatide acetate; the order of mixing of components (including, for example, the order of mixing of various excipients) that are used in preparing rusalatide acetate compositions, formulations and dosage forms; or any combination thereof.

With regard to the concentration of rusalatide acetate peptide in a pharmaceutical composition, formulation or dosage form, it is contemplated that analytical techniques can also be used to determine whether any unwanted aggregates are formed (for example, unwanted amorphous aggregates of peptide) at different concentrations of rusalatide acetate peptide, and appropriate steps can be taken to reduce or eliminate such aggregates, since such aggregates might adversely impact the stability of rusalatide acetate. Also, suitable techniques can be used to determine whether there is any unwanted adsorption of rusalatide acetate peptide to a surface (e.g, to the surface of a container used in manufacturing or product development) at different concentrations of rusalatide acetate peptide, and appropriate steps can be taken to reduce or eliminate such adsorption to a surface, since such adsorption might adversely impact the stability of rusalatide acetate.

Process and manufacturing conditions (for example, at both preformulation and formulation stages), including but not limited to temperature, time (for instance, duration of time when mixing excipients during product development), storage time when storing a batch of a rusalatide acetate composition, concentration of rusalatide acetate, and the order of mixing of components (including, for example, the order of mixing of various excipients) can all be optimized in order to enhance the stability of rusalatide acetate in a pharmaceutical composition, formulation or dosage form.

The present invention also contemplates novel approaches, methods, processes and systems for physical, non-abstract analysis of these parameters, and further wherein at least one physical, non-abstract computer-based instrumentation system is operable for performing at least one physical, non-abstract stability optimization procedure based on the analysis such that the stability of a rusalatide acetate composition, formulation or dosage form is enhanced, wherein the rusalatide acetate composition, formulation or dosage form includes Monomer, Dimer or any combination of Monomer and Dimer.

Effects of any Contaminants or Impurities on Stability, e.g., Presence of any Contaminants or Impurities in a Formulation, Composition or Dosage Form As described elsewhere herein, the present invention contemplates that oxidation of (i) rusalatide acetate or (ii) a rusalatide acetate composition, formulation or dosage form that includes Monomer, Dimer or any combination of Monomer and Dimer, or (iii) both (i) and (ii) can be induced by contaminating oxidants, catalyzed by the presence of transition metal ions or induced by light. These are all representative parameters that can affect the stability of (i) rusalatide acetate or (ii) a rusalatide acetate composition, formulation or dosage form that includes Monomer, Dimer or any combination of Monomer and Dimer, or (iii) both (i) and (ii). The present invention contemplates novel approaches, methods, processes and systems for physical, non-abstract analysis of the parameters, and further wherein at least one physical, non-abstract computer-based instrumentation system is operable for performing at least one physical, non-abstract stability optimization procedure based on the analysis such that the stability of a rusalatide acetate composition, formulation or dosage form is enhanced, wherein the rusalatide acetate composition, formulation or dosage form includes Monomer, Dimer or any combination of Monomer and Dimer.

Potential Effects on Stability Produced by Agitation, Lyophilization, or Other Process Steps and Procedures, e.g., During the Process of Preparing a Rusalatide Acetate Formulation The present invention also contemplates that suitable techniques can be utilized to analyze for any potential effects on stability (i.e., stability of rusalatide acetate) produced by agitation, lyophilization, or other process steps and procedures, e.g., during the process of preparing a rusalatide acetate formulation, dosage form or pharmaceutical composition.

Enhancing Stability by Protection Against Cleavage of the Asp-Pro Bond in Rusalatide Acetate It has been found that peptides containing an Asp-Pro bond may cleave under certain acidic conditions such as, for example, 10% acetic acid in water. Therefore, to minimize the likelihood of cleavage of the Asp-Pro bond in rusalatide acetate, the present invention contemplates that it is preferred to avoid the use of 10% acetic acid in water.

Enhancing Stability of Rusalatide Acetate by Minimizing the Effects of Hydrolysis The present invention also contemplates that appropriate steps can be taken to minimize the effects of hydrolysis, and thus enhance the stability of (i) rusalatide acetate or (ii) a rusalatide acetate composition, formulation or dosage form that includes Monomer, Dimer or any combination of Monomer and Dimer, or (iii) both (i) and (ii), since hydrolysis can affect peptides containing Asp in the sequence, which can be susceptible to dehydration to form a cyclic imide intermediate.

According to other embodiments, the present invention also contemplates the introduction of certain protecting groups to protect Asp residues from degradation. For instance, the invention contemplates the use of Asp(OcHx) which can provide protection against succinimide formation.

Enhancing Stability of Rusalatide Acetate by the Use of One or More Peptidase Inhibitors In a preferred embodiment, a rusalatide acetate composition, formulation or dosage form is administered with one or more peptidase inhibitors that specifically inhibit peptidase cleavage of rusalatide acetate.

The present invention also contemplates that suitable methods can be used for the in vitro assessment of rusalatide acetate peptide stability in plasma, or in suitable in vitro assays, which can provide useful additional information for predicting the likely in vivo stability of the rusalatide acetate peptide.

The present invention provides stabilized pharmaceutical compositions, dosage forms and formulations in which the stability of rusalatide acetate is enhanced.

The present invention contemplates stabilized pharmaceutical compositions, dosage forms and formulations in which (1) rusalatide acetate is present entirely as the Monomer, or (2) the Monomer accounts for substantially all, or a majority, of rusalatide acetate present in the stabilized pharmaceutical compositions, dosage forms and formulations.

The present invention also contemplates stabilized pharmaceutical compositions, formulations and dosage forms in which (1) rusalatide acetate is present entirely as the Dimer, or (2) the Dimer accounts for substantially all, or a majority, of rusalatide acetate present in the stabilized pharmaceutical compositions, dosage forms and formulations.

Representative Examples of Stability Optimization Procedures

As described herein, the present invention contemplates performing at least one physical, non-abstract stability optimization procedure based on analysis of one or more parameters (i.e., parameters that affect stability) such that the stability of a rusalatide acetate composition, formulation or dosage form is enhanced, wherein the rusalatide acetate composition, formulation or dosage form includes Monomer, Dimer or any combination of Monomer and Dimer.

Examples of procedures for analysis of these parameters include, but are not limited to, stability assays or stability tests that are physically performed in a laboratory, or any other suitable analytical procedures that can be used for the analysis of stability. The present invention contemplates, for example, using high-performance liquid chromatography (HPLC) for the assessment of stability (e.g., use in stability assays) and to analyze samples of rusalatide acetate for degradant formation (e.g., formation of degradation products). Steps can be taken to analyze for any degradation of Monomer or Dimer. Further analysis can be performed by mass spectrometry or other suitable analytical techniques.

In preferred embodiments, the present invention contemplates that all stability assays will preferably be performed at least in triplicates.

In preferred embodiments, the present invention also contemplates that further analysis can be performed using, for example, a humidity-corrected Arrhenius equation along with an isoconversion method to help predict optimal conditions for stability, shelf-life and storage of (i) rusalatide acetate and (ii) any rusalatide acetate composition, formulation or dosage form that includes Monomer, Dimer or any combination of Monomer and Dimer.

When Desired to Stabilize the Monomer: Use of Dimerization Inhibitors

When it is desired to stabilize the Monomer, the present invention also contemplates methods for obtaining formulations comprising Monomer that is essentially free of Dimers. rusalatide acetate has been found to retain its monomeric form essentially free of dimers in the presence of a dimerization inhibitor such as a chelating agent or a pharmaceutically acceptable thiol-containing compound, e.g., greater than 90% free by weight over 2-month time period and preferably greater than 95% free by weight over 2-month time period. The chelating agent and the thiol-containing compound can be used together or separately to prevent or reduce dimerization. An antioxidant optionally can be used in combination with the chelating agent or the thiol-containing compound. A "chelating agent," as used herein, is preferably a compound having multiple sites (two, three, four or more) which can simultaneously bind to a metal ion or metal ions such as, for example, lead, cobalt, iron or copper ions. The binding sites typically comprise oxygen, nitrogen, sulfur or phosphorus. For example, salts of EDTA (ethylenediaminetetraacetic acid) can form at least four to six bonds with a metal ion or metal ions via the oxygen atoms of four acetic acid moieties (—CHZG(O)O~) and the nitrogen atoms of ethylenediamine moieties (>N—CHZ—CHZ—N<) of EDTA. It is understood that a chelating agent can also include a polymer which has multiple binding sites to a metal or metal ions. Preferably, a chelating agent of the invention is non-toxic and does not cause unacceptable side effects at the dosages being administered. As a chelating agent of the invention, a copper-chelating agent is preferable. A "copper-chelating agent" refers to a chelating agent which can bind to a copper ion or copper ions. Examples of a copper-chelating agent include, but are not limited to, ethylenediaminetetraacetic acid (EDTA), penicillamine, trientine, N,N-diethyldithiocarbamate (DDC), 2,3,2'-tetraamine (2,3,2'-tet), neocuproine, N,N,N; N-tetrakis(2-pyridylmethyl)ethylenediamine (TPEN), 1,10-phenanthroline (PHE), tetraethylenepentamine (TEPA), triethylenetetraamine and tris(2-carboxyethyl) phosphine (TCEP). Additional chelating agents are diethylenetriaminepentacetic acid (DTPA) and bathophenanthroline disulfonic acid (BPADA). EDTA is a preferred chelating agent. Typical amounts of a chelating agent present in the pharmaceutical compositions of the instant invention are, for example, within a range of between about 0.00001% and about 0.1% by weight, and preferably between about 0.0001% and about 0.05% by weight. A "pharmaceutically acceptable thiol-containing compound", as used herein, is a compound which comprises at least one thiol (—SH) group and which does not cause unacceptable side effects at the dosages which are being administered. Examples of a pharmaceutically acceptable thiol-containing compound include, but are not limited to, thioglycerol, mercaptoethanol, thioglycol, thiodiglycol, cysteine, thioglucose, dithiothreitol (DTT) and dithio-bis-maleimidoethane (DTME). According to certain embodiments of the invention, between about 0.001% and about 5% by weight, and preferably between about 0.05% and about 1.0% by weight, of a pharmaceutically acceptable thiol-containing compound is present in the pharmaceutical compositions and formulations of the invention. Other representative examples of commonly used chelating agents, however, do not contain a thiol group. It is also understood that the pharmaceutical compositions of the instant invention can include more than one chelating agent, thiol-containing compound or antioxidant. That is, for example, a chelating agent can be used either alone or in combination with one or more other suitable chelating agents.

Additional Representative Parameters that can be Analyzed

The present invention contemplates that any suitable analytical method and characterization method, or combination of analytical methods and characterization methods, can be employed and utilized to analyze and characterize (i) rusalatide acetate or (ii) a rusalatide acetate composition, formulation or dosage form that includes Monomer, Dimer or any combination of Monomer and Dimer, or (iii) both (i) and (ii). The data and information that is collected and gathered from these analytical methods and characterization methods can be used, in accordance with the systems and methods of the present invention, for enhancing the stability and optimizing the stability of (i) rusalatide acetate or (ii) a rusalatide acetate composition, formulation or dosage form that includes Monomer, Dimer or any combination of Monomer and Dimer, or (iii) both (i) and (ii), for any intended use including clinical uses and applications.

According to a preferred embodiment of the present invention, analytical methods and characterization methods can be used to collect and gather additional information about (i) rusalatide acetate or (ii) a rusalatide acetate composition, formulation or dosage form that includes Monomer, Dimer or any combination of Monomer and Dimer, or (iii) both (i) and (ii). This information can be used to further analyze, characterize and evaluate the stability of (i) rusalatide acetate or (ii) a rusalatide acetate composition, formulation or dosage form that includes Monomer, Dimer or any combination of Monomer and Dimer, or (iii) both (i) and (ii), under any conditions and at any stage, for example but not limited to the following:

(1) during synthesis of (i) rusalatide acetate or (ii) a rusalatide acetate composition, formulation or dosage form that includes Monomer, Dimer or any combination of Monomer and Dimer;

(2) at a preformulation stage or formulation stage;

(3) during manufacturing of a rusalatide acetate composition, formulation or dosage form that includes Monomer, Dimer or any combination of Monomer and Dimer;

(4) during storage of one or more batches of a rusalatide acetate composition, formulation or dosage form that includes Monomer, Dimer or any combination of Monomer and Dimer; and (5) just prior to use for one or more clinical applications.

These are all non-limiting examples. This information, which can be used to further analyze, characterize and evaluate the stability of (i) rusalatide acetate or (ii) a rusalatide acetate composition, formulation or dosage form that includes Monomer, Dimer or any combination of Monomer and Dimer, or (iii) both (i) and (ii), can also further be used in combination with the information gathered from analysis of the parameters described herein, including but not limited to atmospheric oxygen, moisture content, relative humidity, type of carrier, pH, temperature, and other parameters described herein that can affect stability of (i) rusalatide acetate or (ii) a rusalatide acetate composition, formulation or dosage form that includes Monomer, Dimer or any combination of Monomer and Dimer, or (iii) both (i) and (ii).

Any number of additional parameters or attributes can be analyzed including, but not limited to, parameters or attributes that help to characterize the identity, strength, stability, shelf-life, solubility, hygroscopicity, degradation profile, potency or purity of (i) rusalatide acetate or (ii) a rusalatide acetate composition, formulation or dosage form that includes Monomer, Dimer or any combination of Monomer and Dimer, or (iii) both (i) and (ii). These additional parameters or attributes can be analyzed at any stage, for example, at any stage of synthesis of rusalatide acetate, and throughout the manufacturing process including any preformulation or formulation stages (e.g., for both in-process and final product manufacturing of a rusalatide acetate formulation, pharmaceutical composition or dosage form). These additional parameters or attributes can also be analyzed for any type of rusalatide acetate formulation, pharmaceutical composition or dosage form (for example, but not limited to, a solid, liquid, gel, cream, ointment, a lyophilized preparation or formulation, or any other type of formulation, composition or dosage form and also for any route of delivery or administration for clinical use). Any number of tests can be performed, for example, to enable statistical analysis and to meet requirements for product development for clinical use, and for any other regulatory requirements. For instance, during the development of a rusalatide acetate formulation, tests can be performed to analyze for impurities, and process steps can be taken in order to make sure that impurity levels in a final batch or final product are below the acceptable limits or threshold required by regulations. Some examples of these additional parameters or quality attributes include, but are not limited to, the following:

appearance of the peptide—information about this parameter or attribute may be gathered, for example, by visual inspection of the peptide or using suitable instrumentation;

peptide content (for instance, during synthesis of the peptide)—information about this parameter or attribute can be gathered, for example, by quantitative amino acid analysis; elemental analysis; Kjeldahl analysis, and HPLC using chemiluminescence nitrogen detector (CLND) can also be used;

presence of any organic impurities or any degradation impurities—information about this parameter or attribute can be gathered, for example, by HPLC methods including but not limited to reversed phase HPLC (RP-HPLC), ion-exchange HPLC (IEX-HPLC), size exclusion chromatography (SEC or SEC-HPLC), ultra-high-performance liquid chromatography (UHPLC), etc;

presence of any residual solvents (e.g., organic solvents) or presence of any other non-peptide impurities (for instance, from synthesis or from a preformulation or formulation stage)—information about this parameter or attribute can be gathered, for example, by gas chromatography;

presence of other anions (inorganic impurities)—information about this parameter or attribute can be gathered, for example, by ion chromatography;

presence of fluoride as an inorganic impurity—information about this parameter or attribute can be gathered, for example, by ion selective electrode or ion chromatography;

presence of any small molecule impurities or any potential genotoxic impurities—information about this parameter or attribute can be gathered by suitable detection assays and methods;

presence of elemental impurities (inorganic impurities)—information about this parameter or attribute can be gathered, for example, by inductively coupled plasma mass spectrometry (ICP-MS);

presence of any counterions (which is a parameter or attribute that can affect rusalatide acetate stability)— counterion quantification analysis can be used to measure and quantify the presence of counterions, and analyze the effects of counterions on peptide stability, e.g., stability of rusalatide acetate; examples of counterions include, but are not limited to, sodium, calcium and chloride ions; information about counterions can be gathered, for example, by AgNO$_3$ titration or ion chromatography, or by reversed phase HPLC (RP-HPLC); other methods and procedures, for example united-atom molecular dynamics simulations, can also be used to analyze and determine effects of counterions on peptide stability.

analysis of water content—information about this parameter or attribute can be gathered, for example, by a coulometric method, or using Karl Fischer titration;

analysis of mass balance (including peptide content, counterion content and water content) can also be performed;

analysis of bioburden—information about this parameter or attribute can be gathered, for example, by methods to determine total aerobic microbial count (TAMC) and the total combined yeasts and molds count (TYMC);

analysis for presence of any endotoxins (including but not limited to any bacterial endotoxins)—information about this parameter or attribute can be gathered, for example, by suitable detection assays The present invention contemplates that, for an analysis of bioburden, any suitable procedures can be carried out for bioburden testing. The term "bioburden" as used herein is broadly intended to refer to the total quantity, number or amount of microorganisms, including but not limited to bacteria, which are present in a rusalatide acetate composition, dosage form or formulation, and which includes both sterilized and non-sterilized microorganisms.

The term "bioburden testing" as used herein is broadly intended to refer to any microbial testing that is performed on a rusalatide acetate composition, dosage form or formulation, in which the testing is used to measure the bioburden that is present in the composition, dosage form or formulation.

The present invention also contemplates that any other suitable analytical methods can also be used to analyze and characterize (i) rusalatide acetate and (ii) any rusalatide acetate composition, formulation or dosage form that includes Monomer, Dimer or any combination of Monomer and Dimer. Examples of such analytical methods include, but are not limited to, high performance liquid chromatography (HPLC), reversed phase HPLC (RP-HPLC), high performance liquid chromatography-ion exchange chromatography (HPLC-IEX), high performance liquid chromatography-size exclusion chromatography (HPLC-SEC), ultra-high-performance liquid chromatography (UHPLC); mass spectrometry analysis, for instance, analysis by high performance mass spectrometry (HPMS), high resolution mass spectrometry (HRMS), UHPLC-HRMS, liquid chromatography-mass spectrometry (LC-MS), two-dimensional LC-MS, tandem mass spectrometry, or liquid chromatography-tandem mass spectrometry (LC-MS/MS); sequence analysis; amino acid analysis; peptide mapping; NMR spectroscopy; infrared spectroscopy; peak purity analysis, for instance, by LC-MS; analysis of enantiomeric purity (chiral amino acid analysis by gas chromatography-mass spectrometry (GC-MS), or chiral GC-MS; ion chromatography; optical rotation analysis; higher order structure (HOS) analysis, for example, by circular dichroism (CD), nuclear magnetic resonance (NMR), or Fourier transform infrared spectroscopy (FTIR); and any other suitable analytical methods that help to analyze and characterize the identity, strength, stability, shelf-life, solubility, hygroscopicity, degradation profile, potency or purity of (i) rusalatide acetate or (ii) a rusalatide acetate composition, formulation or dosage form that includes Monomer, Dimer or any combination of Monomer and Dimer, or (iii) both (i) and (ii). It is also contemplated that multiple, orthogonal (statistically independent) methods can be used. All analytical methods used, as described herein, can undergo rigorous validation and are preferably validated, at a minimum, for specificity, robustness and LOD (limit of detection) or limit of quantitation (LOQ).

In addition to the analytical methods described herein, one or more suitable bioassays can also be used to further characterize (i) rusalatide acetate and (ii) any rusalatide acetate composition, formulation or dosage form that includes Monomer, Dimer or any combination of Monomer and Dimer.

If any impurities, contaminants or degradation products are detected, e.g., during a process of preparing a rusalatide acetate formulation, pharmaceutical composition or dosage form, for instance in production batches or clinical-grade batches, steps can be taken to identify the impurities, contaminants or degradation products. Moreover, steps can be taken to analyze the impurities, contaminants or degradation products for any potential effects on physicochemical properties, biological activity or immunogenicity risk of the rusalatide acetate formulation, pharmaceutical composition or dosage form. Suitable methods can be used for identification, quantitation and analysis if there are co-eluting peaks (for example, co-elution of impurities with each other, or if there is coelution of impurities with the product). In certain embodiments, two-dimensional LC-MS can be used to help facilitate the identification of impurities.

Throughout the entire process, e.g., from peptide synthesis through all stages of rusalatide acetate product development (including but not limited to purification, isolation, formulation or dosage form manufacturing, batch production, stability testing, etc), it is preferred that one or more analytical methods can also be used to detect for the presence of any product-related impurities (such impurities, identified or unidentified, may, for example, originate from one or more raw materials). Representative examples of such product-related impurities include, but are not limited to, one or more of the following, or any combination thereof: insertion sequences, substitution sequences, deletion sequences, truncation sequences, backbone cleavage, diastereomers, fragment coupling, oxidation, β-Asp formation in Asp or Asn sequences, disulfide modification, aggregation or any functional group modifications (for example, but not limited to, acetylation or deamidation), as well as any modifications caused by excipients (for example, any degradation products from PLGA or PEG).

Suitable techniques and procedures can also be utilized to analyze for potential aggregation of rusalatide acetate during the process of developing and evaluating different dosage forms, compositions and formulations. Since aggregation of rusalatide acetate peptide can affect stability, including but not limited to physical stability of rusalatide acetate, it is contemplated that steps can be taken during preformulation and formulations stages to reduce and preferably eliminate any potential aggregation of rusalatide acetate. Preferably, techniques can be used to analyze for any type of aggregation of rusalatide acetate peptides including, but not limited to, amorphous aggregates, aggregates that form in solution, or aggregates that form on surfaces due to adsorption. One example of a technique that can be used to detect for aggregates is the use of atomic force microscopy. In one non-limiting example, atomic force microscopy can be used to detect whether there are any aggregates of rusalatide acetate formed after incubation in water for one week at room temperature. This is just one non-limiting example, and atomic force microscopy or other suitable techniques can be used to detect for the presence of aggregates under different conditions, including but not limited to temperature, pH, presence of one or more excipients, etc.

It is also contemplated that different structure-activity analyses, such as for example structure-activity relationship (SAR) or quantitative structure activity relationship (QSAR) studies, can also be used to further analyze rusalatide acetate, and that steps can be taken to optimize and enhance stability, and reduce or eliminate the presence of any aggregates.

It is also contemplated that reduction and preferably elimination of impurities, contaminants and degradation products will also reduce any potential for toxicity or immunogenicity that might otherwise be caused by such impurities, contaminants and degradation products. Accordingly, the rusalatide acetate pharmaceutical compositions, dosage forms and formulations manufactured in accordance with the present invention will have further significant advantages especially in terms of safety and efficacy.

As used throughout the description herein, the terms "impurities", "contaminants" and "degradation products" are intended to include identified or unidentified impurities, contaminants and degradation products.

The present invention also contemplates that forced degradation or stress testing can also be utilized to help predict, evaluate and optimize the stability and shelf-life of rusalatide acetate compositions, formulations and dosage forms. As used herein, the term "forced degradation" is intended to refer to one or more processes that involve degradation of drug products (e.g., rusalatide acetate, including Monomer and Dimer) under conditions that are typically more severe in intensity than accelerated conditions, and these processes generate degradation products which can be analyzed and evaluated to determine the stability of the drug product. For example, forced degradation can include any type of stress testing and purposeful degradation. Purposeful degradation is useful for predicting the stability of a rusalatide acetate in a composition, formulation or dosage form, in addition to effects on purity, potency, and safety. In one non-limiting example of forced degradation which includes stress testing, a rusalatide acetate composition, formulation or dosage form is exposed to various stress conditions that include, but are not limited to, exposure to light, heat, repeated changes in temperature (e.g., after repeated freeze-thaw cycles), stress conditions that are prone to cause oxidation, stress conditions that are prone to cause hydrolysis, exposure to one or more chemical agents, etc. Photostability stress testing can be performed, for example, according to the International Conference on Harmonization (ICH) guidelines. This approach can be used to further evaluate the stability of rusalatide acetate (including Monomer and Dimer).

Regarding the study protocols, it is contemplated that forced degradation studies, including any type of stress testing and purposeful degradation, are preferably repeated as many times as necessary to give results that can be analyzed for statistical purposes. Moreover, for the study protocols, proper controlled studies will also be performed, in which a certain number of rusalatide acetate samples are stressed (exposed to various stress conditions), and the results are compared to results from control rusalatide acetate samples that are not stressed (not exposed to the stress conditions). All the impurities, degradation products, etc, of the unstressed samples and the stressed samples are analyzed.

It is preferred that stress testing is performed to achieve purposeful degradation that is predictive of both long-term storage conditions and accelerated storage conditions. Preferably, stress testing is performed to achieve degradation between about five (5) percent to about twenty (20) percent degradation of rusalatide acetate (including Monomer and Dimer).

Preferably, stress testing can also include photostability testing, i.e. by exposing samples of rusalatide acetate (including Monomer and Dimer), and also exposing both solid and liquid rusalatide acetate dosage forms, to different types and intensities of light. By way of example, it is preferred that samples are exposed to a minimum of about 1.2 million lux hours and about 200 watt hours per square meter light. It is also preferred that samples are exposed to white light, and other samples exposed to UV light. Controlled studies are performed in which control samples are not exposed to any light. Also, it is preferred to maintain control of the temperature (i.e., in order to maintain a constant temperature) during exposure to the light, in order to minimize the effect of any temperature changes during exposure. For the analysis, it is preferred that the light-exposed samples should be analyzed for any changes in physical properties, including but not limited to any changes in clarity, appearance, color of a solution (for liquid rusalatide acetate dosage forms), etc.

Forced degradation analysis refers to the comprehensive analysis that is performed for analyzing the effects of forced degradation, including various stress conditions and purposeful degradation, on the stability of rusalatide acetate (including Monomer and Dimer). Forced degradation analysis can also utilize any number of suitable analytical techniques, e.g., for measuring and analyzing the effects of forced degradation. Examples of such analytical techniques include, but are not limited to, mass balance calculations, mass spectral analysis, etc. In addition, forced degradation analysis also includes analyzing the information from the various stress conditions and purposeful degradation in order to better understand the impurity profile, identify degradation products and extent of degradation, and time course of degradation (i.e., degradation as measured over different time intervals) of the rusalatide acetate (including Monomer and Dimer) after exposure to the various stress conditions. Forced degradation analysis also provides important information about any degradation products that are formed due to drug-excipient interactions, in addition to information for setting specifications, the development of analytical methods, and design of more stable rusalatide acetate compositions, formulations and dosage forms under a quality-by-design (QbD) paradigm. This information obtained from the forced degradation analysis can also be used for selecting conditions during manufacturing and preparation of a rusalatide acetate composition, formulation or dosage form, in order to further enhance and optimize the stability of rusalatide acetate during preparation of the composition, formulation or dosage form. Also, based on the results of the forced degradation analysis, the results can be used for improvements in the manufacturing and storage process, product handling, and developing enhanced analytical methods for measuring stability.

According to one non-limiting example, a rusalatide acetate composition, formulation or dosage form can undergo various types of stress testing. The conditions for stress testing can also be varied to evaluate the effects of different stress conditions, e.g., at different temperatures, length of times, etc. For example, different formulations can be stress-tested at 40 degrees Celsius over a time course of five days, ten days, twenty days, or other periods of time. This is just one example, and other conditions (e.g., different temperatures; different periods of time; or one or more other types of stressors, including other external stimuli) can also be used during stress testing. Stress testing can of course be performed using controlled study designs, for example, (i) evaluating the effects of thermal exposure (at a wide range of temperatures) on a specific formulation that contains Monomer, Dimer, or any combination of Monomer and Dimer, compared to (ii) a control, i.e., evaluating the effects of the same thermal exposure (at the same range of temperatures) on the same formulation that contains placebo instead of rusalatide acetate.

It is to be understood that the present invention contemplates that all processes, methods, studies, experiments, etc. as described throughout this entire patent application can be performed in a controlled manner (i.e., using proper controls, for statistical analysis), and also conducted in such a manner to meet all regulatory requirements for pharmaceutical product development as required by the U.S., Europe, or another nation, region, or international agency.

Information gathered from stress testing can also be used to analyze for any potential degradation of (i) rusalatide acetate or (ii) a rusalatide acetate composition, formulation or dosage form that includes Monomer, Dimer or any combination of Monomer and Dimer, or (iii) both (i) and (ii), as well as potential degradation of any excipients. Stress testing can thus provide valuable information to further enhance and optimize shelf-life and stability, including the photo-stability, thermal stability and chemical stability of a rusalatide acetate composition, formulation or dosage form. Stress testing can be performed under conditions that meet regulatory and product development requirements.

If oxidation (for instance, produced during stress testing or forced degradation) is determined to cause degradation of (i) rusalatide acetate or (ii) a rusalatide acetate composition, formulation or dosage form that includes Monomer, Dimer or any combination of Monomer and Dimer, or (iii) both (i) and (ii), then different antioxidants can be evaluated to determine if one or more antioxidants enhance shelf-life and stability by reducing oxidative degradation. If oxidation causes degradation via production of free radicals, the free radicals or radical intermediates can be identified. For the detection and monitoring of free radicals or radical intermediates, electron paramagnetic resonance (EPR) spectroscopy or other suitable techniques and analytical methods (reaction monitoring, etc) can be used. Studies can also be performed to evaluate rates of oxidation, e.g., using temporal analysis (for instance, measuring free radical production over a certain time course). The effectiveness and efficiency of one or more antioxidants to reduce, quench or scavenge free radicals can also be evaluated across a range of concentrations using suitable assays.

Additional Representative Embodiments

Furthermore, in other embodiments, the stability of the Monomer or Dimer may be enhanced using "peptidomimetics". As used herein the term "peptidomimetic" refers to a compound that comprises the same general structure of a corresponding polypeptide, in this case Monomer or Dimer, but which includes modifications that increase its stability or biological function. For instance, the peptidomimetic can be a "reverso" analog of a given peptide, which means that the peptidomimetic comprises the reverse sequence of the peptide. In another embodiment, the peptidomimetic can comprise one or more amino acids in a "D" configuration (e.g., D-amino acids), providing an "inverso" analog. Peptidomimetics also include peptoids, wherein the side chain of each amino acid is appended to the nitrogen atom of the amino acid as opposed to the alpha carbon. Peptoids can, thus, be considered as N-substituted glycines which have repeating units of the general structure of $NRCH_2CO$ and which have the same or substantially the same amino acid sequence as the corresponding polypeptide.

In another embodiment, the peptide or peptidomimetic also can comprise synthetic, non-naturally occurring amino acids. Such synthetic amino acids include, for example, but are not limited to, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, am inomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β.-diaminopropionic acid, homophenylalanine, and α-tert-butylglycine.

Other substitutions are also permissible and can be determined empirically or in accord with other known conservative or non-conservative substitutions. Moreover, the following eight groups each contain amino acids that can typically be taken to define conservative substitutions for one another:
1) Alanine, Glycine;
2) Aspartic acid, Glutamic acid;
3) Asparagine, Glutamine;
4) Arginine, Lysine;
5) Isoleucine, Leucine, Methionine, Valine;
6) Phenylalanine, Tyrosine, Tryptophan;
7) Serine, Threonine; and
8) Cysteine, Methionine In certain embodiments, the peptide or peptidomimetic can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used. In certain embodiments, rusalatide acetate can be synthesized by a solid phase peptide synthesis (for example, but not limited to, BOC or FMOC) method, or in other embodiments by solution phase synthesis. The present invention also contemplates that rusalatide acetate can be synthesized by other suitable techniques including, e.g., combinations of the other methods of peptide synthesis described herein. Methods of recombinantly producing peptides and peptidomimetics can also be used.

Peptides of the present invention having a chiral center may exist in and be isolated in optically active and racemic forms. The present invention encompasses any racemic, optically-active, diastereomeric, polymorphic, or stereoisomeric form, or mixtures thereof, of a peptide of the invention, which possess the useful properties described herein.

In one embodiment, the peptides are prepared in optically active form by asymmetric synthesis using the processes described herein or synthetic transformations known to those skilled in the art.

Other methods to obtain optically active materials are known in the art, and include at least the following representative methods:

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state;

iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xii) extraction with chiral solvents—a technique whereby the enantiomers are separated by virtue of preferential dissolution of one enantiomer into a particular chiral solvent; or xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

New, stable rusalatide acetate compositions, formulations and dosage forms, including 23 amino acid monomer ("Monomer"), dimer ("Dimer") of two 23 amino acid Monomers, or any combination of Monomer and Dimer which may be present at any time in any ratio, proportion or percentage of the compositions, formulations and dosage forms, are also contemplated. The new stable compositions, formulations and dosage forms, or new stable "drugable form", can be achieved, for example, by providing new crystalline forms of rusalatide acetate. Under the proper circumstances, another advantage of these new stable compositions, formulations and dosage forms is achieving some modulation of the pharmacological effects. Although APIs (active pharmaceutical ingredients) in general have been recognized to form crystalline polymorphs, solvates, hydrates and amorphous forms, there is little knowledge about which form the Monomer and Dimer take. Just as a polymorph, solvate, hydrate or amorphous form of an API can modulate stability, solubility, and hygroscopicity, a peptide crystal can modulate those same properties.

As used herein, the term "drugable form" is defined as any form (for example, a salt, amorphous crystal, solution, dispersion, mixture, etc) that the Monomer or Dimer might take which still can be formulated into a pharmaceutical formulation or pharmaceutical composition for use in treating a disease or a symptom.

In certain non-limiting embodiments of the invention, a polymorph of the Monomer or Dimer may be stable under relative humidity stress conditions, up to its melting point.

In certain non-limiting embodiments of the invention, polymorphs of the Monomer or Dimer may be capable of existing in several different crystalline forms, which may for example be referred to as Form A through Form X, and an amorphous product. There are many known methods used to produce crystalline forms, for example but not limited to:

a) one method which involves crystallizing from the Monomer or Dimer using protic solvents, for example ethanol or ethanol/water mixtures, or from a polar solvent, for example dimethylsulfoxide/water. In one example, Form A may be a monohydrate, and is the most stable of the various polymorphs at ambient temperatures. It is stable under relative humidity stress conditions up to its melting point;

b) another method involves evaporating the Monomer or Dimer under vacuum.

Various techniques can be used to analyze the various forms of the Monomer or Dimer. For example, such techniques include, but are not limited to, a) X-Ray Powder Diffraction; b) thermal analyses; c) infrared spectroscopy; d) NMR Spectroscopy; and e) Moisture Sorption/Desorption Analyses.

Examples of Pharmaceutical Compositions, Formulations and Dosage Forms

The present invention provides very significant benefits and advantages for designing safe, stable and effective rusalatide acetate formulations, pharmaceutical compositions and dosage forms.

As used throughout this description, it is to be understood that the term "rusalatide acetate composition, formulation or dosage form" as used herein is intended to broadly include any safe and effective rusalatide acetate composition, formulation or dosage form that includes 23 amino acid monomer ("Monomer"; herein identified as SEQ ID NO: 1), dimer ("Dimer") of two 23 amino acid Monomers, or any combination of Monomer and Dimer, wherein any ratio, proportion or percentage of Monomer and Dimer may be present in the composition, formulation or dosage form. The invention also broadly covers stable compositions, formulations or dosage forms that include rusalatide acetate and any pharmaceutically acceptable salts thereof.

According to a preferred embodiment, the present invention contemplates a rusalatide acetate composition, formulation or dosage form that includes Monomer, Dimer, or any combination of Monomer and Dimer, wherein any ratio, proportion or percentage of Monomer and Dimer may be present in the composition, formulation or dosage form, further wherein the stability of the (i) rusalatide acetate or (ii) the rusalatide acetate composition, formulation or dosage form that includes Monomer, Dimer or any combination of Monomer and Dimer, or (iii) both (i) and (ii), is enhanced according to the methods and systems of the present invention.

According to another preferred embodiment, the present invention contemplates pharmaceutical compositions comprising Monomer, wherein the stability of the Monomer is enhanced according to the methods and systems of the present invention.

According to another preferred embodiment, the present invention contemplates pharmaceutical compositions comprising Dimer, wherein the stability of the Dimer is enhanced according to the methods and systems of the present invention.

According to still other preferred embodiments, the present invention contemplates pharmaceutical compositions comprising a certain percentage of Monomer and a certain percentage of Dimer, wherein the stability of both the Monomer and the Dimer is enhanced according to the methods and systems of the present invention.

The present invention also contemplates, by way of non-limiting example, a dynamic storage suspension wherein the percent or proportion of Monomer, and the percent or proportion of Dimer, can interchange.

The present invention also contemplates, by way of non-limiting example, that in a particular rusalatide acetate composition, formulation or dosage form (i) the percent or proportion of Monomer, (ii) the percent or proportion of Dimer, or (iii) any combination thereof can change in a dynamic manner prior to administration to a subject. For example, within a solution or other aqueous formulation, and prior to administration to a subject, the present invention contemplates that some percentage or proportion of Monomer can dimerize to form some percentage or proportion of Dimer, and thus (i) the percent or proportion of Monomer, (ii) the percent or proportion of Dimer, or (iii) any combination thereof, present within the solution or other aqueous formulation can therefore change in a dynamic manner. This is a non-limiting example and does not limit the scope of the present invention in any way.

The present invention also contemplates, by way of non-limiting example, that (i) the percent or proportion of Monomer, (ii) the percent or proportion of Dimer, or (iii) any combination thereof can change in a dynamic manner after administration to a subject. In a non-limiting example, after administration of a rusalatide acetate dosage form or formulation to a subject, the present invention contemplates that the percent or proportion of Monomer, and the percent or proportion of Dimer, or any combination thereof, in the dosage form or formulation can change in a dynamic manner in vivo, after administration to the subject.

Moreover, by way of non-limiting example, after administration of a stable or stabilized rusalatide acetate composition, formulation or dosage form to a subject in vivo, the present invention contemplates that the composition, formulation or dosage form is effective in delivering a therapeutically effective amount of rusalatide acetate in vivo, such that the rusalatide acetate (comprising Monomer, Dimer, or any combination thereof, in any ratio or percentage amounts or proportions of the Monomer and Dimer, and wherein the ratio or percentage amounts or proportions can change in a dynamic manner) binds and stimulates NPAR in the subject, in vivo, in an effective manner. This is a non-limiting example and does not limit the scope of the present invention in any way.

Moreover, the present invention contemplates that a stabilized rusalatide acetate composition, formulation or dosage form, after preparation, storage and administration to a subject, can undergo spontaneous dimerization in vivo, and this spontaneous dimerization in vivo does not limit the therapeutic activity of the rusalatide acetate composition, formulation or dosage form. It is also contemplated that any suitable technique(s) can be used for analysis of the pharmacokinetics of rusalatide acetate (including, but not limited to, analysis of absorption, bioavailability, distribution, metabolism, excretion, etc.) after in vivo administration of a stabilized rusalatide acetate dosage form, formulation or pharmaceutical composition. Dose-response studies can be performed in a controlled manner and enough data generated to perform statistical analyses. It is further contemplated that such data and information gathered from such pharmacokinetic studies can be utilized to make adjustments or modifications to processes for manufacturing of formulations, or rusalatide acetate pharmaceutical product development, and steps taken as needed or required to further enhance and optimize the stability of a rusalatide acetate dosage form, formulation or pharmaceutical composition.

It is to be understood that, throughout this detailed description herein, a stabilized rusalatide acetate composition, formulation or dosage form is intended to include, but is not limited to, rusalatide acetate that is manufactured by peptide synthesis (examples of peptide synthesis are described herein). It is also contemplated that such a stabilized rusalatide acetate dosage form, formulation or pharmaceutical composition, comprising synthetic rusalatide acetate (manufactured by peptide synthesis), after preparation, storage and administration to a subject, can undergo spontaneous dimerization in vivo, and this spontaneous dimerization in vivo does not limit rusalatide acetate's therapeutic activity.

The present invention also contemplates that, upon administration of a stabilized rusalatide acetate dosage form or formulation to a subject in vivo for a clinical use or application, the stability of the rusalatide acetate dosage form or formulation, and the extent of dimerization (if any) of the Monomer to the Dimer, can be further characterized and evaluated based on data and information gathered after the rusalatide acetate dosage form or formulation has been exposed to the in vivo conditions and processes within the subject, including in vivo processes for metabolism. The stability of a rusalatide acetate dosage form or formulation, and the extent of dimerization (if any) of the Monomer to the Dimer, can be further characterized and evaluated based on clearance studies. Such data and information, which may include aggregated data and information from multiple subjects, can be used to further enhance and optimize the stability and other aspects of rusalatide acetate dosage forms or formulations. The present invention also contemplates that the pharmacokinetic profile of a stabilized rusalatide acetate dosage form or formulation can be characterized by well-known ADME characterization methods (wherein it is understood that ADME refers to "absorption, distribution, metabolism, and excretion").

Moreover, the present invention also contemplates that studies can be performed to evaluate and characterize how long it takes for Monomer to dimerize in circulation. Such data and information can also be used in the development of rusalatide acetate compositions, formulations or dosage forms, and for optimizing the stability of such formulations, compositions or dosage forms.

The present invention also contemplates preparation of stabilized rusalatide acetate dosage forms and formulations in such a manner, according to the present invention, that after administration to a subject, the stabilized rusalatide acetate dosage forms and formulations release rusalatide acetate in the subject in vivo in an amount sufficient to mediate and produce one or more desired therapeutic effects in the subject.

Moreover, as described herein, rusalatide acetate is believed to activate cells by binding to a high-affinity cell-surface thrombin receptor known as the non-proteolytically-activated thrombin receptor ("NPAR"). Compounds which stimulate NPAR are said to be thrombin receptor agonists. rusalatide acetate is one example of an NPAR agonist. The present invention contemplates that one can safely and effectively administer a therapeutically effective amount of a rusalatide acetate composition, formulation or dosage form to a subject, wherein the rusalatide acetate composition, formulation or dosage form includes Monomer, Dimer or any combination of Monomer and Dimer, and wherein a desired therapeutic effect in the subject is mediated at least by rusalatide acetate's effects as an NPAR agonist.

The present invention also contemplates the preparation of stabilized dosage forms or formulations that comprise one or more active metabolites, fragments (e.g. peptide fragments), or derivatives of rusalatide acetate, including such stabilized dosage forms or formulations for one or more clinical applications and uses for producing a desired therapeutic effect in a subject.

The methods, processes and systems of the present invention can also be reliably and accurately used to manufacture and produce any type of safe and effective rusalatide acetate composition, formulation or dosage form that includes Monomer, Dimer, or any combination of Monomer and Dimer. It is also possible to accurately and reliably deliver precise and reproducible dosages of the composition, formulation or dosage form, even after storage for prolonged periods of time.

Representative examples of rusalatide acetate compositions, formulations or dosage forms which can be used in accordance with the present invention include, but are not limited to, the following:

Oral delivery (e.g., tablets, capsules, pills)
Aerosolized sprays
Injectable liquid
Lyophilized powder
Microspheres containing rusalatide acetate
A single use liquid dosage form
A single use gel dosage form
Cream
Gel
Ointment
Encapsulations
Liposomes
Microparticles The present invention also contemplates the use of pellet drug delivery technology for controlled release of rusalatide acetate. It is also contemplated that the pellets can be injected, and such an injectable form of delivery could be very useful for many clinical applications including, for example, the treatment of bone fractures.

Ointments may be prepared, for example, using an oleaginous base, e.g., containing fixed oils or hydrocarbons, such as white petrolatum or mineral oil, or an absorbent base, e.g., consisting of an absorbent anhydrous substance or substances, for example anhydrous lanolin. Following formation of the base, the active ingredients are added in the desired concentration.

It is preferred that creams generally comprise an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases may be preferably stabilized by use of an emulsifying agent, for example, a surface active agent, such as sodium lauryl sulfate; hydrophilic colloids, such as acacia colloidal clays, beegum, and the like. Upon formation of the emulsion, the active ingredients are added in the desired concentration.

It is preferred that gels are comprised of a base selected from an oleaginous base, water, or an emulsion-suspension base. To the base is preferably added a gelling agent which forms a matrix in the base, increasing its viscosity to a semisolid consistency. Examples of gelling agents are hydroxypropyl cellulose, acrylic acid polymers, and the like. It is preferred that the active ingredients are added to the formulation at the desired concentration at a point preceding addition of the gelling agent.

In preferred embodiments, all of the rusalatide acetate formulations, pharmaceutical compositions and dosage forms as described herein are manufactured and produced in accordance with all cGMP (Current Good Manufacturing Practice) and GMP (Good Manufacturing Practice) requirements, for instance, as required at any given time by a regulatory agency. The term "Good Manufacturing Practice" or "GMP", as used herein, is intended to refer to a quality assurance system that is used for making sure that the rusalatide acetate products, formulations, pharmaceutical compositions and dosage forms of the present invention, when manufactured for clinical use, are consistently produced, validated, reviewed, documented and controlled according to quality standards. The formulations, pharmaceutical compositions and dosage forms of the present invention can be prepared to meet all GMP and cGMP regulatory requirements so that the formulations, pharmaceutical compositions and dosage forms are suitable for administration to humans.

As used herein, the term "clinical-grade" is intended to refer to a rusalatide acetate pharmaceutical composition, formulation or dosage form, for example as described herein in accordance with the present invention, that has been prepared and manufactured for clinical use and formally and officially determined by at least one regulatory agency or other approved authority anywhere in the world to be safe and effective for clinical use in humans.

As further described herein, the term "stabilized" is intended to include, but is not limited to, a rusalatide acetate pharmaceutical composition, formulation or dosage form in which the rusalatide acetate has been deemed stable, for example, after analysis of the rusalatide acetate by one or more stability tests.

In a preferred embodiment, the invention contemplates a stabilized, clinical-grade rusalatide acetate composition, formulation or dosage form that includes Monomer, Dimer or any combination of Monomer and Dimer in a safe and therapeutically amount.

Throughout this description, it is contemplated that rusalatide acetate compositions, formulations and dosage forms can include for example any possible ratio, proportion or percentage of 23 amino acid monomer ("Monomer") and dimer ("Dimer") of two 23 amino acid Monomers, including but not limited to 100% Monomer, 100% Dimer, or any other possible ratio, proportion or percentage of the Monomer and Dimer.

In another preferred embodiment, the present invention contemplates a stable or stabilized, clinical-grade rusalatide acetate composition, formulation or dosage form, which includes Monomer, Dimer, or some combination of Monomer and Dimer present in a safe and therapeutically effective amount in the composition, formulation or dosage form, further wherein the stable or stabilized, clinical-grade rusalatide acetate composition, formulation or dosage form is essentially free of any contaminant, impurity or degradation product.

In yet another embodiment, the present invention contemplates a stable or stabilized, clinical-grade rusalatide acetate composition, formulation or dosage form comprising synthetically produced rusalatide acetate.

As used herein, the term "synthetically produced" is intended to refer to rusalatide acetate that is prepared or manufactured by peptide synthesis. In certain embodiments, for example, rusalatide acetate can be synthesized by a solid phase peptide synthesis (for example, but not limited to, BOC or FMOC) method, or in other embodiments by solution phase synthesis. The present invention also contemplates that rusalatide acetate can be synthesized by other suitable techniques including, e.g., combinations of the other methods of peptide synthesis described herein.

In another preferred embodiment, the present invention contemplates a stabilized, clinical-grade rusalatide acetate composition, formulation or dosage form that includes synthetically produced rusalatide acetate in a safe and therapeutically effective amount, further wherein the stabilized, clinical-grade composition, formulation or dosage form is essentially free of any contaminant, impurity or degradation product.

In yet another embodiment, Monomer (i.e., Monomer peptide) can be prepared by recombinant methods, i.e. prepared as a recombinantly produced peptide. The systems and methods of the present invention, including methods and systems for optimizing the stability of rusalatide acetate, as described throughout this description of the present invention, can then be utilized to stabilize the recombinantly produced Monomer peptide.

Representative Example: "Composition "W"

In one preferred embodiment, the present invention contemplates a rusalatide acetate composition ("composition W") comprising:
 (a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), wherein the polypeptide is synthesized and purified according to Good Manufacturing Practice (GMP) requirements, further wherein the composition is essentially free of reactive oxygen species, endotoxins, organic solvents, degradation impurities, and redox-active transition metal impurities,
 and
 (b) at least one pharmaceutically acceptable excipient, wherein the composition is prepared under aseptic conditions, stored with a hygroscopic agent, further wherein the composition is stable, protected from light, and further wherein the composition is packaged and sealed after exposure to a non-reactive, anhydrous purging agent,
 further wherein stability of the composition is determined based at least on a combination of forced degradation analysis, analysis of water content in the composition, counterion quantification analysis, and bioburden testing of the composition.

In yet another embodiment, the present invention contemplates "composition W" as described herein, wherein the polypeptide is lyophilized.

In yet another embodiment, the present invention contemplates "composition W", as described herein, wherein the purging agent is nitrogen.

In yet another embodiment, the present invention contemplates "composition W", as described herein, further wherein the composition is formulated for sterile administration.

In yet another embodiment, the present invention contemplates "composition W", as described herein, wherein the purging agent is argon.

In yet another embodiment, the present invention contemplates "composition W", as described herein, comprising an antioxidant.

Representative Example: "Composition "X"

In yet another preferred embodiment, the present invention contemplates a rusalatide acetate composition ("composition X") comprising:
 (a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), wherein the polypeptide is synthesized and purified according to Good Manufacturing Practice (GMP) requirements, further wherein the composition is essentially free of reactive oxygen species, endotoxins, organic solvents, degradation impurities, and redox-active transition metal impurities,
 (b) a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp- Ser-Gly-Gly-Pro-Phe-Val (SEQ ID NO:1), wherein the polypeptides are covalently linked by a disulfide bond, and (c) an aqueous carrier, further wherein the composition is prepared under aseptic conditions.

further wherein stability of the composition is determined based at least on a combination of forced degradation analysis, counterion quantification analysis, and bioburden testing of the composition.

In yet another embodiment, the present invention contemplates "composition X" as described above, wherein the composition is at least 90 percent free of reactive oxygen species, endotoxins, organic solvents, degradation impurities, and redox-active transition metal impurities.

In yet another embodiment, the present invention contemplates "composition X" as described above, wherein the composition is formulated for sterile administration.

In yet another embodiment, the present invention contemplates "composition X" as described above, wherein the composition is formulated as a single use liquid dosage form.

In yet another embodiment, the present invention contemplates "composition X" as described above, comprising an antioxidant.

Representative Example: "Composition "Y"

In yet another preferred embodiment, the present invention contemplates a rusalatide acetate composition ("composition Y") comprising:

(a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), wherein the polypeptide is synthesized and purified according to Good Manufacturing Practice (GMP) requirements, further wherein the composition is essentially free of reactive oxygen species, endotoxins, organic solvents, degradation impurities, and redox-active transition metal impurities, (b) a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond, and (c) at least one pharmaceutically acceptable excipient, wherein the composition is stable, protected from light, and prepared under aseptic conditions, further wherein stability of the composition is determined based at least on a combination of forced degradation analysis, analysis of water content in the composition, counterion quantification analysis, and bioburden testing of the composition.

In yet another embodiment, the present invention contemplates "composition Y" as described above, wherein the composition is at least 90 percent free of reactive oxygen species, endotoxins, organic solvents, degradation impurities, and redox-active transition metal impurities.

In yet another embodiment, the present invention contemplates "composition Y" as described above, wherein the composition is formulated for topical administration.

In yet another embodiment, the present invention contemplates "composition Y" as described above, wherein the composition is formulated for sterile administration.

In yet another embodiment, the present invention contemplates "composition Y" as described above, wherein the composition is formulated for sterile, injectable delivery.

As used herein, the term "sterile" for example in the context of "sterile, injectable delivery" is intended to refer to delivery that is performed under conditions that are essentially clean, or preferably totally clean. This includes conditions that are essentially free from contaminants, microorganisms, germs, pollutants, and any other undesired substances, or preferably totally free from contaminants, microorganisms, germs, pollutants, and any other undesired substances.

In yet another embodiment, the present invention contemplates "composition Y" as described above, comprising an antioxidant.

In yet another embodiment, the present invention contemplates "composition Y" as described above, wherein the composition is formulated as a single use liquid dosage form.

Figure 3:
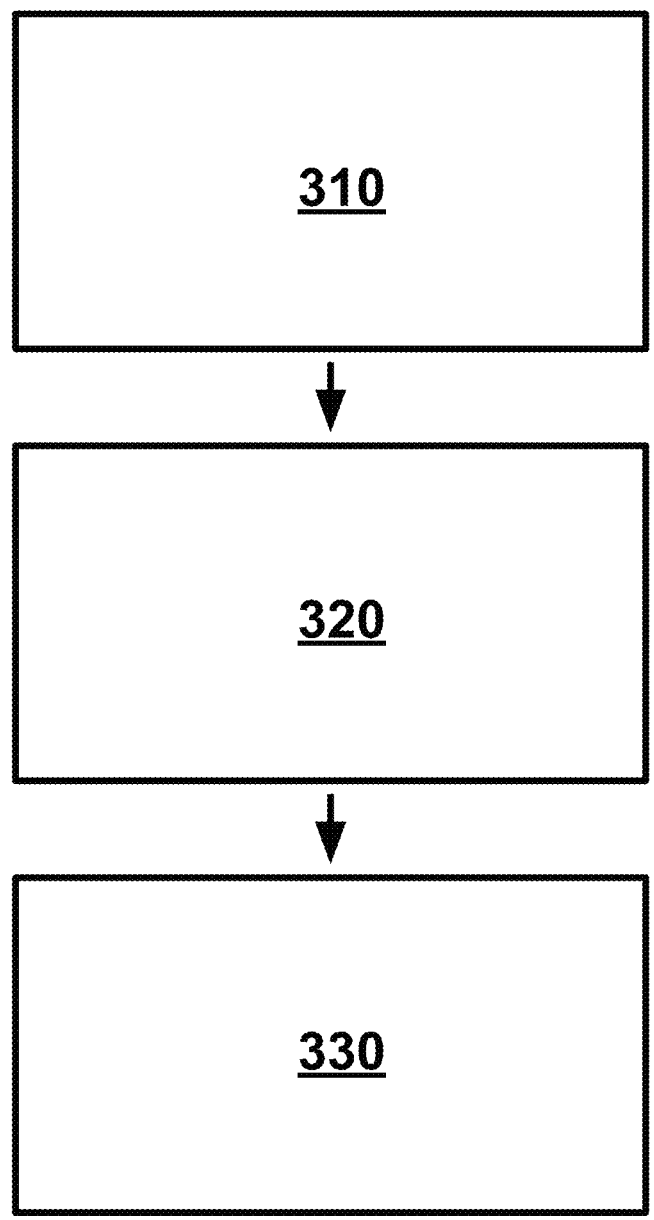
FIG. 3 depicts a schematic diagram of steps involved in a representative method of enhancing the stability of a 23 amino acid polypeptide comprising SEQ ID NO: 1.

In yet another embodiment, as depicted schematically in FIG. 3, the present invention contemplates a method of enhancing the stability of a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1).

Referring to FIG. 3, the method first comprises step 310, which involves simultaneously gathering information about the effects of multiple parameters (for example, atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities) on the stability of the polypeptide.

Referring again to FIG. 3, the method then involves step 320, which involves performing an analysis of the information about the effects of the multiple parameters (e.g., atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities) on the stability of the polypeptide.

Referring yet again to FIG. 3, the method then involves step 330, which involves performing at least one stability optimization procedure based on the analysis such that the stability of the polypeptide is enhanced.

Figure 4:
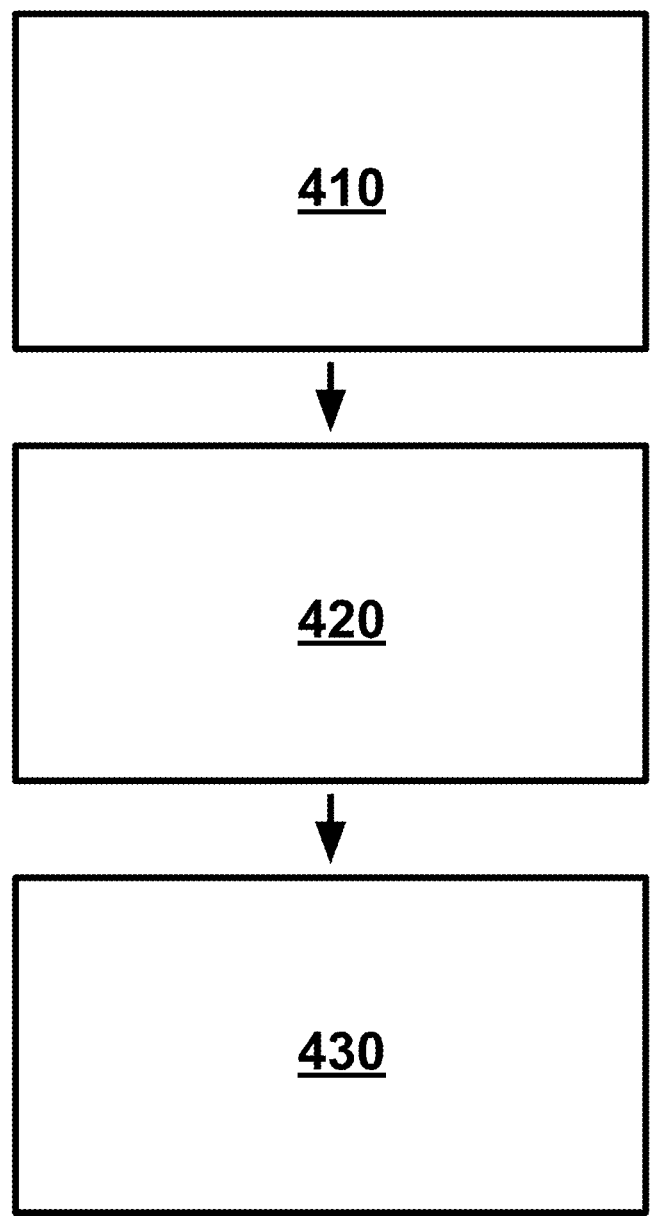
FIG. 4 depicts a schematic diagram of steps involved in a representative method of enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond.

In yet another embodiment, as depicted schematically in FIG. 4, the present invention contemplates a method of enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond.

Referring to FIG. 4, the method first comprises step 410, which involves simultaneously gathering information about the effects of multiple parameters (for example, atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities) on the stability of the peptide dimer.

Referring again to FIG. 4, the method then involves step 420, which involves performing an analysis of the information about the effects of the multiple parameters (e.g., atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities) on the stability of the peptide dimer.

Referring yet again to FIG. 4, the method then involves step 430, which involves performing at least one stability optimization procedure based on the analysis such that the stability of the peptide dimer is enhanced.

Figure 5:
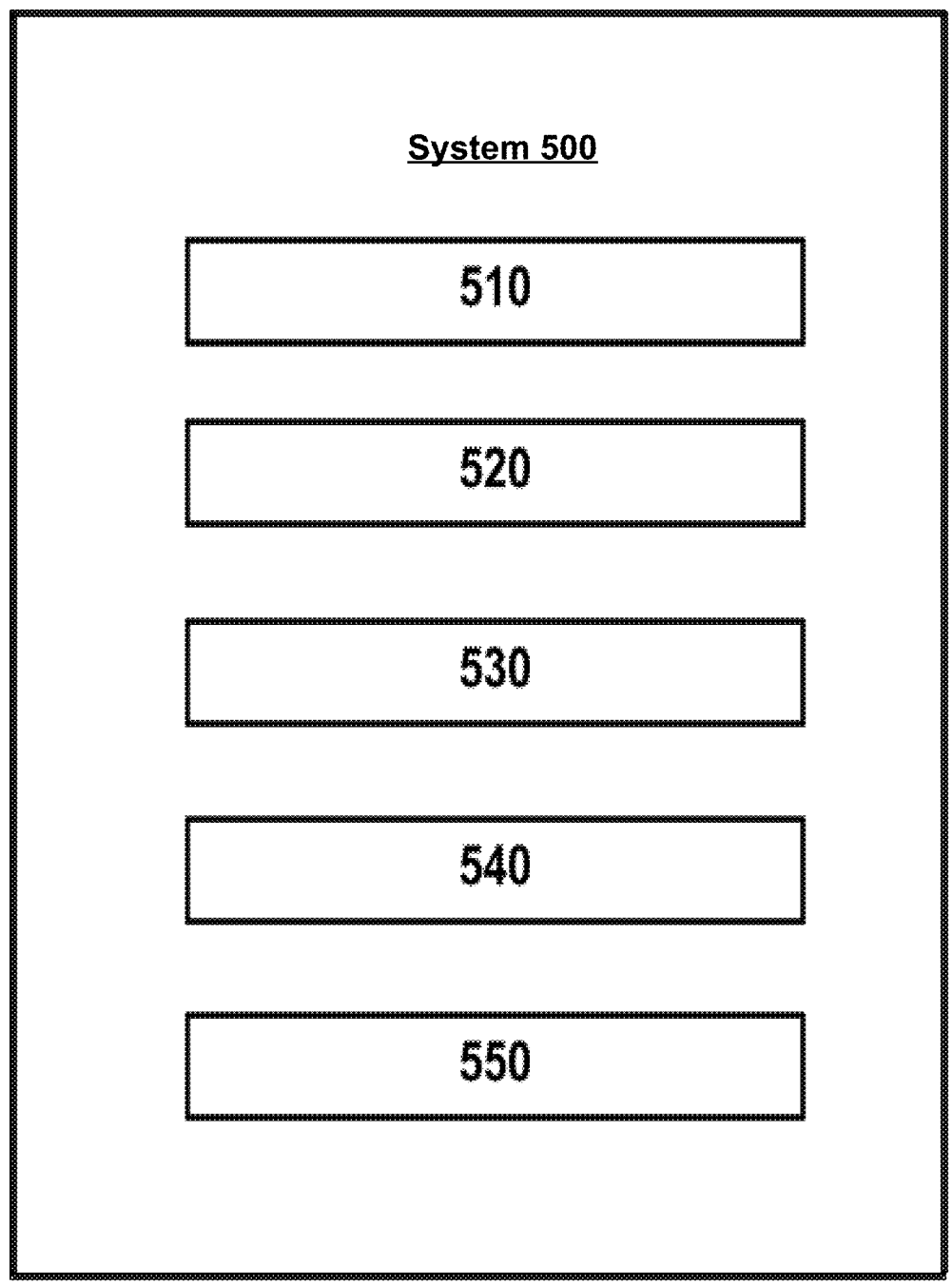
FIG. 5 is a schematic diagram depicting a representative system for enhancing the stability of a 23 amino acid polypeptide comprising SEQ ID NO: 1.

According to yet another preferred embodiment, as depicted schematically in FIG. 5, the present invention provides a system 500 for enhancing the stability of a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1).

Referring to FIG. 5, the system 500 comprises components 510 for simultaneously gathering information about the effects of multiple parameters (e.g., atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities) on the stability of the polypeptide.

The system 500 also comprises components 520 for performing an analysis of the information about the effects of the multiple parameters (e.g., atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities) on the stability of the polypeptide.

Referring again to FIG. 5, the system 500 also comprises components 530 for performing at least one stability optimization procedure based on the analysis such that the stability of the polypeptide is enhanced.

The system 500 further comprises at least one processor 540 and at least one memory storage device 550 for storing the information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide.

Figure 6:
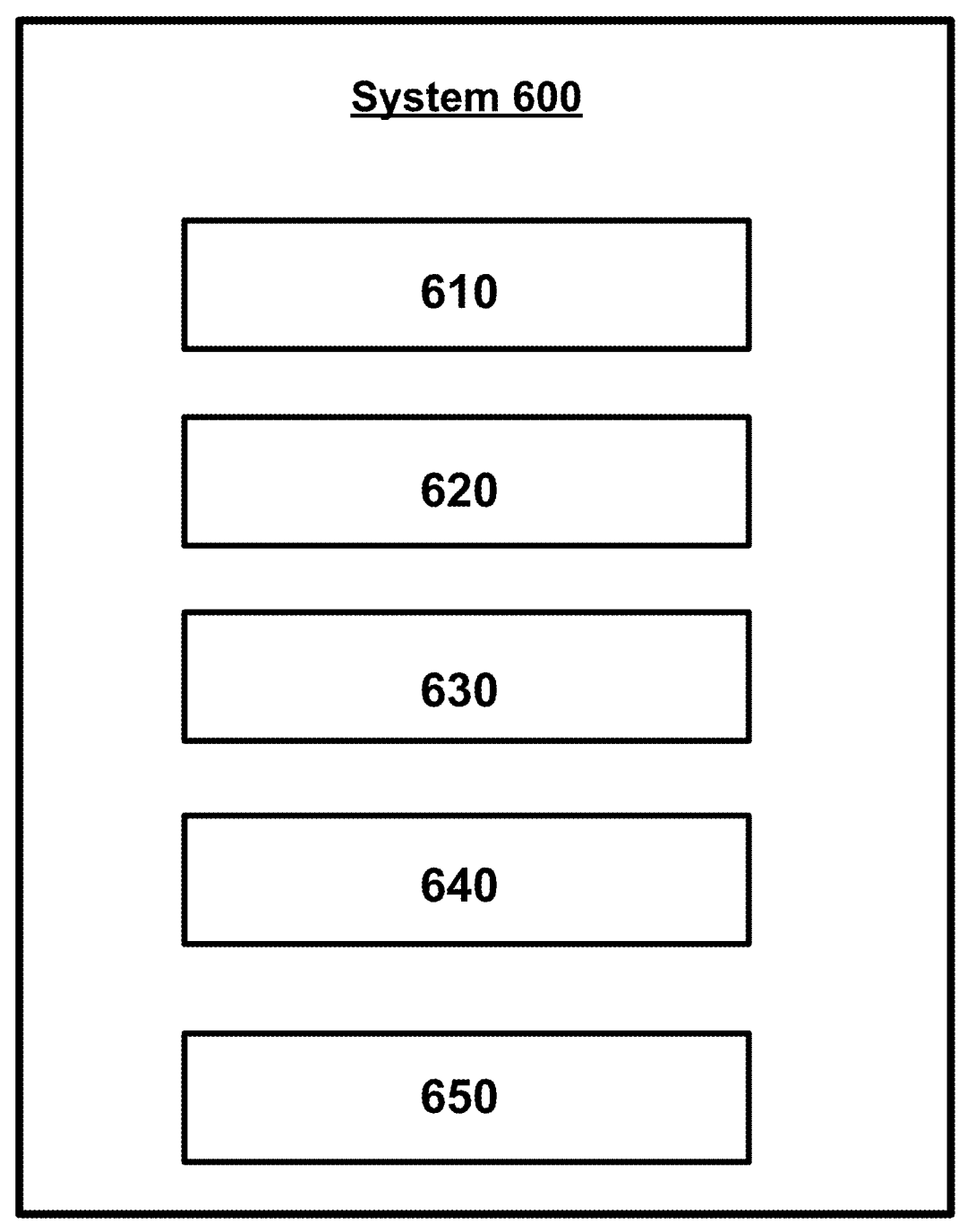

According to yet another preferred embodiment, as depicted schematically in FIG. 6, the present invention provides a system 600 for enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond.

Referring to FIG. 6, the system 600 comprises components 610 for simultaneously gathering information about the effects of multiple parameters (e.g., atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities) on the stability of the peptide dimer.

The system 600 also comprises components 620 for performing an analysis of the information about the effects of the multiple parameters (e.g., atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities) on the stability of the peptide dimer.

Referring again to FIG. 6, the system 600 also comprises components 630 for performing at least one stability optimization procedure based on the analysis such that the stability of the peptide dimer is enhanced.

The system 600 further comprises at least one processor 640 and at least one memory storage device 650 for storing the information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer.

In certain embodiments, the rusalatide acetate formulations and dosage forms of the present invention can be administered by any suitable route, locally or systemically, including, for example, but not limited to, by parenteral administration. Parenteral administration can include, for example, intramuscular, intravenous, subcutaneous, or intraperitoneal injection.

The rusalatide acetate formulations, pharmaceutical compositions and dosage forms of the present invention can also be administered, for example, by topical administration. Topical administration for treating wounds can include, for example, creams, gels, ointments or aerosols. In a preferred embodiment, a final dosage form for topical administration is a liquid, ointment, cream or gel, preferably with at least a one-year shelf life. In one preferred embodiment, it is preferred that the Dimer substantially persists in its dimer form while in a liquid medium at room temperature.

Respiratory administration can include, for example, inhalation or intranasal drops. For certain indications such as stimulating bone growth, cartilage repair, cardiac repair and the treatment of restenosis, it may be advantageous to inject or implant a rusalatide acetate composition, formulation or dosage form directly to the treatment site, wherein the rusalatide acetate composition, formulation or dosage form includes Monomer, Dimer or any combination of Monomer and Dimer.

The rusalatide acetate formulations, pharmaceutical compositions or dosage forms can also be advantageously administered as a sustained release formulation.

A rusalatide acetate composition, formulation or dosage form can also be administered using at least one pharmaceutically acceptable carrier. The exact components (including any excipients) of a formulation, pharmaceutical composition or dosage form may vary according to the route of administration selected. Suitable pharmaceutical carriers may contain inert ingredients which do not interact with or impact the rusalatide acetate, and which do not affect stability of (i) rusalatide acetate or (ii) a rusalatide acetate composition, formulation or dosage form that includes Monomer, Dimer or any combination of Monomer and Dimer, or (iii) both (i) and (ii). The preferred carriers that can be used are biocompatible, non-toxic, non-inflammatory, non-immunogenic and do not cause undesired reactions at the administration site. Examples of pharmaceutically acceptable carriers include, but are not limited to, saline, aerosols, commercially available inert gels, or liquids supplemented with albumin, methyl cellulose or a collagen matrix. Safe and effective pharmaceutical formulation techniques can be utilized such as those described, for example, in Remington's Pharmaceutical Sciences, Mack Publishing Company, Easton, Pennsylvania, USA.

In yet another alternative embodiment, a rusalatide acetate formulation, pharmaceutical composition or dosage form can be partially or completely enclosed in a supporting physical structure such as a mesh, wire matrix, stainless steel cage, threaded interbody fusion cage and the like before administering to the site in need of bone growth.

In certain instances, injectable delivery formulations may preferably be administered intravenously or directly at the site in need of treatment. The injectable carrier may, for example, be a viscous solution or a gel.

In preferred embodiments, a rusalatide acetate formulation, pharmaceutical composition or dosage form can be administered via sterile administration. The term "sterile administration", as used herein, refers to administration or delivery of a rusalatide acetate formulation, pharmaceutical composition or dosage form in such a manner whereby the administration or delivery is performed in an aseptic, clean, uncontaminated, and uninfected manner, such that the administration or delivery to a subject does not introduce contaminants, bacteria or other microorganisms, or anything else that might be harmful into the subject. The terms "aseptic" and "aseptic conditions", as used herein, are broadly intended to refer to conditions that are free or essentially free from contamination caused by any type of harmful viruses, bacteria, or other harmful microorganisms.

Moreover, the delivery mechanism (for example, a device for injection) is also maintained in an aseptic, clean, uncontaminated, and uninfected condition, and the procedures involved (including the handling procedures by personnel) are also performed in an aseptic, clean, uncontaminated, and uninfected setting, for the safety and benefit of the subject.

In other preferred embodiments, delivery formulations may include, for example, physiological saline, bacteriostatic saline (for example, saline containing about 0.9% mg/mL benzyl alcohol), phosphate-buffered saline, Hank's solution, Ringer's-lactate, or a liquid supplemented with albumin, methyl cellulose, or hyaluronic acid. Injectable matrices may include, for example, one or more polymers of poly(ethylene oxide) and copolymers of ethylene and propylene oxide.

Injectable matrices can be injected, for example, directly to the site in need of bone growth and can conveniently be used to fill voids and fuse bones without the need for invasive surgery.

It is understood that the description provided herein provides non-limiting examples, and the examples are for illustration purposes only. The examples do not limit the scope of the invention in any way. It is understood that any other type of rusalatide acetate pharmaceutical composition, formulation or dosage form can also be used in accordance with the present invention.

Representative Methods of Treatment

According to a preferred embodiment, the present invention contemplates methods useful for treating a subject in need of treatment with a rusalatide acetate composition, formulation or dosage form, wherein said rusalatide acetate composition, formulation or dosage form includes Monomer, Dimer or any combination of Monomer and Dimer, further wherein the stability of the formulation, composition or dosage form is enhanced according to the methods and systems of the present invention.

According to another preferred embodiment, the present invention contemplates methods useful for treating a subject in need of treatment with Monomer, comprising treatment with an effective amount of Monomer, wherein the stability of the Monomer is enhanced according to the methods and systems of the present invention.

According to another preferred embodiment, the present invention contemplates methods useful for treating a subject in need of treatment with Dimer, comprising treatment with an effective amount of Dimer, wherein the stability of the Dimer is enhanced according to the methods and systems of the present invention. In preferred embodiments, Dimer is administered for treatment because of its therapeutic activity.

An "effective amount" refers to an amount, concentration, dose or quantity of a rusalatide acetate formulation, pharmaceutical composition or dosage form that results in an improved clinical outcome of a condition in a subject being treated with the formulation, pharmaceutical composition or dosage form, compared with the absence of treatment. The amount, concentration, dose or quantity of the formulation, pharmaceutical composition or dosage form administered will depend on the degree, severity, and type of the disease or condition, the amount of therapy desired, and the release characteristics of the formulation, pharmaceutical composition or dosage form. It will also typically depend on the subject's health, size, weight, age, sex and tolerance to drugs. Typically, the formulation, pharmaceutical composition or dosage form is administered for a sufficient period of time to achieve the desired therapeutic effect.

According to another preferred embodiment, the present invention also contemplates the use of a rusalatide acetate composition, formulation or dosage form that includes Monomer, Dimer, or any combination of Monomer and Dimer, for treating one or more conditions in a human or non-human subject.

The rusalatide acetate compositions, formulations and dosage forms of the present invention can be used, for example, for promoting tissue repair or for the treatment of wounds. Such wounds include, but are not limited to, diabetic foot ulcers (DFU), including DFU of the plantar and heel surfaces, as well as all other types of ulcers, sores and lesions including but not limited to venous ulcers, dermal ulcers, pressure sores, mouth sores, and ulcerative lesions.

The stabilized rusalatide acetate pharmaceutical compositions, formulations and dosage forms of the present invention can also be used, for example, in the treatment or prevention of diseases or conditions in which angiogenesis, revascularization or cell proliferation would be beneficial.

The stabilized rusalatide acetate pharmaceutical compositions, formulations and dosage forms of the present invention can also be used, for example, to prevent restenosis in patients after angioplasty and for promoting the regeneration of blood vessels in cardiac tissue.

The stabilized rusalatide acetate pharmaceutical compositions, formulations and dosage forms of the present invention can also be used to provide myocardial protection, for example, after acute ischemia reperfusion injury, and provide other cardiovascular protective effects.

The stabilized rusalatide acetate pharmaceutical compositions, formulations and dosage forms of the present invention can also be used to attenuate the effects of chronic hypoxia, and provide protective effects during hypoxia or ischemia.

According to yet another preferred embodiment, the stabilized rusalatide acetate pharmaceutical compositions, formulations and dosage forms of the present invention can also be used for promoting healing and treatment of any type of wound including but not limited to acute wounds such as burns, dermal wounds, and surgical wounds.

According to yet another preferred embodiment, the stabilized rusalatide acetate pharmaceutical compositions, formulations and dosage forms of the present invention can also be used in the treatment of bone fractures; stimulating bone growth to promote healing of simple fractures, non-union fractures, voids and gaps in bone and bone grafts, stimulation of cartilage growth, and treatment of cartilage damage.

It is also contemplated that the stabilized rusalatide acetate pharmaceutical compositions, formulations and dosage forms of the present invention have many other uses and applications including, but not limited to, treatment or management of chronic and acute inflammatory and degenerative conditions caused by injury, disease or aging.

The present invention also contemplates that the stable or stabilized rusalatide acetate compositions, formulations or dosage forms of the present invention may include Monomer, Dimer, or any combination of Monomer and Dimer which may be present at any time in any ratio, proportion or percentage, in any desired or suitable amount or concentration, and for any purpose as needed or desired, including but not limited to preparation of stock concentrations or for dosing or administration to a subject for one or more types of treatments.

Diseases and conditions that are treatable with rusalatide acetate formulations, pharmaceutical compositions and dosage forms are often accompanied by symptoms and infirmities such as pain and infection. In certain instances, it may be advantageous to co-administer one or more additional pharmacologically active agents with a rusalatide acetate formulation, pharmaceutical composition or dosage form to address such issues. For example, managing pain and inflammation may involve co-administration with one or more analgesic agents, one or more anti-inflammatory agents, or any combination thereof. Managing infection may involve co-administration with one or more antimicrobial, antibiotic or disinfectant agents, or any combination thereof.

Enhanced Purity of Rusalatide Acetate

Strict regulations by the Food and Drug Administration (FDA) require a high degree of purity of biologically active agents when used as pharmaceuticals. It therefore is important to obtain active rusalatide acetate, and which maintains or essentially maintains its purity over extended time periods, if used to treat humans.

As used throughout this description herein, the term "purity" is intended to broadly refer to the degree or extent to which an active agent (for example, rusalatide acetate) is free or essentially free from contamination or contaminants of any kind, and free or essentially free from degradation impurities and any other impurity of any kind.

As used herein, the term "essentially free" is preferably intended to refer to a state or condition that is nearly free, approximately free or substantially free of unwanted components. For example, "essentially free" can preferably refer to a state or condition that is greater than 90 percent free, more preferably greater than 95 percent free, even more preferably greater than 98 percent free, and still more preferably greater than 99 percent free of unwanted components. For example, a composition that is "essentially free" of contaminants (including contaminants that can be detected by standard analytical and detection techniques) is intended to refer to a composition that is, for example, preferably greater than 90 percent free from said contaminants, more preferably greater than 95 percent free from said contaminants, even more preferably greater than 98 percent free from said contaminants, and still more preferably greater than 99 percent free from said contaminants.

In another example, rusalatide acetate that has a purity of at least 90% is intended to refer to rusalatide acetate that is at least 90% free or essentially free from contamination or contaminants, and at least 90% free or essentially free from degradation impurities and any other impurity of any kind.

In yet another example, rusalatide acetate that has a purity of at least 95% is intended to refer to rusalatide acetate that is at least 95% free or essentially free from contamination or contaminants, and at least 95% free or essentially free from degradation impurities and any other impurity of any kind.

In yet another example, rusalatide acetate that has a purity of at least 98% is intended to refer to rusalatide acetate that is at least 98% free or essentially free from contamination or contaminants, and at least 98% free or essentially free from degradation impurities and any other impurity of any kind.

In yet another example, rusalatide acetate that has a purity of at least 99% is intended to refer to rusalatide acetate that is at least 99% free or essentially free from contamination or contaminants, and at least 99% free or essentially free from degradation impurities and any other impurity of any kind.

In certain embodiments, the present invention contemplates that the percent of pure 23 amino acid Monomer, for example in a batch or sample, may be accurately and reliably determined and measured.

The present invention also contemplates that in other embodiments, the percent of pure Dimer of two 23 amino acid Monomers may be accurately and reliably determined and measured.

In one embodiment, the purity of (i) rusalatide acetate or the purity of (ii) a rusalatide acetate composition, formulation or dosage form that includes Monomer, Dimer or any combination of Monomer and Dimer can be measured and analyzed by HPLC or other suitable analytical technique.

In one example, in order to determine Net Peptide Content relative to counterions or water, a Net Peptide Content measurement can be performed, which can be obtained through AAA (amino acid analysis) or Carbon Hydrogen Nitrogen (CHN) analysis.

The present invention also contemplates 23 amino acid monomer ("Monomer") that is at least ninety (90) percent pure (in other words, Monomer that has a purity of at least 90 percent). Monomer having this percent purity can be used in the rusalatide acetate compositions, formulations and dosage forms of the present invention.

The present invention also contemplates Monomer that is at least ninety-five (95) percent pure (in other words, Monomer that has a purity of at least 95 percent). Monomer having this percent purity can be used in the rusalatide acetate compositions, formulations and dosage forms of the present invention.

The present invention also contemplates Monomer that is at least ninety-six (96) percent pure (in other words, Monomer that has a purity of at least 96 percent). Monomer having this percent purity can be used in the rusalatide acetate compositions, formulations and dosage forms of the present invention.

The present invention also contemplates Monomer that is at least ninety-eight (98) percent pure (in other words, Monomer that has a purity of at least 98 percent). Monomer having this percent purity can be used in the rusalatide acetate compositions, formulations and dosage forms of the present invention.

The present invention also contemplates Monomer that is at least ninety-nine (99) percent pure (in other words, Monomer that has a purity of at least 99 percent). Monomer having this percent purity can be used in the rusalatide acetate compositions, formulations and dosage forms of the present invention.

In yet other embodiments, the present invention also contemplates that the purity of a rusalatide acetate composition, formulation or dosage form can be accurately and reliably determined and measured, for example by analyzing for the presence of any contaminants in the rusalatide acetate composition, formulation or dosage form.

According to preferred embodiments of the present invention, a rusalatide acetate composition, formulation or dosage form is produced with a purity of at least 90% (wherein the composition, formulation or dosage form is at least 90% free of any contaminants).

According to another embodiment, a rusalatide acetate composition, formulation or dosage form is produced with a purity of at least 95% (wherein the composition, formulation or dosage form is at least 95% free of any contaminants).

According to another embodiment, a rusalatide acetate composition, formulation or dosage form is produced with a purity of at least 96% (wherein the composition, formulation or dosage form is at least 96% free of any contaminants).

According to another embodiment, a rusalatide acetate composition, formulation or dosage form is produced with a purity of at least 98% (wherein the composition, formulation or dosage form is at least 98% free of any contaminants).

According to another embodiment, a rusalatide acetate composition, formulation or dosage form is produced with a purity of at least 99% (wherein the composition, formulation or dosage form is at least 99% free of any contaminants).

According to a preferred embodiment, the present invention contemplates a method of enhancing the stability of a Monomer, comprising: gathering physical, non-abstract information about at least one parameter, wherein the parameter affects stability of the Monomer; performing a physical, non-abstract analysis of the information about the at least one parameter; and performing at least one physical, non-abstract stability optimization procedure based on the analysis such that the stability of the Monomer is enhanced.

According to another preferred embodiment, the present invention contemplates a method of enhancing the stability of a Monomer, comprising: gathering physical, non-abstract information about at least two parameters, wherein each parameter affects stability of the Monomer; performing a physical, non-abstract analysis of the information about the at least two parameters; and performing at least one physical, non-abstract stability optimization procedure based on the analysis such that the stability of the Monomer is enhanced.

According to another preferred embodiment, the present invention contemplates a method of enhancing the stability of a Monomer, comprising: gathering physical, non-abstract information about at least three parameters, wherein each parameter affects stability of the Monomer; performing a physical, non-abstract analysis of the information about the at least three parameters; and performing at least one physical, non-abstract stability optimization procedure based on the analysis such that the stability of the Monomer is enhanced.

According to a preferred embodiment, the present invention contemplates a method of enhancing the stability of a Dimer, comprising: gathering physical, non-abstract information about at least one parameter, wherein the parameter affects stability of the Dimer; performing a physical, non-abstract analysis of the information about the at least one parameter; and performing at least one physical, non-abstract stability optimization procedure based on the analysis such that the stability of the Dimer is enhanced.

According to another preferred embodiment, the present invention contemplates a method of enhancing the stability of a Dimer, comprising: gathering physical, non-abstract information about at least two parameters, wherein each parameter affects stability of the Dimer; performing a physical, non-abstract analysis of the information about the at least two parameters; and performing at least one physical, non-abstract stability optimization procedure based on the analysis such that the stability of the Dimer is enhanced.

According to another preferred embodiment, the present invention contemplates a method of enhancing the stability of a Dimer, comprising: gathering physical, non-abstract information about at least three parameters, wherein each parameter affects stability of the Dimer; performing a physical, non-abstract analysis of the information about the at least three parameters; and performing at least one physical, non-abstract stability optimization procedure based on the analysis such that the stability of the Dimer is enhanced.

According to a preferred embodiment, a method of enhancing the stability of a rusalatide acetate formulation, pharmaceutical composition or dosage form comprises:
    optimizing a first parameter during a process of preparing the rusalatide acetate formulation;
    optimizing a second parameter during the process of preparing the rusalatide acetate formulation; and
    optimizing a third parameter during the process of preparing the rusalatide acetate formulation,
    wherein optimizing the first, second and third parameters results in enhanced stability of the rusalatide acetate formulation.

According to a preferred embodiment, the present invention also contemplates a system for enhancing the stability of (i) rusalatide acetate or (ii) a rusalatide acetate composition, formulation or dosage form that includes Monomer, Dimer or any combination of Monomer and Dimer, or (iii) both (i) and (ii). The system preferably includes: at least one physical, non-abstract computer-based instrumentation system, wherein the at least one physical, non-abstract computer-based instrumentation system is operable for collecting and processing physical, non-abstract information that is gathered with regard to at least one parameter, wherein the parameter affects stability of the rusalatide acetate formulation, pharmaceutical composition or dosage form; further wherein the at least one physical, non-abstract computer-based instrumentation system is operable for performing a physical, non-abstract analysis of the information about the at least one parameter; and further wherein the at least one physical, non-abstract computer-based instrumentation system is operable for performing at least one physical, non-abstract stability optimization procedure based on the analysis such that the stability of the rusalatide acetate formulation, pharmaceutical composition or dosage form is enhanced.

According to a preferred embodiment, the present invention also contemplates a system for enhancing the stability of a Monomer, the system comprising: at least one physical, non-abstract computer-based instrumentation system, wherein the at least one physical, non-abstract computer-based instrumentation system is operable for collecting and processing physical, non-abstract information that is gathered with regard to at least one parameter, wherein the parameter affects stability of the Monomer; further wherein the at least one physical, non-abstract computer-based instrumentation system is operable for performing a physical, non-abstract analysis of the information about the at least one parameter; and further wherein the at least one physical, non-abstract computer-based instrumentation system is operable for performing at least one physical, non-abstract stability optimization procedure based on the analysis such that the stability of the Monomer is enhanced.

According to a preferred embodiment, the present invention also contemplates a system for enhancing the stability of a Monomer, comprising: at least one physical, non-abstract computer-based instrumentation system, wherein the at least one physical, non-abstract computer-based instrumentation system is operable for collecting and processing physical, non-abstract information that is gathered with regard to at least two parameters, wherein the parameters affect stability of the Monomer; further wherein the at least one physical, non-abstract computer-based instrumentation system is operable for performing a physical, non-abstract analysis of the information about the at least two parameters; and further wherein the at least one physical, non-abstract computer-based instrumentation system is operable for performing at least one physical, non-abstract stability optimization procedure based on the analysis such that the stability of the Monomer is enhanced.

According to a preferred embodiment, the present invention also contemplates a system for enhancing the stability of a Monomer, comprising: at least one physical, non-abstract computer-based instrumentation system, wherein the at least one physical, non-abstract computer-based instrumentation system is operable for collecting and processing physical, non-abstract information that is gathered with regard to at least three parameters, wherein the parameters affect stability of the Monomer; further wherein the at least one physical, non-abstract computer-based instrumentation system is operable for performing a physical, non-abstract analysis of the information about the at least three parameters; and further wherein the at least one physical, non-abstract computer-based instrumentation system is operable for performing at least one physical, non-abstract stability optimization procedure based on the analysis such that the stability of the Monomer is enhanced.

According to a preferred embodiment, the present invention also contemplates a system for enhancing the stability of a Dimer, comprising: at least one physical, non-abstract computer-based instrumentation system, wherein the at least one physical, non-abstract computer-based instrumentation system is operable for collecting and processing physical, non-abstract information that is gathered with regard to at least one parameter, wherein the parameter affects stability of the Dimer; further wherein the at least one physical, non-abstract computer-based instrumentation system is operable for performing a physical, non-abstract analysis of the information about the at least one parameter; and further wherein the at least one physical, non-abstract computer-based instrumentation system is operable for performing at least one physical, non-abstract stability optimization procedure based on the analysis such that the stability of the Dimer is enhanced.

According to a preferred embodiment, the present invention also contemplates a system for enhancing the stability of a Dimer, comprising: at least one physical, non-abstract computer-based instrumentation system, wherein the at least one physical, non-abstract computer-based instrumentation system is operable for collecting and processing physical, non-abstract information that is gathered with regard to at least two parameters, wherein the parameters affect stability of the Dimer; further wherein the at least one physical, non-abstract computer-based instrumentation system is operable for performing a physical, non-abstract analysis of the information about the at least two parameters; and further wherein the at least one physical, non-abstract computer-based instrumentation system is operable for performing at least one physical, non-abstract stability optimization procedure based on the analysis such that the stability of the Dimer is enhanced.

According to a preferred embodiment, the present invention also contemplates a system for enhancing the stability of a Dimer, comprising: at least one physical, non-abstract computer-based instrumentation system, wherein the at least one physical, non-abstract computer-based instrumentation system is operable for collecting and processing physical, non-abstract information that is gathered with regard to at least three parameters, wherein the parameters affect stability of the Dimer; further wherein the at least one physical, non-abstract computer-based instrumentation system is operable for performing a physical, non-abstract analysis of the information about the at least three parameters; and further wherein the at least one physical, non-abstract computer-based instrumentation system is operable for performing at least one physical, non-abstract stability optimization procedure based on the analysis such that the stability of the Dimer is enhanced.

According to another preferred embodiment, the present invention also contemplates a system for enhancing the stability of a rusalatide acetate composition, formulation or dosage form, wherein said rusalatide acetate composition, formulation or dosage form includes Monomer, Dimer or any combination of Monomer and Dimer, the system comprising at least one physical, non-abstract computer-based instrumentation system, wherein the operations of the at least one physical, non-abstract computer-based instrumentation system includes the use of any suitable artificial intelligence (A.I.) or machine-learning technology, or other suitable type of advanced analytical technology, and further wherein the at least one physical, non-abstract computer-based instrumentation system comprises at least one physical component of computer hardware architecture or microarchitecture which is essential and required to specifically perform the methods and operations of the present invention as described herein. The operations of the at least one physical, non-abstract computer-based instrumentation system include, but are not limited to:

(i) collecting and processing physical, non-abstract information that is gathered with regard to at least one parameter, wherein the parameter affects stability of the rusalatide acetate formulation, pharmaceutical composition or dosage form;

(ii) performing a physical, non-abstract analysis of the information about the at least one parameter; and (iii) performing at least one physical, non-abstract stability optimization procedure based on the analysis such that the stability of the rusalatide acetate formulation, pharmaceutical composition or dosage form is enhanced.

According to another preferred embodiment, the present invention also contemplates a system for enhancing the stability of a Monomer, comprising at least one physical, non-abstract computer-based instrumentation system, wherein the operations of the at least one physical, non-abstract computer-based instrumentation system includes operation of any suitable artificial intelligence (A.I.) or machine-learning technology, or other suitable type of advanced analytical technology, and further wherein the at least one physical, non-abstract computer-based instrumentation system comprises at least one physical component of computer hardware architecture or microarchitecture which is essential and required to specifically perform the methods and operations of the present invention as described herein. The operations of the at least one physical, non-abstract computer-based instrumentation system include, but are not limited to:
  (i) collecting and processing physical, non-abstract information that is gathered with regard to at least one parameter, wherein the parameter affects stability of the Monomer;
  (ii) performing a physical, non-abstract analysis of the information about the at least one parameter; and
  (iii) performing at least one physical, non-abstract stability optimization procedure based on the analysis such that the stability of the Monomer is enhanced.

According to another preferred embodiment, the present invention also contemplates a system for enhancing the stability of a Monomer, as herein described, wherein the operations of the at least one physical, non-abstract computer-based instrumentation system include, but are not limited to:
  (i) collecting and processing physical, non-abstract information that is gathered with regard to at least three parameters, wherein each of the three parameters affects stability of the Monomer;
  (ii) performing a physical, non-abstract analysis of the information about the at least three parameters; and
  (iii) performing at least one physical, non-abstract stability optimization procedure based on the analysis such that the stability of the Monomer is enhanced.

According to another preferred embodiment, the present invention also contemplates a system for enhancing the stability of a Dimer, comprising at least one physical, non-abstract computer-based instrumentation system, wherein the operations of the at least one physical, non-abstract computer-based instrumentation system includes operation of any suitable artificial intelligence (A.I.) or machine-learning technology, and further wherein the at least one physical, non-abstract computer-based instrumentation system comprises at least one physical component of computer hardware architecture or microarchitecture which is essential and required to specifically perform the methods and operations of the present invention as described herein. The operations of the at least one physical, non-abstract computer-based instrumentation system include, but are not limited to:
  (i) collecting and processing physical, non-abstract information that is gathered with regard to at least one parameter, wherein the parameter affects stability of the Dimer;
  (ii) performing a physical, non-abstract analysis of the information about the at least one parameter; and
  (iii) performing at least one physical, non-abstract stability optimization procedure based on the analysis such that the stability of the Dimer is enhanced.

According to another preferred embodiment, the present invention also contemplates a system for enhancing the stability of a Dimer, as herein described, wherein the operations of the at least one physical, non-abstract computer-based instrumentation system include, but are not limited to:
  (i) collecting and processing physical, non-abstract information that is gathered with regard to at least three parameters, wherein each of the three parameters affects stability of the Dimer;
  (ii) performing a physical, non-abstract analysis of the information about the at least three parameters; and
  (iii) performing at least one physical, non-abstract stability optimization procedure based on the analysis such that the stability of the Dimer is enhanced.

The systems of the present invention, including for example the systems for enhancing the stability of a rusalatide acetate formulation, pharmaceutical composition or dosage form, can preferably be implemented using any type of computer hardware system, network system, or other platform. According to a preferred embodiment, a physical, non-abstract computer-based instrumentation system includes all the necessary components of a computer system that are required to "run" or execute a source program, and that allow someone to use the computer. By way of non-limiting example, the hardware components include, but are not limited to, a power supply, motherboard, hard disk, graphics card, random access memory (RAM), and other hardware components. Additional hardware components can include, for instance, a keyboard, mouse, speakers, etc. It is contemplated that the methods and systems of the present invention can therefore be implemented by operation of any type of computer system that includes computer components including but not limited to a processor, memory storage devices for the processor, connected display devices and input devices. Furthermore, the methods of the present invention can also be implemented by operation of computer components in a heterogeneous distributed computing environment, including for example one or more remote file servers, computer servers, and/or memory storage devices. Each of these distributed computing components is accessible by the processor via a communication network, which may include, but is not limited to, the Internet.

REPRESENTATIVE EXAMPLES

The following, non-limiting examples illustrate certain aspects of the invention. These examples shall not be construed as limiting the scope of the invention in any way.

Example 1

For enhancing and optimizing the stability of a rusalatide acetate pharmaceutical composition, numerous attributes and parameters of rusalatide acetate were analyzed and evaluated. Data was obtained using the PEP-FOLD server (University of Paris, Diderot, Paris, France). Using a physical, non-abstract computer system comprising computer hardware necessary to operate the computer, analysis was performed using the PEP-FOLD server to generate a predicted structure of the Monomer, based on the Monomer sequence (AGYKPDEGKRGDACEGDSGGPFV). In this example, the PEP-FOLD server was accessed using the physical, non-abstract computer system to perform de novo modelling of three-dimensional (3D) conformations of the Monomer (AGYKPDEGKRGDACEGDSGGPFV).

Using the PEP-FOLD server, the following actions or steps were performed to yield predicted three-dimensional (3D) conformations of the Monomer sequence:
PEP-FOLD3 (1/5): Local prediction
PEP-FOLD3 (2/5): 3D generation
10% . . . 20% . . . 30% . . . 40% . . . 50% . . . 60% . . . 70% . . . 80% . . . 90% . . . 100% (timepoint 1 analysis performed)
10% . . . 20% . . . 30% . . . 40% . . . 50% . . . 60% . . . 70% . . . 80% . . . 90% . . . 100% (timepoint 2 analysis performed)

10% ... 20% ... 30% ... 40% ... 50% ... 60% ... 70% ... 80% ... 90% ... 100% (timepoint 3 analysis performed)

PEP-FOLD3 (3/5): PostTreatment

10% ... 20% ... 30% ... 40% ... 50% ... 60% ... 70% ... 80% ... 90% ... 100% (timepoint 4 analysis performed)

PEP-FOLD3 (4/5): clustering

DBClusters (1/4): checking options

DBClusters (2/4): preparing results

PEP-FOLD3 (5/5): compiling results

PEP-FOLD (6/6): formatting results

Based on the analysis and the data that was obtained, the PEP-FOLD server yielded predicted 3D conformations of the Monomer, including a "ball and stick" model which schematically depicts a predicted 3D conformation of the Monomer. The predicted 3D conformation of the Monomer can be rotated or viewed in different orientations. Examples of these different orientations are schematically depicted in FIG. 1A, FIG. 1B, and FIG. 1C.

FIG. 1A depicts the Monomer in one 3D orientation (see reference numeral 100 with the arrow that points to the Monomer in this 3D orientation).

FIG. 1B depicts the Monomer in another 3D orientation (see reference numeral 110 with the arrow that points to the Monomer in this 3D orientation).

FIG. 1C depicts the Monomer in yet another 3D orientation (see reference numeral 120 with the arrow that points to the Monomer in this 3D orientation).

Similar analysis of predicted 3D conformations are performed for the Dimer.

The PEP-FOLD server provided very valuable information about the rusalatide acetate peptide, including predicted 3D conformations, and analysis of this information is very useful during preformulation and formulation stages. The information gathered in this manner is also used by machine learning systems, artificial intelligence tools, and using other analytical techniques, computer systems and other tools for enhancing and optimizing the stability of rusalatide acetate in rusalatide acetate pharmaceutical compositions, formulations and dosage forms.

Example 2

In this study, several attributes and parameters of rusalatide acetate were analyzed and data was obtained based on the Monomer sequence (AGYKPDEGKRG-DACEGDSGGPFV). The ThermoFisher Peptide Analyzing system was used by an experienced scientist to perform the analysis, and in this study the scientist also used a physical, non-abstract computer system, with processor, memory storage and all essential hardware components and other components of the computer system. Based on the Monomer sequence, the results from this study (as described below) using the ThermoFisher Peptide Analyzing system provided very valuable information about rusalatide acetate, including valuable data about multiple parameters and rusalatide acetate peptide physicochemical properties, including a charge-pH map and data about isoelectric point (pI), hydrophobicity, mass, molecular weight (MW; in grams/mole) including MW average and MW monoisotopic values. In addition, the study provided very valuable information about peptide synthesis and purification, including relative speed of delivery, and also peptide compatibility with SRM/MRM quantitative mass spectrometry workflows.

Figure 2:
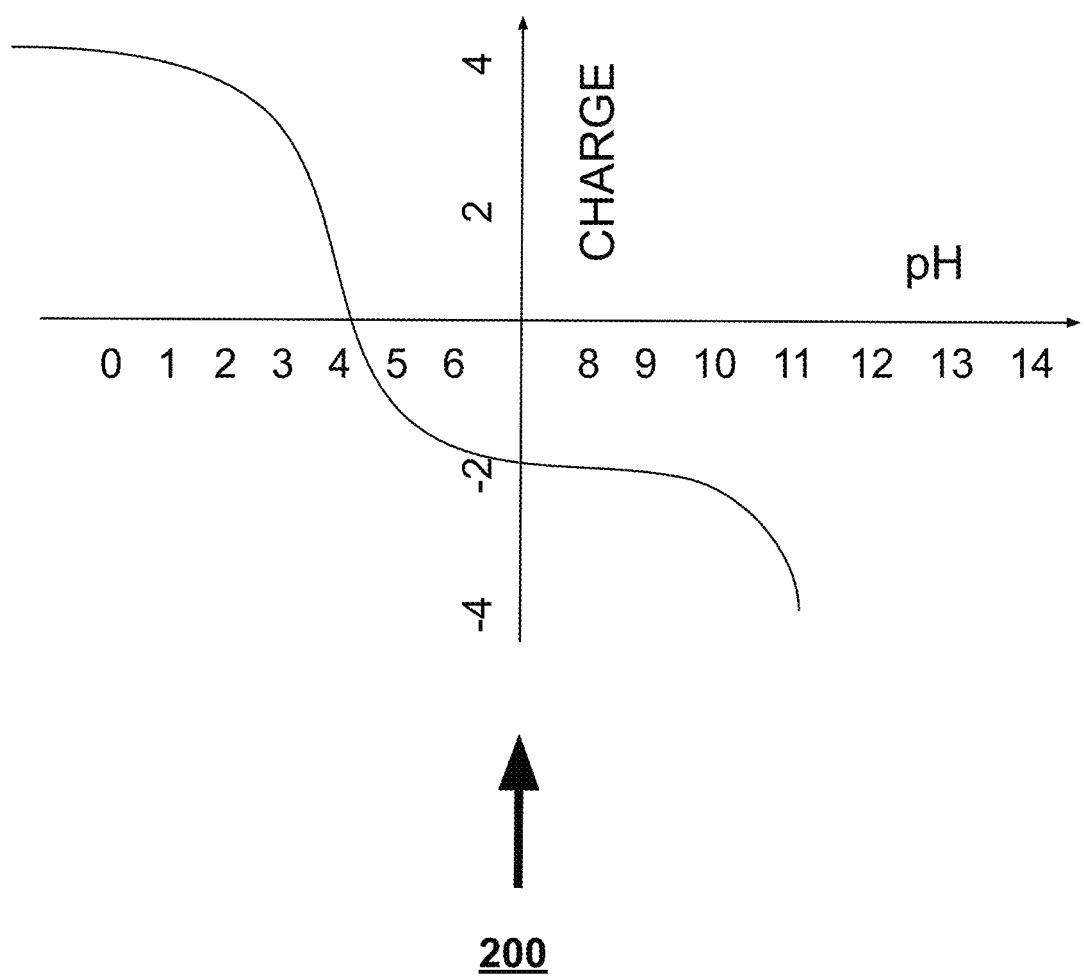
FIG. 2 depicts a schematic representation of a charge-pH map of the Monomer based on the Monomer sequence.

Referring to FIG. 2, a schematic representation of a charge-pH map of the Monomer is shown based on the Monomer sequence (SEQ ID NO: 1) (see reference numeral 200 in FIG. 2 with the arrow that points to the charge-pH map). The information from this charge-pH map was used to further analyze and characterize rusalatide acetate. The data from this study is also used during preformulation and formulation stages to enhance and optimize the stability of rusalatide acetate in rusalatide acetate pharmaceutical compositions, formulations and dosage forms.

In addition, this study (utilizing the ThermoFisher analysis) also provided the following additional data, based on analysis of the Monomer sequence (SEQ ID NO: 1) shown below:

(SEQ ID NO: 1)
A-G-Y-K-P-D-E-G-K-R-G-D-A-C-E-G-D-S-G-G-P-F-V

Sequence length: 23

Hydrophobicity: 19.93

GRAVY: −1.06

MW (molecular weight) average: 2312.4733 grams/mol

MW (molecular weight) monoisotopic: 2311.0177

Isoelectric point (pI): 4.2

The "GRAVY" (or the "grand average of hydropathy") value or measurement was used in this study to help analyze, measure and evaluate the hydrophobicity of the rusalatide acetate peptide. This data is very useful for preformulation and formulation stages for preparing rusalatide acetate pharmaceutical compositions, formulations or dosage forms. Additional data (not shown in this example) is obtained by other reliable analytical methods for analysis of the Dimer. All of the data gathered from this study, including the ThermoFisher analysis, is useful for developing methods and protocols to enhance the stability of (i) rusalatide acetate and (ii) rusalatide acetate compositions, formulations and dosage forms that include Monomer, Dimer or any combination of Monomer and Dimer. This study, including the ThermoFisher analysis, provided physical, non-abstract information about several parameters and rusalatide acetate peptide physicochemical properties, and analysis of these parameters and physicochemical properties is very useful during preformulation and formulation stages, and for enhancing the stability of rusalatide acetate pharmaceutical compositions, formulations and dosage forms.

The data from this study, based on the ThermoFisher analysis, was also very useful from a product development standpoint, and the data enable manufacturing and product development teams to better characterize rusalatide acetate and develop efficient and cost-effective methods for the synthesis, purification and delivery of the rusalatide acetate peptide.

In addition, information obtained from this study (based on the ThermoFisher analysis) also indicated that the hydrophobicity of the rusalatide acetate peptide makes it compatible with selected reaction monitoring (SRM) and multiple reaction monitoring (MRM) experiments for sensitive, specific, rapid and reproducible quantification of rusalatide acetate in batch samples at any stage, including any preformulation or formulation stage.

Example 3

An analytical study was performed to gather information to further characterize and predict the stability of rusalatide acetate. In this study, an analysis of rusalatide acetate was performed, in which numerous attributes, parameters and physicochemical properties of rusalatide acetate were analyzed. The data and information obtained is useful during preformulation and formulation stages for designing stable rusalatide acetate formulations and pharmaceutical compositions, and the information is also useful for predicting the half-life of rusalatide acetate peptide in an intestine-like environment. For this analytical study, the HLP webserver (Bioinformatics Centre, Institute of Microbial Technology, Chandigarh, India), using a computer based system with accompanying processor, hardware components and other components of the computer based system, was used to gather information about rusalatide acetate based on the Monomer sequence:

AGYKPDEGKRGDACEGDSGGPFV

The analysis was performed using the HLP webserver and a Support Vector Machine (SVM) based model. The HLP webserver and the SVM based model generated valuable information and data about numerous attributes and physicochemical properties of rusalatide acetate.

Based on the data obtained in this study, using the HLP webserver and the SVM based model, the analysis indicated that the hydrophobicity of the Monomer sequence was 10.339 kilojoules per mole (kJ/mol). Hydrophobicity was measured as the standard free energy change for the transfer of a given amino acid residue from a hydrophobic solvent into water, in kilojoules per mole (kJ/mol). This hydrophobicity value, which provided useful information about the relative hydrophobicity of rusalatide acetate, is useful during preformulation and formulation stages for designing stable rusalatide acetate formulations and pharmaceutical compositions with desired solubility characteristics.

In addition, based on the Monomer sequence and the HLP webserver analysis, the residue volume was calculated to be 2651.300 (in particular, based on the sum of the residue volume values, measured in cubic angstroms, wherein the residue volume value for each residue is determined based on the volume of space enclosed by the van der Waals surface for that given residue).

Additional data was also gathered to further characterize the Monomer sequence. In this study, further analysis of the data indicated that the Monomer sequence had a surface accessibility value of 47.235 (the surface accessibility was calculated based on the sum of the average accessibility surface area values for the individual amino acids).

Based on the Monomer sequence, the HLP webserver analysis also indicated a flexibility value of 10.960 (this is a measure of amino acid side chain flexibility, determined based on the sum of amino acid scale values). Using the HLP webserver analysis, the Monomer sequence was also determined to have the following physicochemical characteristics:

a charge of negative two (−2.000) (based on the overall charge, calculated based on the Monomer sequence);
a polarity value of 381.320 (based on the sum of polarity values for the individual amino acids in the sequence);
a relative mutability value of 1601.000 (based on the sum of the relative mutability values for the individual amino acids in the sequence);
a free energy of solution (in water, kcal/mole) of 10.701;
an optical rotation value of negative 6.557 (−6.557) (based on the average of the optical rotation values for the individual amino acids in the sequence);
an entropy of formation value of 4444.240 (based on the sum of entropy of formation values, given the Monomer amino acid sequence);
a heat capacity value of 832.180 (based on the sum of heat capacity values, given the Monomer amino acid sequence); and
a relative stability value of 2.170 (based on the average of relative stability scale values for individual amino acids, and given the Monomer amino acid sequence).

Additional data was obtained, based on the Monomer sequence, and using the HLP webserver and the SVM based model. Based on the Monomer sequence, the data indicated a pKa value of 49.770, and a pKb value of 219.470. The isoelectric point was calculated to be 5.793.

The analysis also led to a prediction that the half-life (calculated in seconds) of the Monomer is 4.856 seconds, i.e., in an intestine-like environment. The half-life is very valuable information for predicting the stability of the peptide (a greater half-life corresponds to greater stability of the peptide). Based on the data obtained in this study, including the predicted half-life of rusalatide acetate, the analysis indicated a high degree of stability of rusalatide acetate.

Analysis of the data about these attributes, parameters and physicochemical properties provides very useful information which is reliably and effectively used at preformulation and formulation stages for enhancing the stability, and optimizing the stability, of safe and effective compositions, dosage forms and formulations comprising rusalatide acetate. The data generated from this study is used at a "preformulation characterization" stage and also during subsequent stages for developing and manufacturing rusalatide acetate compositions, dosage forms and formulations to enhance and optimize the stability of (i) rusalatide acetate or (ii) a rusalatide acetate composition, formulation or dosage form that includes Monomer, Dimer or any combination of Monomer and Dimer, or (iii) both (i) and (ii).

Example 4

An analytical study was performed to gather information to help further characterize and predict the stability of rusalatide acetate. In this study, an analysis of rusalatide acetate was performed, in which numerous attributes, parameters and physicochemical properties of rusalatide acetate were analyzed. The data and information obtained is useful during preformulation and formulation stages for designing stable rusalatide acetate formulations and pharmaceutical compositions, and the information is also useful for predicting the half-life of rusalatide acetate peptide in an intestine-like environment. For this analytical study, the HLP webserver (Bioinformatics Centre, Institute of Microbial Technology, Chandigarh, India) (a computer based system), with accompanying processor, hardware components and other components of the computer based system, was used to gather information about rusalatide acetate based on the Monomer sequence:

AGYKPDEGKRGDACEGDSGGPFV

The analysis was performed using the HLP webserver and using a WEKA (Waikato Environment for Knowledge Analysis) machine learning based model. The HLP webserver and the WEKA machine learning based model generated valuable information about numerous attributes and physicochemical properties of rusalatide acetate.

The analysis using the HLP webserver and the WEKA based model indicated that the hydrophobicity of the Monomer sequence was 10.339 kilojoules per mole (kJ/mol).

Hydrophobicity was measured as the standard free energy change for the transfer of a given amino acid residue from a hydrophobic solvent into water, in kilojoules per mole (kJ/mol). This hydrophobicity index, which provides useful information about the relative hydrophobicity of rusalatide acetate, is useful during preformulation and formulation stages for designing stable rusalatide acetate formulations and pharmaceutical compositions with desired solubility characteristics.

Based on the Monomer sequence and the HLP webserver analysis, the residue volume was calculated to be 2651.300 (i.e., based on the sum of the residue volume values, measured in cubic angstroms, wherein the residue volume value for each residue was determined based on the volume of space enclosed by the van der Waals surface for that given residue).

Additional data was also gathered to further characterize the Monomer sequence. In this study, further analysis indicated that the Monomer sequence had a surface accessibility value of 47.235 (the surface accessibility was calculated based on the sum of the average accessibility surface area values for the individual amino acids).

Based on the Monomer sequence, the HLP webserver analysis also indicated a flexibility value of 10.960 (this is a measure of amino acid side chain flexibility, determined based on the sum of amino acid scale values). Using the HLP webserver analysis, the Monomer sequence was also determined to have the following physicochemical characteristics:

- a charge of negative two (−2.000) (based on the overall charge, calculated based on the Monomer sequence);
- a polarity value of 381.320 (based on the sum of polarity values for the individual amino acids in the sequence);
- a relative mutability value of 1601.000 (based on the sum of the relative mutability values for the individual amino acids in the sequence);
- a free energy of solution (in water, kcal/mole) of 10.701;
- an optical rotation value of negative 6.557 (−6.557) (based on the average of the optical rotation values for the individual amino acids in the sequence);
- an entropy of formation value of 4444.240 (based on the sum of entropy of formation values, given the Monomer amino acid sequence);
- a heat capacity value of 832.180 (based on the sum of heat capacity values, given the Monomer amino acid sequence); and
- a relative stability value of 2.170 (based on the average of relative stability scale values for individual amino acids, and given the Monomer amino acid sequence).

Additional data was obtained, based on the Monomer sequence, and using the HLP webserver and the WEKA based model. Based on the Monomer sequence, the data indicated a pKa value of 49.770, and a pKb value of 219.470. The isoelectric point was calculated to be 5.793.

Analysis of the data about these attributes, parameters and physicochemical properties provides very useful information which is reliably and effectively used at preformulation and formulation stages for enhancing the stability, and optimizing the stability, of safe and effective rusalatide acetate compositions, formulations and dosage forms, wherein the rusalatide acetate compositions, formulations and dosage forms include Monomer, Dimer or any combination of Monomer and Dimer. The data generated from this study is used at a "preformulation characterization" stage and also during subsequent stages for developing and manufacturing compositions, dosage forms and formulations to enhance and optimize the stability of the rusalatide acetate compositions, formulations and dosage forms.

Example 5

A study is performed to analyze and characterize the potency and stability of various rusalatide acetate compositions. The stability of (i) a topical rusalatide acetate pharmaceutical composition and the stability of (ii) an injectable rusalatide acetate pharmaceutical composition are evaluated, by comparing the use of different combinations of excipients in different pharmaceutical compositions. Stability tests are performed and data is analyzed using a machine learning computer based system, with accompanying processor, hardware components and other computer system components. All of the data is useful in both preformulation and formulation stages, for enhancing and optimizing the stability of a rusalatide acetate pharmaceutical composition.

Example 6

A study is performed to analyze and characterize the potency and stability of different rusalatide acetate compositions, formulations or dosage forms. The stability of (i) a topical rusalatide acetate pharmaceutical composition and the stability of (ii) an injectable rusalatide acetate pharmaceutical composition are evaluated, by comparing the use of different combinations of excipients in different pharmaceutical compositions. Stability tests are performed and data is analyzed using an artificial intelligence based system, with accompanying processor, hardware components and other computer system components. All of the data is useful in both preformulation and formulation stages, for enhancing and optimizing the stability of a rusalatide acetate pharmaceutical composition.

Example 7

I. In the first stage of this study, a computer system, with accompanying servers, hardware components, processor, computer memory, etc, is used to analyze multiple attributes and parameters, and the analysis is used to enhance and optimize the stability of rusalatide acetate. The computer system receives, processes and analyzes a large set of combined data that is generated based on the analysis of these multiple attributes and parameters. This combined data is obtained from numerous sources including (i) the PEP-FOLD server (this study is described in a previous example), (ii) the ThermoFisher analysis (this study is also described in a previous example), (iii) the HLP webserver with accompanying processor, hardware components and other computer system components, utilizing the Support Vector Machine (SVM) based model (this study is also described in a previous example), and (iv) the HLP webserver with accompanying processor, hardware components and other computer system components, utilizing the WEKA (Waikato Environment for Knowledge Analysis) machine learning based model (this study is also described in a previous example). All of the combined data analyzed in this first stage of the study is referred to as "first stage combined data".

II. In the second stage of this study, a series of controlled experiments are performed (i.e., with all proper control groups, for statistical analysis) under sterile conditions to test and evaluate the extent to which atmospheric oxygen is a parameter that affects the stability of rusalatide acetate.

In one set of controlled experiments, a control batch (a control group) of lyophilized, solid rusalatide acetate (3 milligrams total rusalatide acetate) is stored and maintained in an opaque vial under ambient air conditions at negative twenty (−20) degrees Celsius. Opaque vials are used to protect the rusalatide acetate from exposure to light, and to minimize any potential photo-oxidation of the rusalatide acetate. For this control batch, no steps are taken to displace any of the ambient oxygen or other elements present in the ambient environment within the opaque vial.

A separate, test batch of lyophilized, solid rusalatide acetate (3 milligrams total rusalatide acetate) is stored and maintained in a separate opaque test-batch vial at negative twenty (−20) degrees Celsius. With the test-batch vial, nitrogen purging is used and, more specifically, pure nitrogen gas is introduced within the test-batch vial to displace the ambient oxygen present within the ambient environment, i.e., within the space surrounding the rusalatide acetate in the test-batch vial. The pure nitrogen gas that is used is an inert, non-reactive gas and the nitrogen gas effectively displaces the oxygen within the test-batch vial. The nitrogen gas is introduced into the test-batch vial using sterile tubing connected to a nitrogen tank (a nitrogen gas cylinder), to release a gentle stream of nitrogen gas from the outlet end of the sterile tubing, and extra care is taken not to blow or displace any of the lyophilized, solid rusalatide acetate within the vial. After the oxygen is displaced in the test-batch vial, the vial is then re-sealed under the atmosphere of nitrogen gas and under sterile conditions, and stored at negative twenty (−20) degrees Celsius. Thus, with the nitrogen purging within the test-batch vial, steps are taken to minimize the extent to which the rusalatide acetate is exposed to oxygen in the ambient environment in the vial.

Measurements are then taken using analytical instrumentation and (i) the extent of oxidation of rusalatide acetate in the control batch is compared to (ii) the extent of oxidation of rusalatide acetate in the test batch. Measurements are taken at a wide range of time points, including the following time points: 1 hour, 2 hours, 3 hours, 5 hours, 8 hours, 12 hours, 1 day, 2 days, 3 days, 4 days, 5 days, 6 days, 1 week, 2 weeks, 3 weeks, 4 weeks, 5 weeks, 6 weeks, 1 month, 2 months, 3 months, 4 months, 5 months and 6 months (all time points measurements are taken after the nitrogen purging is completed as described above, for instance one hour after the nitrogen purging is completed as described above). The results are used to determine the appropriate conditions to enhance and optimize the stability of rusalatide acetate, and to minimize any undesired oxidation of rusalatide acetate.

Additional series of controlled experiments are also performed in which other control batches of lyophilized, solid rusalatide acetate are stored and maintained in opaque vials under ambient air conditions at negative twenty (−20) degrees Celsius, and compared to corresponding test batches of rusalatide acetate in opaque vials also stored at negative twenty (−20) degrees Celsius (with the test batches, nitrogen purging is used as described above).

In one set of controlled experiments, the control vial and test vial each contain one (1) milligram total of lyophilized, solid rusalatide acetate.

In yet another set of controlled experiments, the control vial and test vial each contain five (5) milligrams total of lyophilized, solid rusalatide acetate.

In yet another set of controlled experiments, the control vial and test vial each contain ten (10) milligrams total of lyophilized, solid rusalatide acetate.

In yet another set of controlled experiments, the control vial and test vial each contain twenty (20) milligrams total of lyophilized, solid rusalatide acetate.

Based on an analysis of the data from the experiments, predictive analytics, machine learning and predictive modeling provide very valuable information about the effects of atmospheric oxygen, including exposure to ambient air, on stability.

III. In the third stage of this study, an experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 6 (all of the "first stage combined data") in combination with the data from the second stage of this study, and the computer system is used for performing computational analysis that utilizes predictive analytics, machine learning and predictive modeling. Based on the simultaneous analysis of all the data, the predictive analytics, machine learning and predictive modeling are used for predicting specific conditions that would be beneficial during pre-formulation and formulation stages for enhancing and optimizing the stability of rusalatide acetate including rusalatide acetate in a pharmaceutical composition. The computer system is used, with accompanying processor, hardware components and other computer system components, and based on the overall combined analysis of data based on all the numerous attributes and parameters, steps are taken during preformulation and formulation stages to enhance and optimize the stability of rusalatide acetate including rusalatide acetate in a pharmaceutical composition.

Example 8

In this study, a series of controlled experiments are performed (i.e., with all proper control groups, for statistical analysis) under sterile conditions to test and evaluate the extent to which ionizing radiation and different reactive oxygen species, including but not limited to superoxide radical, singlet oxygen, hydroxyl radical, and hydrogen peroxide, are parameters that affect the stability of (i) rusalatide acetate or (ii) a rusalatide acetate composition, formulation or dosage form that includes Monomer, Dimer or any combination of Monomer and Dimer, or (iii) both (i) and (ii).

In a control group, an aqueous formulation of rusalatide acetate is prepared (by combining a pure aqueous solvent with one milligram of solid lyophilized rusalatide acetate), and the formulation is stored at about four degrees Celsius (about 4° C.) in a cool, dark place, away from bright light, in an opaque vial. The control group (in the opaque vial) is not exposed to any ionizing radiation.

Several opaque "test vials" are prepared, and each separate opaque test vial contains its own separate aqueous formulation of rusalatide acetate (for each separate test vial, an aqueous formulation is prepared by combining a pure aqueous solvent with one milligram of solid lyophilized rusalatide acetate). Each test vial is an opaque vial, to protect the rusalatide acetate from exposure to light, and each test vial is stored at about four degrees Celsius (about 4° C.) in a cool, dark place, away from bright light.

The first opaque test vial is exposed to six gray (6 Gy) of ionizing radiation at a rate of 500 cGy/minute.

The second opaque test vial is exposed to six and one-half gray (6.5 Gy) of ionizing radiation at a rate of 500 cGy/minute.

The third opaque test vial is exposed to seven gray (7 Gy) of ionizing radiation at a rate of 500 cGy/minute.

The fourth opaque test vial is exposed to seven and one-half gray (7.5 Gy) of ionizing radiation at a rate of 500 cGy/minute.

The fifth opaque test vial is exposed to eight gray (8 Gy) of ionizing radiation at a rate of 500 cGy/minute.

The sixth opaque test vial is exposed to eight and one-half gray (8.5 Gy) of ionizing radiation at a rate of 500 cGy/minute.

The seventh opaque test vial is exposed to nine gray (9 Gy) of ionizing radiation at a rate of 500 cGy/minute.

The eighth opaque test vial is exposed to nine and one-half gray (9.5 Gy) of ionizing radiation at a rate of 500 cGy/minute.

The data is analyzed to determine the effects on stability of rusalatide acetate.

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 7 in combination with all of the data and information obtained from this study (as described herein, in Example 8), and the computer system is used for performing computational analysis that utilizes predictive analytics, machine learning and predictive modeling. The predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of ionizing radiation on stability. Separate controlled studies are also performed to evaluate the effects of different reactive oxygen species, including but not limited to superoxide radical, singlet oxygen, hydroxyl radical, and hydrogen peroxide, on stability.

Example 9

A set of controlled experiments are performed (i.e., with all proper control groups, for statistical analysis) under sterile conditions to test and evaluate the extent to which an antioxidant affects the stability of rusalatide acetate.

For the control group, at "day zero", a topical (gel) formulation of rusalatide acetate is prepared (which includes one milligram of rusalatide acetate), and the formulation is stored at about four degrees Celsius (about 4° C.), in a cool, dark place, away from bright light, in an opaque vial. The opaque vial protects the rusalatide acetate from exposure to light. The control group (in the opaque vial) does not contain any antioxidant (it contains no ascorbic acid).

A series of test vials are also prepared (each in an opaque vial) at "day zero". Each opaque test vial contains its own separate topical (gel) formulation of rusalatide acetate (which includes one milligram of rusalatide acetate), and each separate formulation is stored at about four degrees Celsius (about 4° C.) in a cool, dark place, away from bright light.

In addition to rusalatide acetate, each test vial also contains a certain percentage amount of the antioxidant ascorbic acid.

The first test vial contains about 0.001% by weight of ascorbic acid.

The second test vial contains about 0.01% by weight of ascorbic acid.

The third test vial contains about 0.05% by weight of ascorbic acid.

The fourth test vial contains about 1.0% by weight of ascorbic acid.

The fifth test vial contains about 2.0% by weight of ascorbic acid.

The sixth test vial contains about 3.5% by weight of ascorbic acid.

The seventh test vial contains about 5.0% by weight of ascorbic acid.

The eighth test vial contains about 10.0% by weight of ascorbic acid.

Stability tests are performed on the rusalatide acetate in the control group, and the rusalatide acetate in each of the test groups (test vials), and these stability tests are performed at several time intervals after "day zero", including but not limited to one day, three days, five days, eight days, one week, three weeks, five weeks, six weeks, eight weeks, one month, three months, five months, six months, and eight months after "day zero". The stability tests are used to determine total rusalatide acetate remaining in the control group, and total rusalatide acetate remaining in each test vial, and also any degradation product(s) due to rusalatide acetate degradation.

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 8 in combination with all of the data and information obtained from this study (as described herein, in Example 9), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of the antioxidant ascorbic acid on stability.

Example 10

A series of controlled experiments are performed (i.e., with all proper control groups, for statistical analysis) under sterile conditions to test and evaluate the extent to which moisture content is a parameter that affects stability. Data indicates that rusalatide acetate is hygroscopic, and thus rusalatide acetate tends to absorb moisture from the air.

I. In a first set of controlled experiments, for the control group, at "time zero", an opaque vial containing one milligram of lyophilized solid rusalatide acetate is prepared and stored under refrigeration at about four degrees Celsius (about 4° C.), in a cool, dark place, away from bright light, and no desiccant is included within the opaque vial in the control group.

For the test group, at "time zero", a separate opaque vial containing one milligram of lyophilized solid rusalatide acetate is prepared and the vial of rusalatide acetate is kept in a cool, dark place, away from bright light, stored under refrigeration at about four degrees Celsius (about 4° C.), and steps are also taken to minimize and control the moisture content by including a desiccant within the test group opaque vial. Specifically, a desiccant bag that contains desiccant silica gel (silicone dioxide) is included within the opaque vial of lyophilized solid rusalatide acetate in the test group.

Separate stability tests are performed on (i) the rusalatide acetate in the control group and (ii) the rusalatide acetate in the test group at several time points, including stability tests at three days, five days, one week, two weeks, three weeks, one month, two months, three months, five months, and six months after "time zero" (i.e., after the beginning of the experiments).

II. In a second set of controlled experiments, for the control group, at "time zero", an opaque vial containing three milligrams of lyophilized solid rusalatide acetate is prepared and stored under refrigeration at minus twenty degrees Celsius (−20° C.), in a cool, dark place, away from bright light, and no desiccant is included within the vial in the control group.

For the test group, at "time zero", a separate opaque vial containing three milligrams of lyophilized solid rusalatide acetate is prepared and the vial of rusalatide acetate is kept in a cool, dark place, away from bright light, stored under refrigeration at minus twenty degrees Celsius (−20° C.), and steps are also taken to minimize and control the moisture content by including a desiccant within the test group vial. Specifically, a desiccant bag that contains molecular sieve (synthetic zeolite) is included within the opaque vial of lyophilized solid rusalatide acetate in the test group.

Separate stability tests are performed on (i) the rusalatide acetate in the control group and (ii) the rusalatide acetate in the test group at several time points, including stability tests at three days, five days, one week, two weeks, three weeks, one month, two months, three months, five months, and six months after "time zero" (i.e., after the beginning of the experiments).

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information, which includes all the combined data from Examples 1 through 9, in combination with all of the data and information obtained from this study (as described herein, in Example 10), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of moisture content on stability. Moreover, the selection and use of suitable and appropriate desiccants are predicted to help ensure the integrity and performance of a finished rusalatide acetate pharmaceutical product.

Example 11

A series of controlled experiments are performed (i.e., with all proper control groups, for statistical analysis) under sterile conditions to test and evaluate the extent to which relative humidity (RH) is a parameter that affects the stability of rusalatide acetate.

On "day one", several opaque vials of rusalatide acetate are prepared, each opaque vial containing one milligram of lyophilized solid rusalatide acetate, and each vial stored in its own separate room under refrigeration at four degrees Celsius (4° C.), in a cool, dark place, away from bright light. The several opaque vials of rusalatide acetate are further stored as follows:

the first vial is maintained under conditions with a RH of about 0%;
the second vial is maintained under conditions with a RH of about 10%;
the third vial is maintained under conditions with a RH of about 20%;
the fourth vial is maintained under conditions with a RH of about 30%;
the fifth vial is maintained under conditions with a RH of about 40%;
the sixth vial is maintained under conditions with a RH of about 50%;
the seventh vial is maintained under conditions with a RH of about 60%;
the eighth vial is maintained under conditions with a RH of about 70%;
the ninth vial is maintained under conditions with a RH of about 80%;
the tenth vial is maintained under conditions with a RH of about 90%; and
the eleventh vial is maintained under conditions with a RH of about 100%.

Based on these different RH conditions, stability tests are then performed, and measurements are taken, to measure any degradation of rusalatide acetate, including degradation of any Monomer or Dimer. Measurements (i.e., to analyze for any degradation) are taken at several time points after "day one", including measurements at three days, five days, one week, two weeks, three weeks, one month, two months, three months, five months, and six months after "day one" (i.e., after the beginning of the experiments).

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 10 in combination with all of the data and information obtained from this study (as described herein, in Example 11), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of relative humidity (RH) on stability.

Example 12

A series of controlled experiments are performed (i.e., with all proper control groups, for statistical analysis) under sterile conditions to test and evaluate the extent to which the type of carrier is a parameter that affects stability. In this particular study, glycerol was evaluated as the carrier.

At "time zero", a control vial is prepared (the control vial is an opaque vial that contains one milligram of rusalatide acetate in distilled water, in a total final volume of ten milliliters of distilled water). The control vial is stored under refrigeration at four degrees Celsius (4° C.), in a cool, dark place, away from bright light.

Also, at "time zero", a series of test vials are prepared. Each separate test vial is an opaque vial that contains one milligram of rusalatide acetate in a carrier (in this study, the carrier for each test vial contains glycerol and distilled water). Each test vial is stored under refrigeration at four degrees Celsius (4° C.), in a cool, dark place, away from bright light.

The carrier for the first test vial contains five (5) percent glycerol in water (on a weight by volume basis or w/v basis) in a total final carrier volume of ten milliliters.

The carrier for the second test vial contains ten (10) percent glycerol in water (on a weight by volume basis or w/v basis) in a total final carrier volume of ten milliliters.

The carrier for the third test vial contains fifteen (15) percent glycerol in water (on a weight by volume basis or w/v basis) in a total final carrier volume of ten milliliters.

The carrier for the fourth test vial contains twenty (20) percent glycerol in water (on a weight by volume basis or w/v basis) in a total final carrier volume of ten milliliters.

The carrier for the fifth test vial contains twenty-five (25) percent glycerol in water (on a weight by volume basis or w/v basis) in a total final carrier volume of ten milliliters.

Based on these conditions, stability tests are then performed, and the stability of rusalatide acetate is thus analyzed and evaluated in the control vial and each of the test vials. Measurements are taken to measure any degradation of rusalatide acetate, including degradation of any Monomer or Dimer. Measurements (i.e., to analyze for any degradation) are taken at several time points after "time zero", including measurements at three days, five days, one week, two weeks, three weeks, one month, two months, three months, five months, and six months after "time zero" (i.e., after the beginning of the experiments).

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 11 in combination with all of the data and information obtained from this study (as described herein, in Example 12), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of the carrier tested on stability.

Example 13

A series of controlled experiments are performed (i.e., with all proper control groups, for statistical analysis) under sterile conditions to test and evaluate the extent to which pH is a parameter that affects the stability of Monomer.

At "day one", several opaque "test vials" are prepared, and each separate opaque test vial contains rusalatide acetate in a saline solution (each opaque vial is prepared by placing one milligram of solid lyophilized rusalatide acetate in standard 0.9% sodium chloride saline). Each test vial is an opaque vial, to protect the rusalatide acetate from exposure to light, and each test vial is stored at about four degrees Celsius (about 4° C.), in a cool, dark place, away from bright light.

The first opaque test vial is maintained at a pH of about four (4.0).

The second opaque test vial is maintained at a pH of about four and one-half (4.5).

The third opaque test vial is maintained at a pH of about five (5.0).

The fourth opaque test vial is maintained at a pH of about five and one-half (5.5).

The fifth opaque test vial is maintained at a pH of about six (6.0).

The sixth opaque test vial is maintained at a pH of about six and one-half (6.5).

The seventh opaque test vial is maintained at a pH of about seven (7.0).

The eighth opaque test vial is maintained at a pH of about seven and one-half (7.5).

The ninth opaque test vial is maintained at a pH of about eight (8.0).

The tenth opaque test vial is maintained at a pH of about eight and one-half (8.5).

The eleventh opaque test vial is maintained at a pH of about nine (9.0).

Based on these conditions, stability tests are then performed, and measurements are taken, to measure whether there is any degradation of Monomer in the different test vials. Measurements (i.e., to analyze for any degradation of Monomer) are taken at several time points after "day one", including measurements at three days, five days, one week, two weeks, three weeks, one month, two months, three months, five months, and six months after "day one" (i.e., after the beginning of the experiments).

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 12 in combination with all of the data and information obtained from this study (as described herein, in Example 13), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of pH on the stability of Monomer, and whether adjustment in pH can be utilized to help control the rate of formation of Dimer.

Example 14

First Temperature Study

In a first study, experiments are performed under sterile conditions to test and evaluate the extent to which temperature is a parameter that affects the stability of rusalatide acetate. In this first study, at "day one", several opaque "test vials" are prepared, and each test vial contains one milligram of rusalatide acetate peptide in a lyophilized or freeze-dried form. Each test vial is a vacuum-sealed, opaque vial, to protect the rusalatide acetate from exposure to light, and each test vial is stored in a separate, temperature-controlled, dark room, and away from bright light.

The first opaque test vial is maintained at about minus eighty (−80) degrees Celsius.
The second opaque test vial is maintained at about minus seventy-five (−75) degrees Celsius.
The third opaque test vial is maintained at about minus seventy (−70) degrees Celsius.
The fourth opaque test vial is maintained at about minus sixty-five (−65) degrees Celsius.
The fifth opaque test vial is maintained at about minus sixty (−60) degrees Celsius.
The sixth opaque test vial is maintained at about minus fifty-five (−55) degrees Celsius.
The seventh opaque test vial is maintained at about minus fifty (−50) degrees Celsius.
The eighth opaque test vial is maintained at about minus forty-five (−45) degrees Celsius.
The ninth opaque test vial is maintained at about minus forty (−40) degrees Celsius.
The tenth opaque test vial is maintained at about minus thirty-five (−35) degrees Celsius.
The eleventh opaque test vial is maintained at about minus thirty (−30) degrees Celsius.
The twelfth opaque test vial is maintained at about minus twenty-five (−25) degrees Celsius.
The thirteenth opaque test vial is maintained at about minus twenty (−20) degrees Celsius.

Based on these conditions, stability tests are then performed, and measurements are taken, to measure whether there is any degradation of rusalatide acetate in the different test vials. Measurements (i.e., to analyze for any degradation of rusalatide acetate) are taken at several time points after "day one", including measurements at three days, five days, one week, two weeks, three weeks, one month, two months, three months, five months, and six months after "day one" (i.e., after the beginning of the experiments).

Second Temperature Study

In a second study, additional experiments are performed under sterile conditions to test and evaluate the extent to which temperature is a parameter that affects stability. At "day one", several opaque "test vials" are prepared, and each separate opaque test vial contains rusalatide acetate peptide in saline solution (each opaque vial is prepared by placing one milligram of solid lyophilized rusalatide acetate in standard 0.9% sodium chloride saline). Each test vial is an opaque vial, to protect the rusalatide acetate from exposure to light, and each test vial is stored in a separate, temperature-controlled, dark room, and away from bright light.

The first opaque test vial is maintained at about four degrees Celsius.
The second opaque test vial is maintained at about four and one-half degrees Celsius.
The third opaque test vial is maintained at about five degrees Celsius.
The fourth opaque test vial is maintained at about five and one-half degrees Celsius.
The fifth opaque test vial is maintained at about six degrees Celsius.
The sixth opaque test vial is maintained at about six and one-half degrees Celsius.
The seventh opaque test vial is maintained at about seven degrees Celsius.
The eighth opaque test vial is maintained at about seven and one-half degrees Celsius.
The ninth opaque test vial is maintained at about eight degrees Celsius.
The tenth opaque test vial is maintained at about eight and one-half degrees Celsius.
The eleventh opaque test vial is maintained at about nine degrees Celsius.

Based on these conditions, stability tests are then performed, and measurements are taken, to measure whether there is any degradation of rusalatide acetate in the different test vials. Measurements (i.e., to analyze for any degradation of rusalatide acetate) are taken at several time points after "day one", including measurements at three days, five days, one week, two weeks, three weeks, one month, two months, three months, five months, and six months after "day one" (i.e., after the beginning of the experiments).

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 13 in combination with all of the data and information obtained from this study (as described herein, in Example 14), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of temperature on stability.

Example 15

A series of controlled experiments are performed (i.e., with all proper control groups, for statistical analysis) under sterile conditions to test and evaluate the extent to which freeze-thaw cycles affect stability.

At "day one", a "control vial" is prepared, in which the control vial contains rusalatide acetate peptide in saline solution (the control vial is an opaque vial, and is prepared by placing one milligram of solid lyophilized rusalatide acetate in standard 0.9% sodium chloride saline). The control vial is opaque to protect the rusalatide acetate from exposure to light, and the vial is stored in a separate, temperature-controlled, dark room, and away from bright light. During the entire period of the study, the control vial is not subjected to any freeze-thaw (FT) cycles.

Also, at "day one", several opaque "test vials" are prepared, and each separate opaque test vial contains rusalatide acetate peptide in saline solution (each opaque test vial is prepared by placing one milligram of solid lyophilized rusalatide acetate in standard 0.9% sodium chloride saline). Each test vial is an opaque vial, to protect the rusalatide acetate from exposure to light, and each test vial is stored in a separate, temperature-controlled, dark room, and away from bright light.

- The first test vial is subjected to one freeze-thaw (FT) cycle.
- The second test vial is subjected to two freeze-thaw (FT) cycles.
- The third test vial is subjected to three freeze-thaw (FT) cycles.
- The fourth test vial is subjected to four freeze-thaw (FT) cycles.
- The fifth test vial is subjected to five freeze-thaw (FT) cycles.
- The sixth test vial is subjected to six freeze-thaw (FT) cycles.

Based on these conditions, stability tests are then performed, and measurements are taken, to measure whether there is any degradation of rusalatide acetate in the different test vials. Measurements (i.e., to analyze for any degradation of rusalatide acetate) are taken at several time points after "day one", including measurements at three days, five days, one week, two weeks, three weeks, one month, two months, three months, five months, and six months after "day one" (i.e., after the beginning of the experiments).

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 14 in combination with all of the data and information obtained from this study (as described herein, in Example 15), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of freeze-thaw cycles on stability.

Example 16

A series of controlled experiments are performed (i.e., with all proper control groups, for statistical analysis) under sterile conditions to test and evaluate the effect of various excipients on the stability of rusalatide acetate. A wide range of excipients are evaluated in a wide range of different formulations, pharmaceutical compositions and dosage forms. The dosage forms include liquid dosage forms (saline as the carrier), topical dosage forms and other dosage forms that contain rusalatide acetate.

In one set of controlled experiments, tests are run to evaluate whether hydroxypropyl cellulose has any effect on stability of rusalatide acetate.

For the control group, at "day one", a topical dosage form is prepared that contains one milligram of rusalatide acetate and no hydroxypropyl cellulose.

Several test groups (dosage forms) are also prepared at "day one".

For the control group and the test groups, each dosage form is stored in a separate opaque vial, gently purged with non-reactive, anhydrous nitrogen gas (as a purging agent), sealed and then each vial is stored at four (4) degrees Celsius, and protected from light.

The first test group is a topical dosage form that contains one milligram of rusalatide acetate and one percent (1.0%) hydroxypropyl cellulose (as a percentage of the total weight of the topical rusalatide acetate dosage form).

The second test group is a topical dosage form that contains one milligram of rusalatide acetate and two percent (2.0%) hydroxypropyl cellulose (as a percentage of the total weight of the topical rusalatide acetate dosage form).

The third test group is a topical dosage form that contains one milligram of rusalatide acetate and three percent (3.0%) hydroxypropyl cellulose (as a percentage of the total weight of the topical rusalatide acetate dosage form).

The fourth test group is a topical dosage form that contains one milligram of rusalatide acetate and four percent (4.0%) hydroxypropyl cellulose (as a percentage of the total weight of the topical rusalatide acetate dosage form).

The fifth test group is a topical dosage form that contains one milligram of rusalatide acetate and five percent (5.0%) hydroxypropyl cellulose (as a percentage of the total weight of the topical rusalatide acetate dosage form).

Stability tests are then performed, and measurements are taken, to determine whether there is any degradation of rusalatide acetate in the different dosage forms. Measurements (i.e., to analyze for any degradation of rusalatide acetate) are taken at several time points after "day one", including measurements at three days, five days, one week, two weeks, three weeks, one month, two months, three months, five months, and six months after "day one" (i.e., after the beginning of the experiments). Results are analyzed to determine if the particular excipient (hydroxypropyl cellulose) has any effect on the stability of rusalatide acetate in the various dosage forms.

Similar types of controlled experiments are performed, after preparing other rusalatide acetate dosage forms, to determine if other specific excipients have any effect on the stability of rusalatide acetate in the various dosage forms. All the excipients and carriers evaluated are pharmaceutically acceptable, biocompatible, non-toxic, non-inflammatory, non-immunogenic and devoid of any type of contaminants.

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 15 in combination with all of the data and information obtained from this study (as described herein, in Example 16), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of specific types of excipients on stability.

Example 17

A series of controlled experiments are performed (i.e., with all proper control groups, for statistical analysis) under sterile conditions to test and evaluate the extent to which stability of rusalatide acetate (including Monomer and Dimer) is affected by interactions with the material composition of the inner surface of a storage container or vial.

At "day one", a control vial is prepared, and the control vial contains rusalatide acetate in a saline solution (prepared by placing one milligram of solid lyophilized rusalatide acetate in standard 0.9% sodium chloride saline). The control vial is an opaque vial, to protect the rusalatide acetate from exposure to light, and the vial is stored at about four degrees Celsius (about 4° C.), in a cool, dark place, away from bright light. The inner surface of the control vial does not contain any hydrophilic mesoporous silica pores.

Also at "day one", a set of ten (10) different test vials are prepared. Each test vial contains rusalatide acetate in a saline solution (prepared by placing one milligram of solid lyophilized rusalatide acetate in standard 0.9% sodium chloride saline). Each test vial is an opaque vial, to protect the rusalatide acetate from exposure to light, and the vial is stored at about four degrees Celsius (about 4° C.), in a cool, dark place, away from bright light. The inner surface of each test vial does contain a uniform layer of hydrophilic mesoporous silica pores.

Stability tests are performed at different time points, at three days, one week, two weeks, three weeks, one month, three months, six months, eight months and twelve months after "day one". Results are analyzed to compare the stability of rusalatide acetate in the control vial versus the test vials, and to determine whether the absence versus presence of hydrophilic mesoporous silica pores on the inner surface of the vial has any effect on the stability of rusalatide acetate.

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 16 in combination with all of the data and information obtained from this study (as described herein, in Example 17), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of hydrophilic mesoporous silica pores (i.e., hydrophilic mesoporous silica pores on the inner surface of a vial that contains rusalatide acetate) on stability.

Example 18

A series of controlled experiments are performed (i.e., with all proper control groups, for statistical analysis) under sterile conditions to evaluate whether there is an impact of exposure to light on stability (and to understand whether there are any effects of photolysis and photo-oxidation on the stability of rusalatide acetate).

At "day one", a control vial is prepared, and the control vial contains rusalatide acetate in a saline solution (prepared by placing one milligram of solid lyophilized rusalatide acetate in standard 0.9% sodium chloride saline). The control vial is an opaque vial, to protect the rusalatide acetate from exposure to light, and the vial is stored at about four degrees Celsius (about 4° C.) throughout the study. Thus the control vial is not exposed to any light.

Also at "day one", a first set of test vials is prepared. Each test vial contains rusalatide acetate in a saline solution (prepared by placing one milligram of solid lyophilized rusalatide acetate in standard 0.9% sodium chloride saline). Each test vial is a transparent vial (i.e., light can pass through the surface of the vial, to the interior of the vial), to allow for exposure of the rusalatide acetate solution to light, and each test vial is stored at about four degrees Celsius (about 4° C.) throughout the study.

The first test vial is exposed to 0.8 million lux hour of white (visible) light.
The second test vial is exposed to about 1.0 million lux hour of white (visible) light.
The third test vial is exposed to about 1.2 million lux hour of white (visible) light.
The fourth test vial is exposed to about 1.4 million lux hour of white (visible) light.
The fifth test vial is exposed to about 1.6 million lux hour of white (visible) light.
The sixth test vial is exposed to about 1.8 million lux hour of white (visible) light.

In addition, at "day one", a second set of test vials is prepared. Each test vial contains rusalatide acetate in a saline solution (prepared by placing one milligram of solid lyophilized rusalatide acetate in standard 0.9% sodium chloride saline). Each test vial is a transparent vial (i.e., light can pass through the surface of the vial, to the interior of the vial), to allow for exposure of the rusalatide acetate solution to light, and each test vial is stored at about four degrees Celsius (about 4° C.) throughout the study.

The first test vial is exposed to about 160 watt hours per square meter of ultraviolet (UV) light.
The second test vial is exposed to about 180 watt hours per square meter of UV light.
The third test vial is exposed to about 200 watt hours per square meter of UV light.
The fourth test vial is exposed to about 220 watt hours per square meter of UV light.
The fifth test vial is exposed to about 240 watt hours per square meter of UV light.

The sixth test vial is exposed to about 260 watt hours per square meter of UV light.

Stability tests are performed at different time points, at three days, one week, two weeks, three weeks, one month, three months, six months, eight months and twelve months after "day one". Results are analyzed to compare the stability of rusalatide acetate in the control vial versus the test vials, and to determine whether (i) exposure to white (visible) light has any effect on the stability of rusalatide acetate, and whether (ii) exposure to UV light has any effect on the stability of rusalatide acetate. Analysis is performed to determine if there are any effects (for example, photolysis or photo-oxidation) on the stability of rusalatide acetate, and the presence or occurrence of photodegradation is monitored by using a spectrophotometric method and analyzed using a computer-based instrumentation system.

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 17 in combination with all of the data and information obtained from this study (as described herein, in Example 18), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of light exposure on stability.

Example 19

A series of controlled experiments are performed (i.e., with all proper control groups, for statistical analysis) under sterile conditions to evaluate whether there is an effect of redox-active transition metal impurities on stability.

At "day one", a control vial is prepared, and the control vial contains rusalatide acetate in a saline solution (prepared by placing one milligram of solid lyophilized rusalatide acetate in standard 0.9% sodium chloride saline). The control vial is an opaque vial, to protect the rusalatide acetate from exposure to light, and the vial is stored at about four degrees Celsius (about 4° C.), in a cool, dark place, away from bright light. Analytical tests are performed and confirm that the control vial does not contain any redox-active transition metal impurities.

Also at "day one", a set of ten (10) different test vials are prepared. Each test vial contains rusalatide acetate in a saline solution (prepared by placing one milligram of solid lyophilized rusalatide acetate in standard 0.9% sodium chloride saline). Each test vial is an opaque vial, to protect the rusalatide acetate from exposure to light, and each test vial is stored at about four degrees Celsius (about 4° C.), in a cool, dark place, away from bright light. Analytical tests are performed and confirm that each of the test vials contains one or more types of redox-active transition metal impurities.

Stability tests are performed at different time points, at three days, one week, two weeks, three weeks, one month, three months, six months, eight months and twelve months after "day one". Results are analyzed to compare the stability of rusalatide acetate in the control vial versus the test vials, and to determine whether the absence versus presence of redox-active transition metal impurities has any effect on the stability of rusalatide acetate.

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 18 in combination with all of the data and information obtained from this study (as described herein, in Example 19), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of redox-active transition metal impurities on stability.

Example 20

A series of controlled experiments are performed (i.e., with all proper control groups, for statistical analysis) to evaluate whether there is an effect of endotoxins on stability.

At "day one", a control vial is prepared, and the control vial contains rusalatide acetate in a saline solution (prepared by placing one milligram of solid lyophilized rusalatide acetate in standard 0.9% sodium chloride saline). The control vial is an opaque vial, to protect the rusalatide acetate from exposure to light, and the vial is stored at about four degrees Celsius (about 4° C.), in a cool, dark place, away from bright light. Analytical tests are performed and confirm that the control vial does not contain any endotoxins.

Also at "day one", a set of ten (10) different test vials are prepared. Each test vial contains rusalatide acetate in a saline solution (prepared by placing one milligram of solid lyophilized rusalatide acetate in standard 0.9% sodium chloride saline). Each test vial is an opaque vial, to protect the rusalatide acetate from exposure to light, and each test vial is stored at about four degrees Celsius (about 4° C.), in a cool, dark place, away from bright light. Analytical tests are performed and confirm that each of the test vials contains one or more types of endotoxins.

Stability tests are performed at different time points, at three days, one week, two weeks, three weeks, one month, three months, six months, eight months and twelve months after "day one". Results are analyzed to compare the stability of rusalatide acetate in the control vial versus the test vials, and to determine whether the absence versus presence of endotoxins has any effect on the stability of rusalatide acetate.

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 19 in combination with all of the data and information obtained from this study (as described herein, in Example 20), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of endotoxins on stability.

Example 21

A series of controlled experiments are performed (i.e., with all proper control groups, for statistical analysis) to evaluate whether there is an effect of nitrogen (a non-reactive, anhydrous purging agent) on stability.

At "day one", a control vial is prepared, and the control vial contains rusalatide acetate in a saline solution (prepared by placing one milligram of solid lyophilized rusalatide acetate in standard 0.9% sodium chloride saline). The control vial is an opaque vial, to protect the rusalatide acetate from exposure to light, and the vial is stored at about four degrees Celsius (about 4° C.), in a cool, dark place, away from bright light. Before the vial is packaged and sealed, no steps are taken to displace the ambient oxygen within the vial (there is no use of nitrogen as a non-reactive, anhydrous purging agent).

Also at "day one", a set of six (6) different test vials are prepared. Each test vial contains rusalatide acetate in a saline solution (prepared by placing one milligram of solid lyophilized rusalatide acetate in standard 0.9% sodium chloride saline). Each test vial is an opaque vial, to protect the rusalatide acetate from exposure to light, and each test vial is stored at about four degrees Celsius (about 4° C.), in a cool, dark place, away from bright light. Before each test vial is packaged and sealed, steps are taken to carefully displace the ambient oxygen within each test vial by using nitrogen as a non-reactive, anhydrous purging agent.

Stability tests are performed at different time points, at three days, one week, two weeks, three weeks, one month, three months, six months, eight months and twelve months after "day one". Results are analyzed to compare the stability of rusalatide acetate in the control vial as compared to rusalatide acetate in each of the test vials, and to determine whether the absence versus presence of nitrogen (as a non-reactive, anhydrous purging agent) has any effect on the stability of rusalatide acetate (including Monomer and Dimer).

An experienced analyst uses a physical, tangible computer system that includes a processor, a memory storage device and other computer system components (it is noted, for these studies and for analyzing the results, that the computer system is required and essential for the analysis). The computer system is used to simultaneously analyze all of the previously obtained, combined data and information which includes all the combined data from Examples 1 through 20 in combination with all of the data and information obtained from this study (as described herein, in Example 21), and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling also provide very valuable information about the effects of nitrogen (as a non-reactive, anhydrous purging agent) on stability.

Example 22

An experienced analyst uses a physical, tangible computer system that includes a processor, a memory storage device and other computer system components (it is noted that the computer system is required and essential for the analysis). The computer system is used to simultaneously analyze all of the previously obtained, combined data and information which includes all the combined data from Examples 1 through 21, as described herein, and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling provide very valuable information for designing a safe and effective pharmaceutical composition. Based on this analysis and information, a rusalatide acetate composition is prepared, and the rusalatide acetate composition includes a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1). The polypeptide is synthesized and purified according to Good Manufacturing Practice (GMP) requirements, and the composition is essentially free of reactive oxygen species, endotoxins, organic solvents, degradation impurities, and redox-active transition metal impurities. The composition also includes at least one pharmaceutically acceptable excipient, and the composition is prepared under aseptic conditions, and stored with a hygroscopic agent. The composition is stable, protected from light, and the composition is packaged and sealed after exposure to a non-reactive, anhydrous purging agent. Stability of the composition is determined based on a combination of forced degradation analysis, analysis of water content in the composition, counterion quantification analysis, and bioburden testing of the composition.

In other studies, a rusalatide acetate composition is prepared in which the polypeptide (i.e., the polypeptide comprising SEQ ID NO:1) is lyophilized. In additional studies, a rusalatide acetate composition is formulated for sterile administration. In further studies, a rusalatide acetate composition is formulated and comprises an antioxidant.

Example 23

An experienced analyst uses a physical, tangible computer system that includes a processor, a memory storage device and other computer system components (it is noted that the computer system is required and essential for the analysis). The computer system is used to simultaneously analyze all of the previously obtained, combined data and information which includes all the combined data from Examples 1 through 21, as described herein, and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling provide very valuable information for designing a safe and effective pharmaceutical composition. Based on this analysis and information, a rusalatide acetate composition is prepared, and the composition includes a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1). The polypeptide is synthesized and purified according to Good Manufacturing Practice (GMP) requirements, and the composition is essentially free of reactive oxygen species, endotoxins, organic solvents, degradation impurities, and redox-active transition metal impurities. The composition also includes a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond. The composition also includes an aqueous carrier. The composition is prepared under aseptic conditions, and the stability of the composition is determined based at least on a combination of forced degradation analysis, counterion quantification analysis, and bioburden testing of the composition.

Another pharmaceutical composition is prepared, in which the polypeptide has a purity of at least 99%.

Another pharmaceutical composition is prepared, in which the composition is formulated for sterile administration.

Yet another pharmaceutical composition is prepared, in which the composition is formulated as a single use liquid dosage form.

Yet another pharmaceutical composition is prepared, in which the composition also includes an antioxidant.

Example 24

An experienced analyst uses a physical, tangible computer system that includes a processor, a memory storage device and other computer system components (it is noted that the computer system is required and essential for the analysis). The computer system is used to simultaneously analyze all of the previously obtained, combined data and information which includes all the combined data from Examples 1 through 21, as described herein, and the computer system is used for performing computational analysis that utilizes predictive analytics, machine learning and predictive modeling. Based on the simultaneous analysis of all the data, the predictive analytics, machine learning and predictive modeling provide information about specific conditions that would be beneficial during pre-formulation and formulation stages for enhancing and optimizing the stability of rusalatide acetate including rusalatide acetate in a pharmaceutical composition. Utilizing the computer system, the predictive analytics, machine learning and predictive modeling provide very valuable information for designing a safe and effective pharmaceutical composition. Based on this analysis and information, a stable polypeptide composition is prepared, and the composition includes a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), the polypeptide having been synthesized and purified according to Good Manufacturing Practice (GMP) requirements. The composition is essentially free of reactive oxygen species, endotoxins, organic solvents, degradation impurities, and redox-active transition metal impurities. The composition also includes a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond. The composition also includes at least one pharmaceutically acceptable excipient, and the composition is stable, protected from light, and prepared under aseptic conditions. Stability of the composition is determined based at least on a combination of forced degradation analysis, analysis of water content in the composition, counterion quantification analysis, and bioburden testing of the composition.

Another rusalatide acetate composition is prepared, in which the composition is at least 90 percent free of reactive oxygen species, endotoxins, organic solvents, degradation impurities, and redox-active transition metal impurities.

Another rusalatide acetate composition is prepared, in which the composition is formulated for topical administration.

Another rusalatide acetate composition is prepared, in which the composition is formulated for sterile administration.

Another rusalatide acetate composition is prepared, in which the composition is formulated for sterile, injectable delivery.

Another rusalatide acetate composition is prepared, in which the composition includes an antioxidant.

Another rusalatide acetate composition is prepared, in which the composition is formulated as a single use liquid dosage form.

Example 25

An experienced analyst uses a physical, tangible computer system that includes a processor, a memory storage device and other computer system components (it is noted that the computer system is required and essential for the analysis). The computer system is used to simultaneously analyze all of the previously obtained, combined data and information which includes all the combined data from Examples 1 through 21, as described herein, and the computer system is used for performing computational analysis that utilizes predictive analytics, machine learning and predictive modeling.

Methods are developed for enhancing the stability of a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1). The following methods and procedures are carried out by experienced professionals:

simultaneously gathering information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide, performing an analysis of the information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide; and performing at least one stability optimization procedure based on the analysis such that the stability of the polypeptide is enhanced.

Example 26

An experienced analyst uses a physical, tangible computer system that includes a processor, a memory storage device and other computer system components (it is noted that the computer system is required and essential for the analysis). The computer system is used to simultaneously analyze all of the previously obtained, combined data and information which includes all the combined data from Examples 1 through 21, as described herein, and the computer system is used for performing computational analysis that utilizes predictive analytics, machine learning and predictive modeling.

Methods are developed for enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond. The following methods and procedures are carried out by experienced professionals:

simultaneously gathering information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer, performing an analysis of the information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer; and performing at least one stability optimization procedure based on the analysis such that the stability of the peptide dimer is enhanced.

Example 27

A system (comprising a computer system with necessary hardware components) is designed, developed and manufactured for enhancing the stability of a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1). The system (comprising a computer system with necessary hardware components) includes analytical components for:

simultaneously gathering information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide, performing an analysis of the information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide; and performing at least one stability optimization procedure based on the analysis such that the stability of the polypeptide is enhanced, and the system also includes a processor and a memory storage device for storing the information about the effects of atmospheric oxygen, reactive oxygen species, moisture content, carrier, pH, temperature, freeze-thaw cycles, conformational changes in the structure of the polypeptide, buffer composition, counterions, excipients, sterility, viscosity, light exposure, bioburden and redox-active transition metal impurities on the stability of the polypeptide.

Example 28

A system (comprising a computer system with necessary hardware components) is designed, developed and manufactured for enhancing the stability of a peptide dimer having two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the polypeptides are covalently linked by a disulfide bond. The system (comprising a computer system with necessary hardware components) includes analytical components for:

simultaneously gathering information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer, performing an analysis of the information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer; and performing at least one stability optimization procedure based on the analysis such that the stability of the peptide dimer is enhanced, and the system also includes a processor and a memory storage device for storing the information about the effects of atmospheric oxygen, reactive oxygen species, moisture content, carrier, pH, temperature, freeze-thaw cycles, conformational changes in the structure of the peptide dimer, buffer composition, counterions, excipients, sterility, viscosity, light exposure, bioburden and redox-active transition metal impurities on the stability of the peptide dimer.

Example 29

The tissue distribution of post-administered rusalatide acetate is assessed using radiolabeled rusalatide acetate. Tritiated rusalatide acetate is administered to a murine model, using a Balb/C mouse. Thereafter, the mouse is euthanized and samples taken of the large organs (including the liver, brain, pancreas and kidneys) and homogenized with PBS. Antibodies to rusalatide acetate are incubated with beads coated with protein G to bind to the Fc portion of antibody molecules. After about two (2) hours, the beads are pelleted by centrifugation, washed three times with cold PBS and counted in a scintillation counter. The data collected shows the tissue distribution of rusalatide acetate.

It is to be understood that, in preferred embodiments, the physical, non-abstract computer-based instrumentation systems of the present invention comprise at least one physical component of computer hardware architecture or microarchitecture which is essential and required to specifically perform the methods of the present invention as described herein.

While the present invention has been particularly shown and described with reference to preferred embodiments thereof, it will be understood by those skilled in the art that various changes in form and details may be made therein without departing from the scope of the present invention.

SEQUENCE LISTING (SEQ ID NO: 1)
AGYKPDEGKRGDACEGDSGGPFV

---

---

The invention claimed is:

1. A stable polypeptide composition comprising:
(a) a 23 amino acid polypeptide comprising Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO: 1), the polypeptide having been synthesized and purified according to Good Manufacturing Practice (GMP) requirements,
(b) a peptide dimer comprising two polypeptides, each with the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:1), wherein the two polypeptides are covalently linked by a disulfide bond, and
(c) an aqueous carrier, wherein the carrier comprises glycerol and water,
further wherein the composition comprises chitosan,
further wherein the composition comprises polyvinylpyrrolidone,
further wherein the composition comprises polyethylene glycol,
further wherein the composition comprises trehalose,
further wherein the composition comprises xanthan gum,
further wherein the composition comprises guar gum,
further wherein the composition comprises sodium alginate,
further wherein the composition comprises calcium trisodium diethylenetriaminepentaacetic acid,
further wherein the composition is a single use liquid dosage form,
further wherein the composition has a purity of at least ninety percent,
further wherein the composition is at least ninety percent free of reactive oxygen species, endotoxins, organic solvents, degradation impurities, and redox-active transition metal impurities.

2. The composition of claim 1, wherein the composition is at least 99 percent free of reactive oxygen species, endotoxins, organic solvents, degradation impurities, and redox-active transition metal impurities.

* * * * *